(12) United States Patent
Robbins et al.

(10) Patent No.: US 10,758,522 B2
(45) Date of Patent: Sep. 1, 2020

(54) SMALL MOLECULE ANALOGS OF THE NEMO BINDING PEPTIDE

(71) Applicant: THE SCRIPPS RESEARCH INSTITUTE, La Jolla, CA (US)

(72) Inventors: Paul Robbins, Juno Beach, FL (US); Laura Niedernhofer, Juno Beach, FL (US); Theodore Kamenecka, Palm Beach Gardens, FL (US); Gabriela Mustata Wilson, Evansville, IN (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/579,103

(22) PCT Filed: May 25, 2016

(86) PCT No.: PCT/US2016/034083
§ 371 (c)(1),
(2) Date: Dec. 1, 2017

(87) PCT Pub. No.: WO2016/196117
PCT Pub. Date: Dec. 8, 2016

(65) Prior Publication Data
US 2018/0169078 A1    Jun. 21, 2018

Related U.S. Application Data

(60) Provisional application No. 62/169,266, filed on Jun. 1, 2015.

(51) Int. Cl.
| | |
|---|---|
| *C07D 213/74* | (2006.01) |
| *A61K 31/444* | (2006.01) |
| *A61K 31/4427* | (2006.01) |
| *A61K 31/44* | (2006.01) |
| *A61P 21/00* | (2006.01) |
| *A61P 9/10* | (2006.01) |
| *A61P 11/06* | (2006.01) |
| *A61P 19/02* | (2006.01) |
| *A61P 3/10* | (2006.01) |
| *A61P 25/16* | (2006.01) |
| *A61P 35/00* | (2006.01) |
| *A61K 31/4439* | (2006.01) |

(52) U.S. Cl.
CPC ............ *A61K 31/444* (2013.01); *A61K 31/44* (2013.01); *A61K 31/4427* (2013.01); *A61K 31/4439* (2013.01); *A61P 3/10* (2018.01); *A61P 9/10* (2018.01); *A61P 11/06* (2018.01); *A61P 19/02* (2018.01); *A61P 21/00* (2018.01); *A61P 25/16* (2018.01); *A61P 35/00* (2018.01); *C07D 213/74* (2013.01)

(58) Field of Classification Search
CPC .................................................... C07D 213/74
See application file for complete search history.

(56) References Cited

U.S. PATENT DOCUMENTS

| 6,562,811 B1 | 5/2003 | Murata et al. |
| 2005/0288285 A1 | 12/2005 | Cywin et al. |
| 2009/0075902 A1 | 3/2009 | Robbins et al. |

FOREIGN PATENT DOCUMENTS

WO    WO-2016196117 A1    12/2016

OTHER PUBLICATIONS

ZINC15 public database, http://zinc15.docking.org/ for ZINC ID numbers shown in accompanying IDS cover sheet.
"International Application Serial No. PCT/US2016/034083, International Search Report dated Oct. 4, 2016", 5 pgs.
"International Application Serial No. PCT/US2016/034083, Written Opinion dated Oct. 4, 2016", 4 pgs.
"Substance Record for SID 74790018", PubChem, [Online] Retrieved from the Internet: <https://pubchem.ncbi.nlm.nih.gov/substance/74790018>, (Deposit Date: Jun. 11, 2009), 6 pgs.
"International Application Serial No. PCT US2016 034083, International Preliminary Report on Patentability dated Dec. 14, 2017", 6 pages.
"International Application Serial No. PCT US2016 034083, Invitation to Pay Additional Fees dated Jul. 12, 2016", 2 pages.

*Primary Examiner* — Brian E McDowell
(74) *Attorney, Agent, or Firm* — Schwegman Lundberg & Woessner, P.A.

(57) ABSTRACT

The invention is directed to a method of inhibiting, within a living cell, the interaction between NF-κB essential modulator ("NEMO") with IκB kinase-β (IKK-β) at the NEMO binding domain (NBD), comprising exposing the cell to an effective amount or concentration of a compound of the invention, a NEMO-binding domain analog (NBDA). The invention is further directed to a method of treating a condition in a patient, wherein inhibiting the interaction between NF-κB essential modulator ("NEMO") with IκB kinase-β (IKK-β) at the NEMO binding domain (NBD) is medically indicated, comprising administering to the patient an effective dose of a compound of the invention. Conditions that can be treated by a method of the invention includes muscular dystrophy, asthma, inflammatory bowel disease, multiple sclerosis, Parkinson's Disease, arthritis, diabetes, graft versus host disease, accelerated aging, heart ischemia, cancer, UV-induced skin damage, or an age-related pathology.

4 Claims, 44 Drawing Sheets

Zinc-13

Zinc-5

IKK/NF-κB Inhibitory Peptides

| Transduction Domain | GG | NEMO Binding Peptide |

| Name | PTD | NEMO Binding Peptide |
|------|-----|----------------------|
| PTD-5 | RRQRRTSKLMKR | TALDWSWLQTE |
| 8K | KKKKKKKK | TALDWSWLQTE |
| 6R | RRRRRR | TALDWSWLQTE |
| TAT | YGRKKRRQRRR | TALDWSWLQTE |
| Antp | RQIKIWFQNRRMKW | TALDWSWLQTE |

Experimental design for Screening Therapeutic Agents on Skin

Wild-type    K14-Cre;Ercc1⁻/flox

Test agent 1

Test agent 2

Vehicle only

Treated mice daily x 4 weeks with 2 drugs & vehicle only

| Ctrl | 5 1hr | 5 4hr | 13 1hr | 13 4hr | NBD 1hr | NBD 4hr | 7 1hr | 7 4hr |

8K-NBD Treatment Improves Skin Pathology
after UV Exposure

NBDA-1 (Zinc13) Treatment Increases
Epidermal Thickness in Aged Skin

NBDA1 Treatment Increases GAG Content in the Intervertebral Disc of *Ercc1*$^{-/\Delta}$ mice

Screen for Drugs that Rescue Oxidative Stress Induced Senescence: Anti-Aging Drugs Passage 5 *Ercc1*$^{-/-}$ MEFs 20% $O_2$ Stripay et al, *In preparation*

SMALL MOLECULE ANALOGS OF THE NEMO BINDING PEPTIDE

CROSS-REFERENCE TO RELATED APPLICATIONS

This application claims the priority of U.S. provisional patent application Ser. No. 62/169,266, filed Jun. 1, 2015, the disclosure of which is incorporated herein by reference in its entirety.

This application makes reference to the contents of U.S. published patent application Ser. No. 12/126,634, publication number US2009/0075902 filed on May 23, 2008 which claims priority to U.S. Provisional Application No. 60/940,312 filed May 25, 2007, the contents of which are incorporated herein by reference in their entireties.

BACKGROUND

Published United States patent application US2009/0075902, by certain of the inventors herein, describes peptides which block the interaction between NF-κB essential modulator ("NEMO") with IκB kinase-β (IKK-β), the contents of which are expressly incorporated by reference.

The transcription factor NF-κB is a central component of the cellular response to damage, stress and inflammation. In mammals, the NF-κB family consists of five subunits, RelA or p65, c-Rel, RelB, p50, and p52. NF-κB binds to DNA as a dimer, the most common being the p65p50 heterodimer. The p65"p50 heterodimer is localized primarily in the cytoplasm, maintained in this inactive state via sequestration by IκB proteins. NF-κB activation via the canonical pathway is mediated by the upstream IκB kinase (IKK), a heterotrimer consisting of two catalytic subunits, IKKα and IKKß, and a regulatory subunit termed IKKγ or NEMO (NF-κB Essential Modulator). In response to a variety of factors, including pro-inflammatory cytokines, pathogens, oxidative stress and growth factors, IKK is activated and phosphorylates IκB, leading to its polyubiquitination and subsequent proteosomal degradation. IκB degradation allows NF-κB to translocate to the nucleus where it binds to its cognate DNA sequence as well as co-activators such as CBP/p300, to regulate gene expression.

Chronic activation of NF-κB is associated with numerous diseases including sepsis, asthma, muscle atrophy, multiple sclerosis, atherosclerosis, heart disease, both type I and II diabetes, osteoarthritis, dementia, osteoporosis, and cancer, most of which are associated with increasing chronologic age. NF-κB transcriptional activity is increased with age in numerous tissues in rodents including skin, liver, kidney, cerebellum, cardiac muscle, and gastric mucosa. Cells from aged humans and patients with Hutchinson-Gilford progeria have a similar upregulation of NF-κB activity. Recently, several studies suggest that NF-κB could have a causal role in aging and age-related degeneration. NF-κB was identified as the transcription factor most associated with mammalian aging. In addition, genetic inhibition of NF-κB in the skin of a transgenic mouse model reversed age-related gene expression and histologic changes, including increased epidermal thickness and reduction of senescence associated β-galactosidase activity.

An 11 amino acid sequence was identified within IKKß comprising the binding domain between IKKβ and IKKγ. This peptide, known as the NEMO binding domain (NBD), is able to block the interaction of IKKα and β (two catalytic subunits of NF-κB activation) with the regulatory subunit IKKγ (NEMO). When this short peptide sequence TALD-WSWLQTE was linked to a protein transduction domain, it led to a dose dependent inhibition of NF-κB signaling in tissue culture and in animal models. While there are numerous small molecule inhibitors of NF-κB, there are some distinct advantages of the NBD peptide. The site of action is highly defined, and only activated, but the basal level of NF-κB is not affected. Also, because of the high specificity of the NBD peptide sequence it is unlikely to affect other essential kinases, which is not the case for numerous other IKK inhibitors. The NBD peptide, when attached to a protein transduction domain, has been shown to be effective in treating a wide range of inflammatory and degenerative diseases including muscular dystrophy, inflammatory bowel disease, arthritis, diabetes, accelerated aging, Parkinson's Diseases, multiple sclerosis, asthma, heart ischemia and cancer. However, the cost of synthesis of the NBD peptide fused to NBD, as well as the fact that it is not orally active limits its therapeutic application.

Certain of the inventors herein have previously disclosed 7-[2-(cyclopropylmethoxy)-6-hydroxyphenyl]-5-[(3S)-3-piperidinyl]-1,4-dihydro-2H-pyrido[2,3-d][1,3]oxazin-2-one and its enantiomers; BAY11-7082 or BAY11-7085 (Axxora L.L.C., San Diego, Calif.) (Petegnief et al., 2001, Neuroscience 104:223); SC-514 (Kishore et al., 2003, J. Biol. Chem./278(35):32861; MG132 (Calbiochem, La Jolla, Calif.); tosyl-Phe-chloromethylketone ("TPCK"); (N-6-chloro-7-methoxy-9H-.beta.-carbolin-8-yl)-2-methylnicotinamide (ML120B, Wen et al., 2006, J. Pharm. Exp. Ther. 317:989-1001; Celastrol (Lee, et al., 2006, Biochem. Pharmacol. 72(10): 1311-1321); PG201 (Shin, et al., 2005, Biochem. Biophys. Res. Common. 331(4): 1469-1477); and MLN0415 (Millennium Pharmaceuticals, Cambridge, Mass.); as being effective in blocking the interaction of IKK-α and -β. These compounds however were ineffective in vivo due to limited stability and biodistribution.

SUMMARY

The present invention in various embodiments relates to methods for reducing and/or delaying one or more cellular responses to damage, stress and inflammation which comprise inhibiting NF-κB activation, preferably by blocking the interaction between NF-κB essential modulator ("NEMO") with IκB kinase-β (IKK-β) at the NEMO binding domain (NBD).

The invention is directed in various embodiments, to a method of inhibiting, within a living cell, the interaction between NF-κB essential modulator ("NEMO") with IκB kinase-β (IKK-β) at the NEMO binding domain (NBD), comprising exposing the cell to an effective amount or concentration of a compound of formula (I) as described herein. A compound of formula (I) is a NEMO-binding domain analog (NBDA). The invention is further directed in various embodiments to a method of treating a condition in a patient, wherein inhibiting the interaction between NF-κB essential modulator ("NEMO") with IκB kinase-β (IKK-β) at the NEMO binding domain (NBD) is medically indicated, comprising administering to the patient an effective dose of a compound of formula (I), optionally in a suitable carrier. Medical conditions that can be treated as disclosed and claimed herein are described below. A compound of formula (I) is

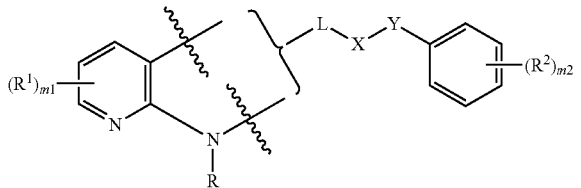

(I)

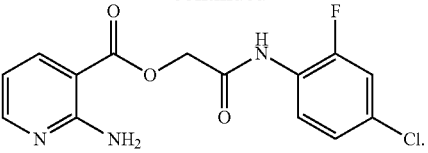

wherein a bracket indicates that the carbonyl group can be bonded to either bond indicated by a wavy line, provided that the other bond indicated by a wavy line is bonded to hydrogen;

the ring bonded to Y comprises 0 or 1 nitrogen atom;

R is H, $(C_1-C_6)$alkyl, $(C_3-C_6)$cycloalkyl$(C_1-C_6)$alkyl, or $(C_2-C_6)$acyl;

each $R^1$ is independently selected halo, alkyl, or haloalkyl; m1=0, 1, 2, or 3;

each $R^2$ is independently selected halo, alkyl, or haloalkyl; m2=0, 1, 2, or 3;

L is a bond, or is C(=O);

X is $(CH_2)_n$, O, O$(CH_2)_n$, $(CH_2)_n$O, NR, $(CH_2)_n$NR, or NR$(CH_2)_n$; or, X is a 5- or 6-membered heteroaryl ring;

Y is C(=O), C(=O)$(CH_2)_n$, NR, NR$(CH_2)_n$, C(=O)NR, or C(=O)NR$(CH_2)_n$;

n=1, 2, or 3;

or a pharmaceutically acceptable salt or a hydrate thereof.

In various embodiments, a compound of formula (I) for practicing a method of the invention can be a compound of formula (IA)

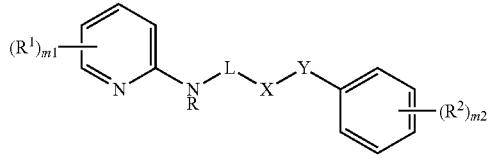

or a compound of formula (IB)

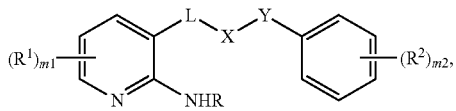

wherein the variable groups are as defined above.

In various embodiments, the invention provides a compound of formula (I), provided that the compound is not

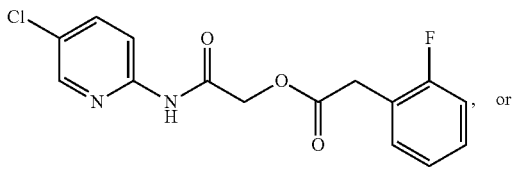

, or

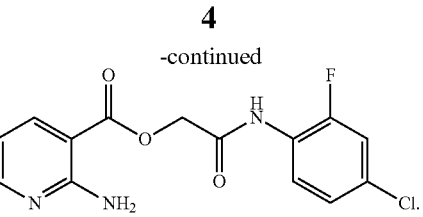

DETAILED DESCRIPTION

Figure 1:
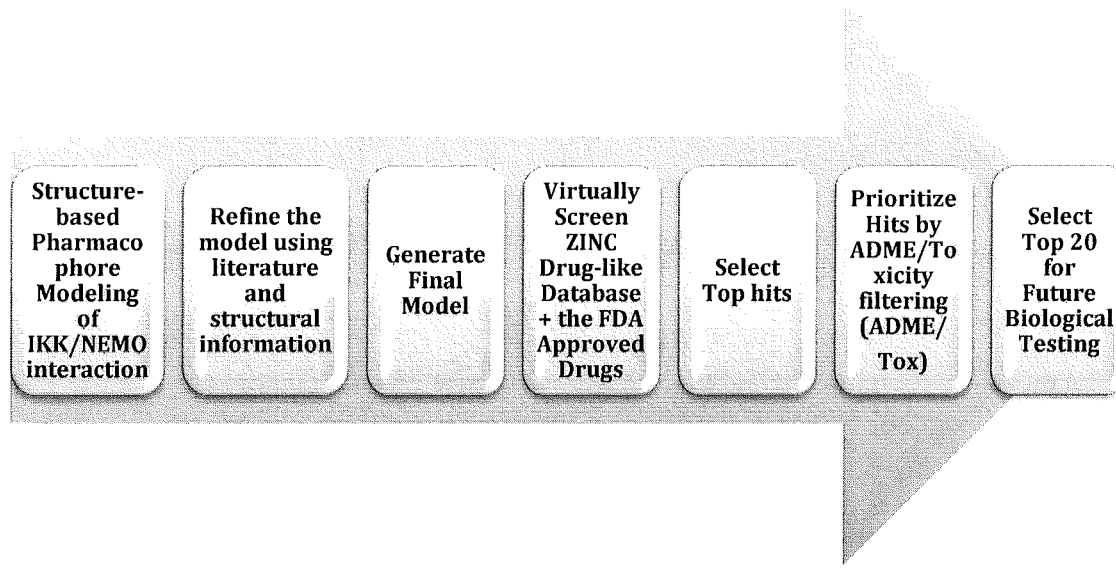
FIG. 1 is a flow chart showing the screening process for compounds from the virtual structure database ZINC 8.0 using the pharmacophore model of the invention.

Nuclear factor κB (NF-κB) is a transcription factor important for regulating immune responses, cell proliferation, apoptosis, embryonic development, senescence and cancer (1). In mammalian cells, NF-κB family is comprised of five subunits, RelA/p65, RelB, C-Rel, p50 (p105/NF-κB1) and p52 (p100/NF-κB2), all containing a Rel-homology domain (RHD) required for homo- or hetero-dimerization. NF-κB dimers are sequestered in the cytoplasm by an inhibitory protein IκBα, which masks the conserved nuclear localization sequence (NLS) on RelA/p65 to prevent nuclear translocation. Upon stimulation, IκBα undergoes phosphorylation, polyubiquitination and proteasome-mediated degradation, and eventually releases the NF-κB dimers to the nucleus. Nuclear-translocated NF-κB dimers up- or down-regulates target gene expression by binding to the κB enhancer or promoter elements. Inducers of NF-κB activity include pro-inflammatory cytokines, including tumor necrosis factor α (TNF-α), interleukin-1 (IL-1), lipopolysaccharide (LPS), T-cell receptor (TCR) ligands and genotoxic and oxidative stress.

NF-κB activation is regulated by the IκB kinase (IKK) complex, comprised of two identified catalytic subunits, IKKα and IKKβ, and a regulatory subunit NEMO/IKKγ. The domains in IKKα and IKKβ, required for the assembly of IKK complexes by facilitating association with the α-helical region in N-terminus of NEMO, reside in the C-termini. An 11 amino acid peptide derived from the NEMO binding domain (NBD) of IKKβ, amino acids 735-745, is able to disrupt the association of IKKβ and NEMO and reduced NF-kB activation when fused to a protein transduction domain (PTD) for intracellular delivery.

The NBD peptide has strong therapeutic effects in various inflammatory disease models in mice and other species. Chronic, systemic administration of NBD peptide attenuates macrophage-mediated muscle necrosis and degeneration in mdx mice, a murine model of Duchenne muscular dystrophy (DMD), as well as in the golden retriever muscular dystrophy (GRMD) canine model of DMD. Similarly, the NBD peptide ameliorates active chronic colitis in IL-10-deficient mice without affecting NF-κB basal activity when administered systemically.

Intra-articular injection of NBD peptide also attenuates synovial inflammation and the severity of arthritis in a rat model of adjuvant arthritis. It also ameliorates inflammation-induced osteoclastogenesis and arthritis by downregulating NF-κB target genes, TNF-α and IL-1β. Moreover, systemic delivery of the NBD peptide reduces the severity of Parkinson's disease by suppressing nigral microglial activation and reducing dopaminergic neuronal loss as well as alleviates nephropathy and atherosclerosis in Type 1 diabetic mice. In addition, the peptide prevents an LPS-induced pulmonary inflammation in sheep and improves pulmonary function in a piglet model of acute respiratory distress syndrome by topical administration. Also, clinical testing of the NBD peptide for local treatment of canine diffuse large B-cell lymphoma revealed a reduction in the proliferation of malignant B cells.

Despite these strong and varied therapeutic effects of PTD-NBD peptides in animal models, the expense of peptide synthesis, the short half-life of the peptide and its lack of oral bioavailability limit its clinical use. Thus the goal of this study was to develop small molecules that mimic the NBD peptide, targeting the NEMO binding domain of IKK to disrupt its binding to NEMO. A structure-based pharmacophore model that mimics these interactions was first derived using the crystal structure of the IKK complex, followed by a virtual screening using this model against commercially available databases of drug-like molecules. The resulting hits were prioritized using in-silico ADME/Toxicity filtering, and molecular-docking, to determine the higher affinity hits. The best candidate molecules were purchased, tested experimentally, and helped us identify novel NBD mimetics. Following multiple rounds of optimization, several compounds were demonstrated to significantly inhibit LPS- and TNFα-induced NF-κB activation by disrupting the association between IKKβ and NEMO. In addition, these compounds exhibited potent therapeutic effects in murine models of LPS-induced endotoxemia and Duchenne muscular dystrophy, suggesting their potential as therapeutic drugs for clinical management of diseases driven by IKK/NF-κB activation.

We have used pharmacophore modeling and virtual screening techniques to identify possible small molecules that mimic the NBD peptide, blocking the interaction between IKKβ and NEMO. Our hypothesis was that small molecules that inhibit the binding NEMO to IKK$_β$ can be identified using the existing information about the interactions between the two proteins. We have developed a structure-based pharmacophore model that mimics these interactions, followed by a virtual screening using this model against commercially available databases of drug-like molecules. The resulting hits were prioritized using computational, in-silico ADME/Toxicity filtering, and molecular-docking, to determine the higher affinity hits. Compounds that emerged were proposed for biological testing.

The diagram shown in FIG. 1 represents the overall strategy used in identification of library compounds useful for carrying out methods of the invention. A pharmacophore model, described in greater detail below, was generated, refined, and used to screen the population of a virtual structural database, ZINC 8.0. Lead hits with good scores in the pharmacophore model were selected and further screened computationally with respect to predicted properties related to absorption, distribution, metabolism, excretion, and toxicity (ADMET) in mammals.

Pharmacophore Model Generation

Figure 2:
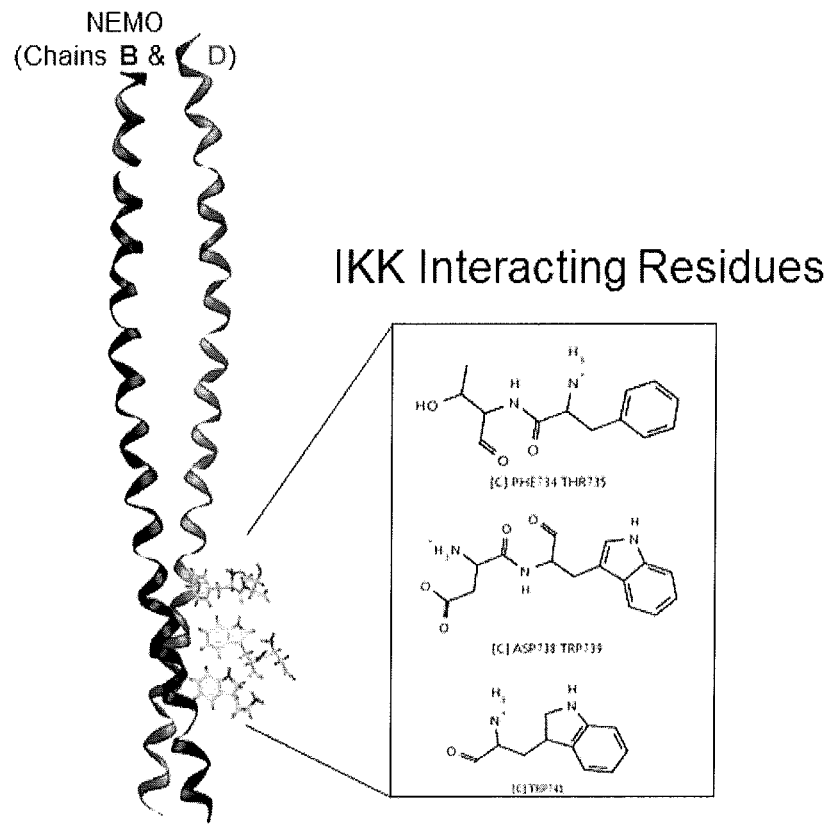
FIG. 2 depicts IKK amino acid residues at the NEMO binding domain, derived using the LigandScout Software (Inte:Ligand).

A structure-based pharmacophore model, shown in FIG. 2, was derived from the interactions between NEMO/IKK$_β$ using the LigandScout Software (Inte:Ligand) (http://www.inteligand.com/ligandscout/).

Figure 3:
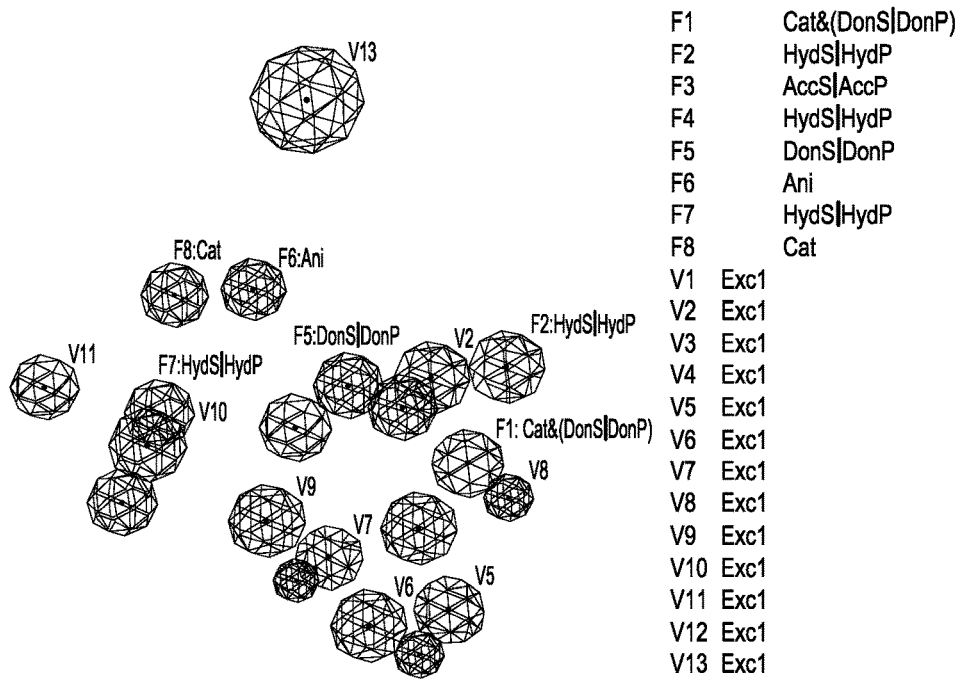
FIG. 3 shows the pharmacophore model used in identification of structures for blocking the interaction between NF-κB essential modulator ("NEMO") with IκB kinase-β (IKK-β) at the NEMO binding domain (NBD).

Each interacting atom from each residue was "translated" into a pharmacophoric feature, resulting in the structure-based pharmacophore shown in FIG. 3. The pharmacophore model consists of eight features (F1, . . . , F8) and 13 exclusion volumes represented by the meshed black spheres, which represent important atoms from the protein's environment.

Figure 4:
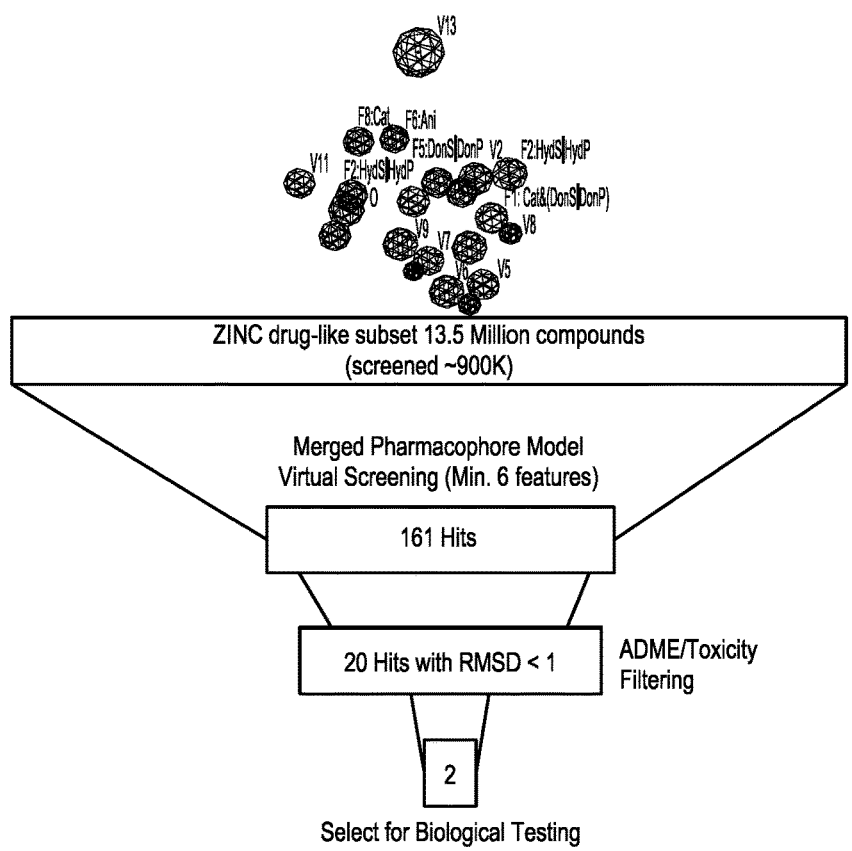
FIG. 4 is a graphical depiction of the results obtained from the screening process.

This model was used to screen a subset of the drug-like ZINC 8.0 database set (~900,000 compounds) (Irwin et al., 2005). We were able to identify 161 hits that matched at least 6 features out of eight of the pharmacophore model. Twenty hits had an RMSD<1, and were further prioritized using Absorption, Distribution, Metabolism, Excretion, and Toxicity (ADME/Tox) predicted properties. Two compounds termed NBDA-1 (Zinc-13) and NBDA-2 (Zinc-5), successfully passed these filters (See FIG. 4) and were purchased for biological testing. The compounds were then tested for ability to inhibit TNF-alpha-mediated induction of NF-κB activity in a 293 cells stably modified with a NF-κB luciferase reporter.

One compound, termed Zinc-13 (FIG. 5) was able to reduce activation of NF-κB by TNF-alpha at low micromolar ranges. We also demonstrated that the compound reduced phosphorylation of IkB, the key target for IKK, suggesting that it was able to block IKK activity. In addition, we have demonstrated the ability of the compound to disrupt the interaction between IKKβ and IKKgamma in vivo by coimmunoprecipitation. The next step was to search for structural analogs. The method used for analog identification was the morphological similarity, a similarity technique dependent only on surface shape and charge characteristics of ligands.

Morphological similarity is defined as a Gaussian function of the differences in the molecular surface distances of two molecules at weighted observation points on a uniform grid. The computed surface distances include both distances to the nearest atomic surface and distances to donor and acceptor surfaces. This function is dependent on the relative alignment of the molecules, and consequently their alignment and conformation must be optimized. The conformational optimization problem is solved by fragmentation, conformational search, alignment, and scoring, followed by incremental reconstruction from high-scoring aligned fragments. The alignment problem is addressed by exploiting the fact that two unaligned molecules or molecular fragments that have some degree of similarity will have some corresponding set of observers that are seeing the same things. Optimization of the similarity of two unaligned molecules or molecular fragments is performed by finding similar sets of observers of each molecule that form triangles of the same size.

Figure 5:
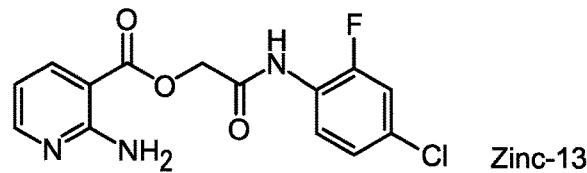
FIG. 5 depicts the structure of the compound termed NBDA-1 (Zinc-13), identified from the ZINC virtual database using the pharmacophore model of the invention; an exemplary compound of formula (IB).
Figure 6:
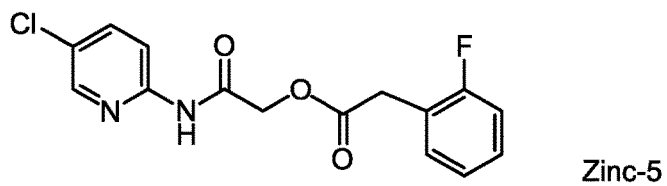
FIG. 6 depicts the structure of the compound termed NBDA-2 (Zinc-5), identified from the ZINC virtual database using the pharmacophore model of the invention, an exemplary compound of formula (IA).
Figure 11:
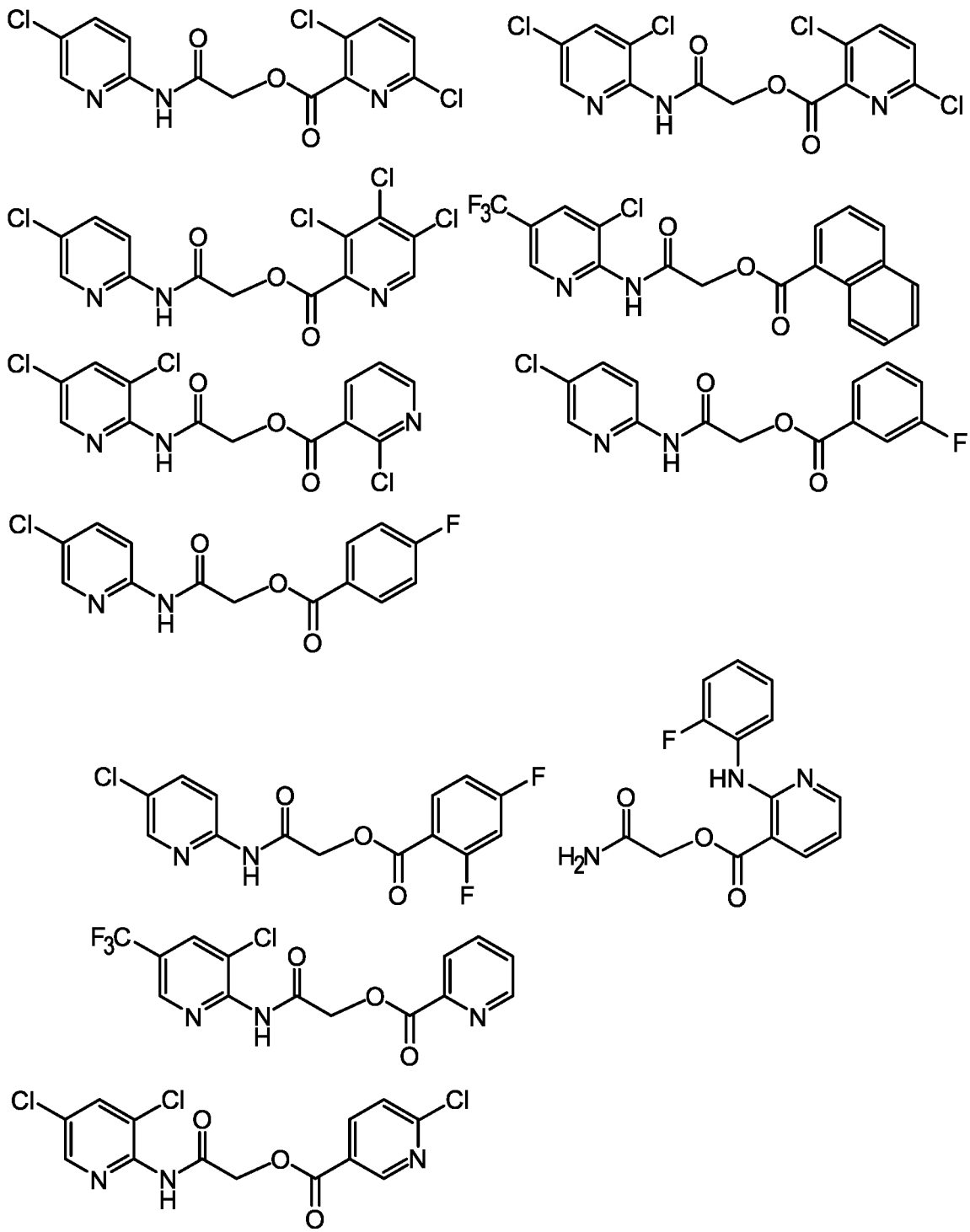
FIG. 11 shows compounds from the ZINC 8.0 database, acquired and tested biologically, indicated to less effective in inhibition of TNFα relative to NBDA-1 (Zinc-13) and NBDA-2 (Zinc-5).

Fifteen analogs with a similarity score>90% were identified using this technique, and all were acquired for experimental testing. Of the 15 compounds tested, at least one additional compound (Zinc-5) was able to inhibit TNF-alpha mediated activation of NF-κB, as or more efficiently as the NBD peptide. FIG. 5 depicts the structure of the compound termed NBDA-1 (Zinc-13), identified from the ZINC virtual database using the pharmacophore model of the invention; an exemplary compound of formula (IB); FIG. 6 depicts the structure of the compound termed NBDA-2 (Zinc-5), identified from the ZINC virtual database using the pharmacophore model of the invention, an exemplary compound of formula (IA). The 13 inactive compounds from among these 15 are shown in FIG. 11.

Figure 7:
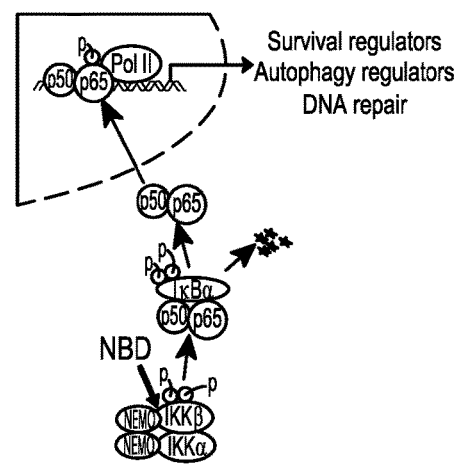
FIG. 7 shows known inhibitory peptides of NEMO.

FIG. 7 shows known inhibitory peptides of NEMO that were used in developing the pharmacophore model used for the screening program.

Figure 8:
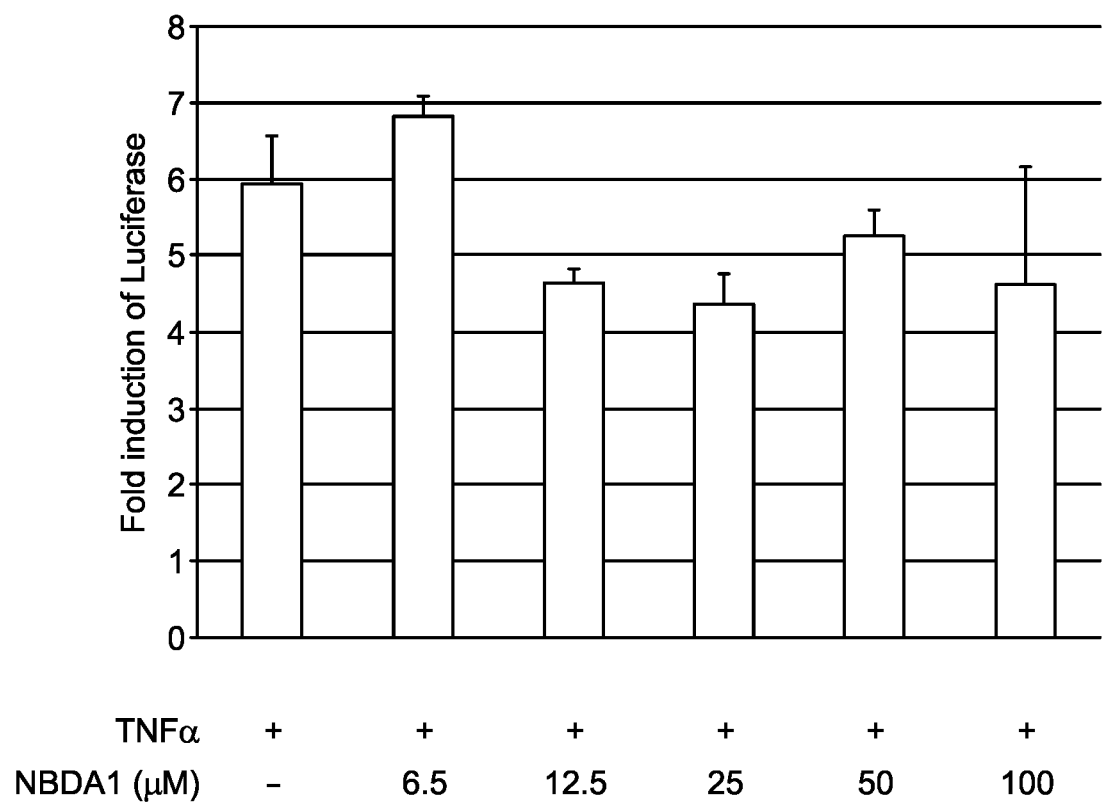
FIG. 8 is a bar graph showing the inhibition of TNFα by various levels of NBDA-1 (Zinc-13).
Figure 9:
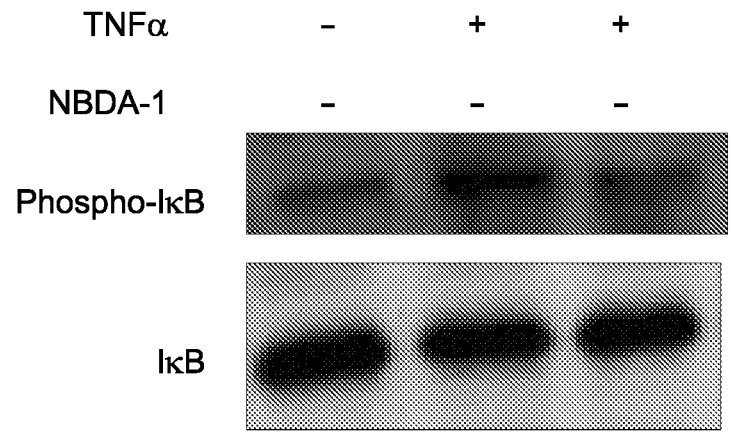
FIG. 9 is an image of a Western blot of immunoprecipitated IKKβ, analyzed for the level of co-precipitated NEMO, showing the inhibition of TNFα by NBDA-1 (Zinc-13).

FIG. 8 is a bar graph showing the inhibition of TNFα by NBDA-1 (Zinc-13). In FIG. 8, NBDA-1 treatment also reduces the level of phospho-IκB. In addition, we have examined the ability of the compounds to disrupt the IKK complex, comprised of IKKβ, IKKα and NEMO. At 1 and 4 hours post-treatment of 293 cells with Zinc-5, Zinc-13 or NBD, IKKβ was immunoprecipitated and analyzed by Western blot for the level of co-precipitated NEMO; FIG. 9 shows an image of the Western blot.

Figure 10:
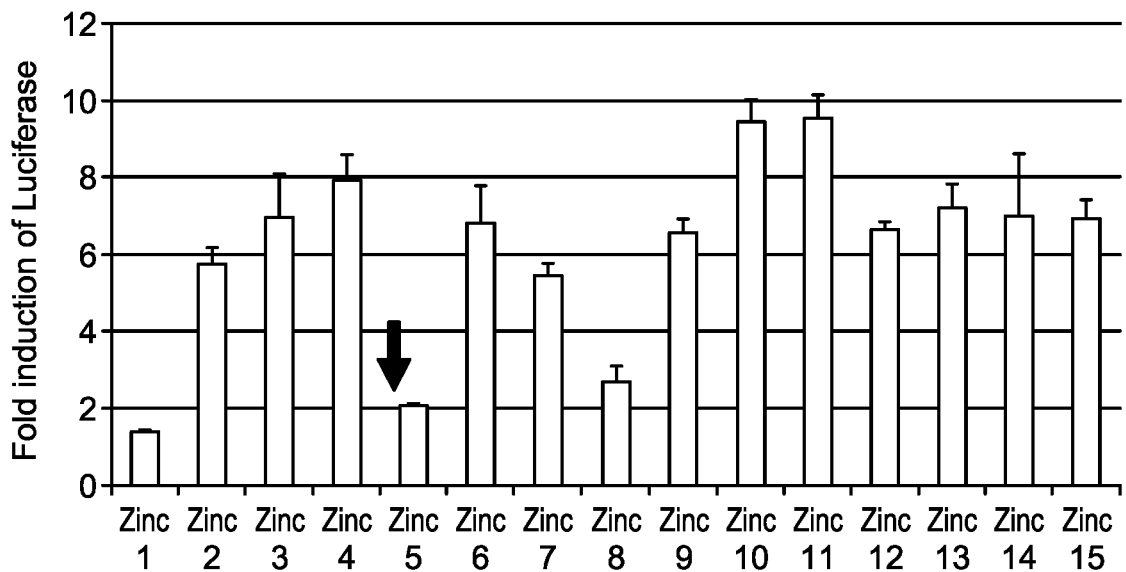
FIG. 10 is a bar graph showing the results of a luciferase assay of NF-κB-luciferase reporter transfected 293 cells treated with Zinc compounds.

The ability of NBDA-1 (Zinc-13) to inhibit NF-κB activity was demonstrated by treating 293-NF-kB-luciferase reporter cells with the compound followed by addition of TNF to induce NF-κB. The activation of NF-κB was then quantitated by measuring the level of luciferase activity. FIG. 10 similarly shows the ability of NBDA-2 (Zinc-5) to inhibit NF-κB activity in 293-NF-κB-luciferase reporter cells effectively. Also, protein extracts were prepared from the same cells and the level of phospho-IkB determined, a marker of IKK activity.

Figure 12:
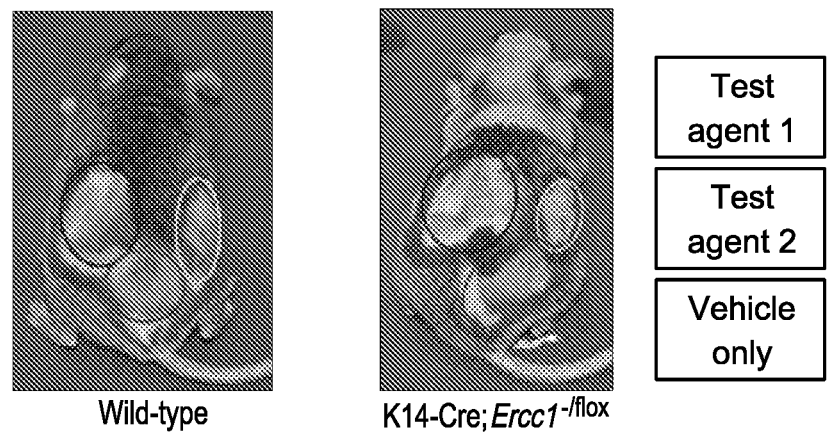
FIG. 12 shows the results of topically treating a wild type and K14-Cre; Ercc1 mouse with NBDA-1 (Test Agent 1), the 8K-NBD peptide (Test Agent 2), and a control.
Figure 14:
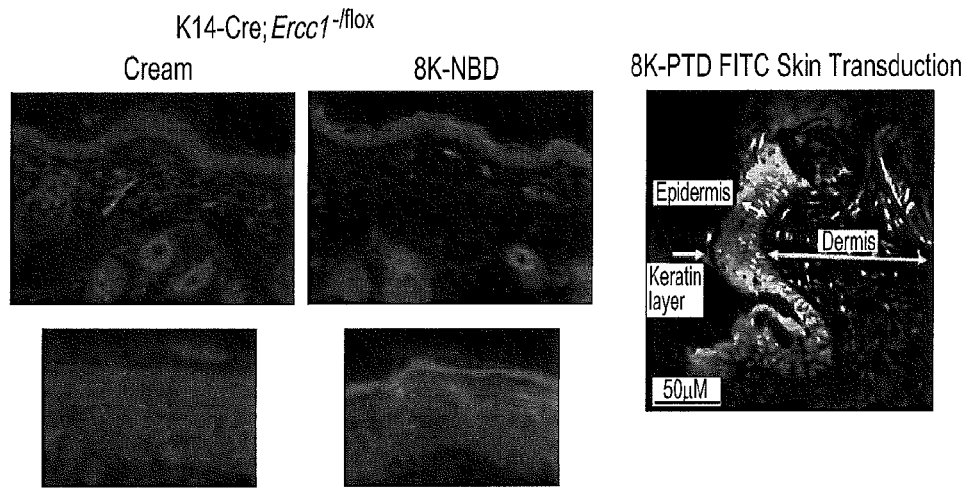
FIG. 14 is a photomicrograph showing thickening of the epidermis in mice treated with the 8K-NBD peptide.
Figure 15:
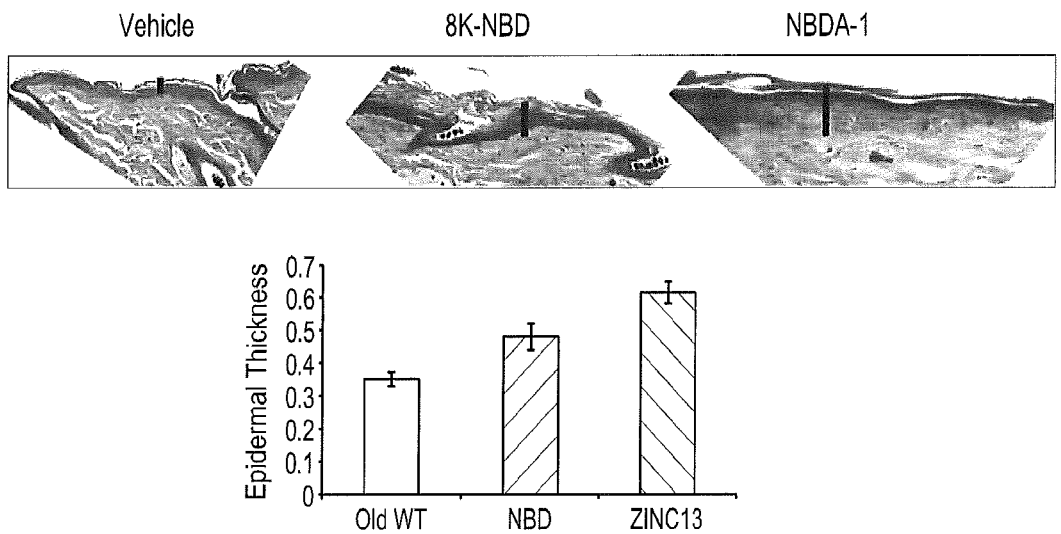
FIG. 15 shows a tissue cross section photograph indicating thickening of the Epidermis in mice treated with NBDA-1 versus 8K-NBD peptide and a control, and a bar graph showing the measured thickness of the Epidermis in mice treated with NBDA-1 versus 8K-NBD peptide and a control.

To test the ability of NBDA-1 to function in vivo, the drug was tested in several models of aging. In FIG. 12, the ability of topical treatment of NBDA-1 to reduce signs of skin aging is shown. Areas on the back of normal mice or mice with enhanced skin aging (K14-Cre; Ercc1$^{-/flox}$) were shaved and then treated daily with drugs or control creams. As shown in FIG. 14, treatment with the 8K-NBD peptide (FIG. 7) showed improved skin architecture and increased epidermal thickness. Interestingly, treatment with NBDA-1 resulted in improved epidermal thickness to a greater extent than the peptide on which it was modeled (FIG. 15).

Figure 13:
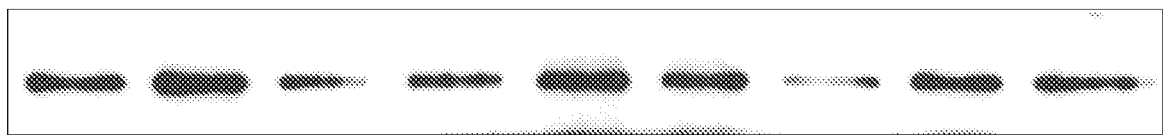
FIG. 13 shows data supporting that NBDA-1 and NBDA-2 are able to disrupt the IKK/β-NEMO interaction in vivo as demonstrated by co-immunoprecipitation.

As shown in FIG. 13, treatment with Zinc-5 reduced the level of co-immunoprecipitated NEMO at 4 hours, Zinc-13 at 1 hour and the control NBD peptide at 4 hours. A non-functional, related compound Zinc-7 had no effect. These results suggest that the NBDA (Zinc) compounds are working similarly to the NBD peptide to disrupt the IKK complex.

Figure 16:
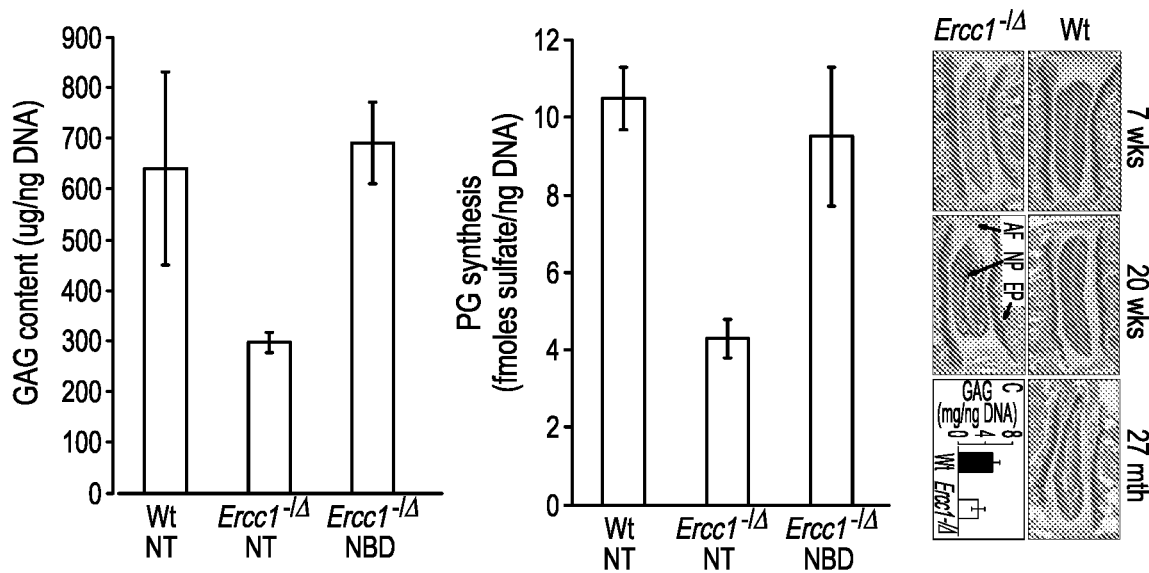
FIG. 16 provides bar graphs and photomicrographs showing the increase in proteoglycans in the intervertebral disc of Ercc1$^{-/\Delta}$ mice treated chronically (3× per week for 10 weeks) i.p. with 10 mg/kg 8K-NBD.
Figure 17:
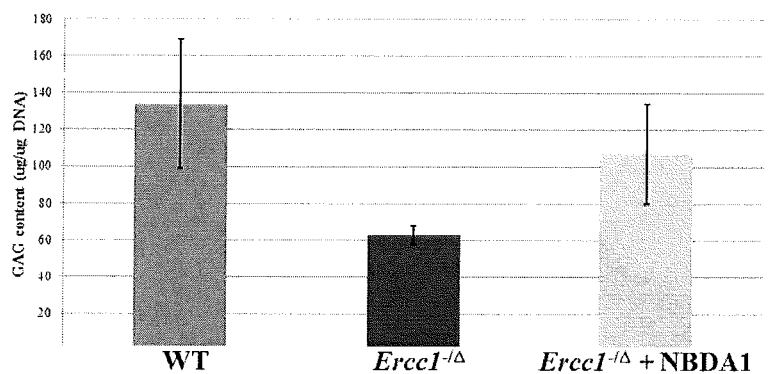
FIG. 17 shows data supporting that treating Ercc1$^{-/\Delta}$ mice with NBDA-1 3× per week with 2 mg/kg i.p. for 8 weeks improves proteoglycan synthesis in the intervertebral disc.

The ability of the compounds to work systemically was also tested. In these experiments, Ercc1$^{-/\Delta}$ mice with accelerated aging (lifespan of 5 months) were treated systemically, 3× a week, by IP injection at a dose of 10 mg/kg for 8 weeks. Since we previously had shown that the NF-κB is a key factor in driving intervertebral disc degenerated, we assessed the effects of treatment on proteoglycan synthesis and content in the discus following treatment. As shown in FIGS. 16 and 17, treatment with the 8K-NBD peptide restored proteoglycan synthesis and content back to levels seen in normal, young mice. Similarly, NBDA-1 treatment increased the proteoglycan content in the Ercc1$^{-/\Delta}$ mice.

Figure 18:
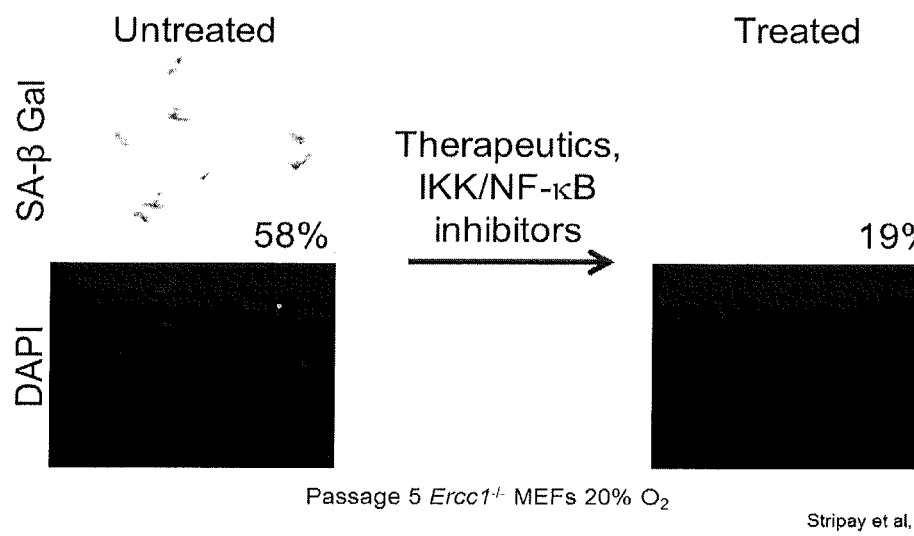
FIG. 18 shows photomicrographs supporting that an increase in senescence, as measured by SA-ß-gal in embryonic fibroblasts from Ercc1$^{-/-}$ mice grown under oxidative stress conditions (20% $O_2$), can be rescued with drug treatment.
Figure 19:
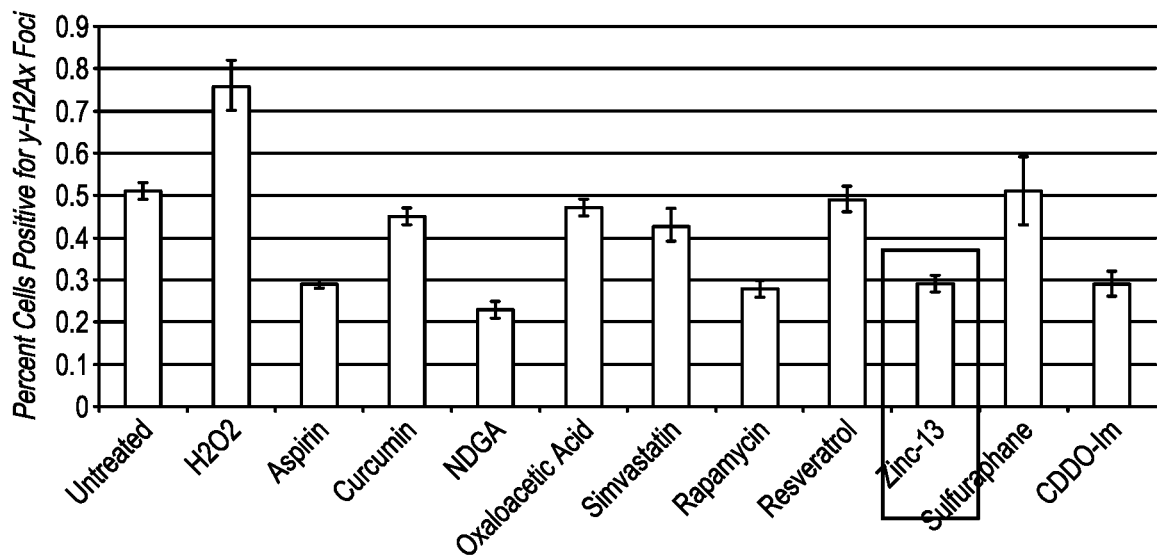
FIG. 19 is a bar graph showing the ability of drugs known to have anti-aging effects in naturally aged mice (rapamycin, NDGA and aspirin), and NBDA-1, to reverse senescence in ERCC1-deficient mouse fibroblasts grown under oxidative stress conditions.

In an attempt to identify new drugs able to improve healthspan, we have developed an assay for screening for drugs able to rescue primary "aged" fibroblasts from senescence. This assay uses murine embryonic fibroblasts (MEFs) from mice with accelerated aging due to a deficiency in an important DNA repair pathway, ERCC1-XPF. These MEFs undergo rapid senescence in culture, especially when grown under the high oxygen conditions that confers oxidative stress (FIGS. 18 and 19). Treatment of the senescent cells with certain drugs resulted in reversal in senescence in the majority of the cells (measure by SA-ß-gal staining), stimulation of proliferation and reduction in gamma-H2AX foci with 24 hours. Initial analysis of a panel of agents in this assay identified rapamycin, aspirin and NDGA as the most effective for rescuing senescence, identical to the results from years of screening for effects on aging in naturally aged, wt normal mice. Similarly, Zinc-13, also reduced senescence (FIGS. 18 and 19), similar to the ability of other IKK inhibitors.

Figure 20:
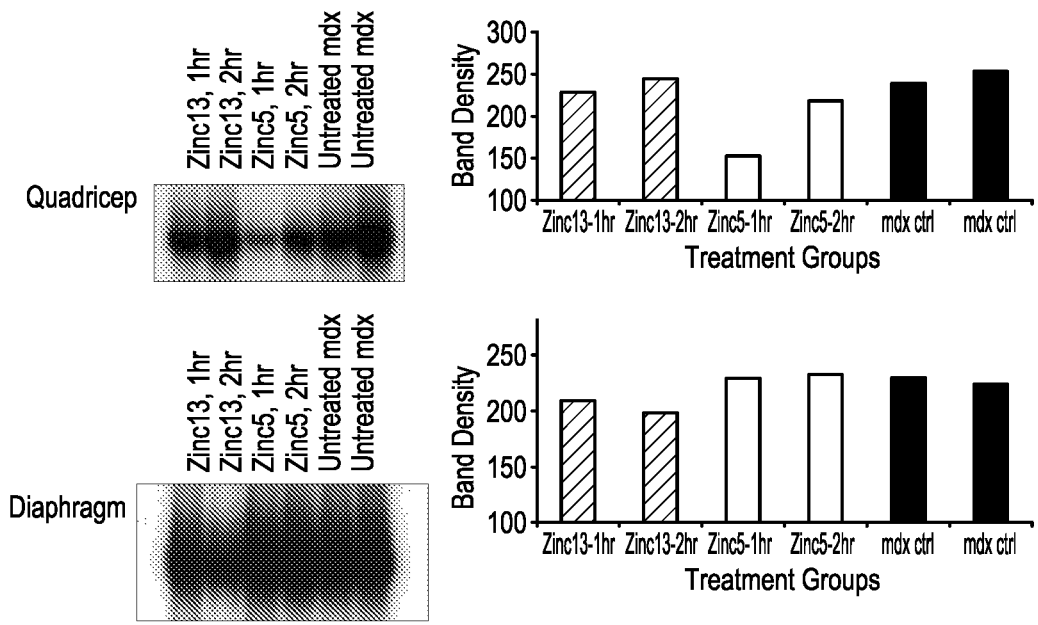
FIG. 20 shows data concerning the reduction of DNA binding activity of NF-κB in mdx mice, a mouse model of muscular dystrophy, at 1 and 2 hours post-treatment with NBDA-1 and NBDA-2.
Figure 21:
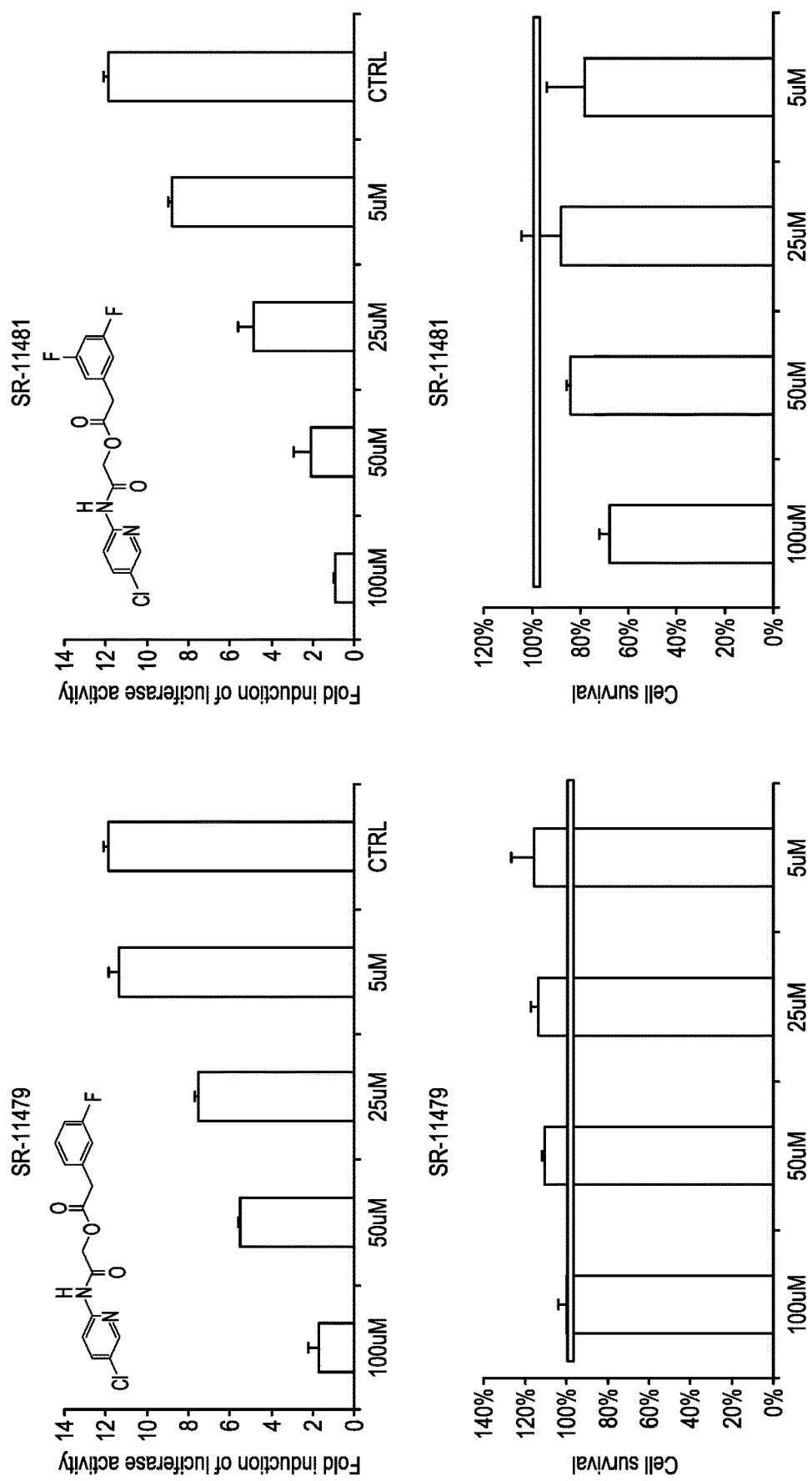
FIG. 21 shows data related to inhibition of NF-κB activity, and toxicity, treating 293-NF-κB-luciferase reporter cells with the compounds SRI 1479 and SRI 1480, followed by addition of TNF to induce NF-κB. See Table 1 for structures.
Figure 22:
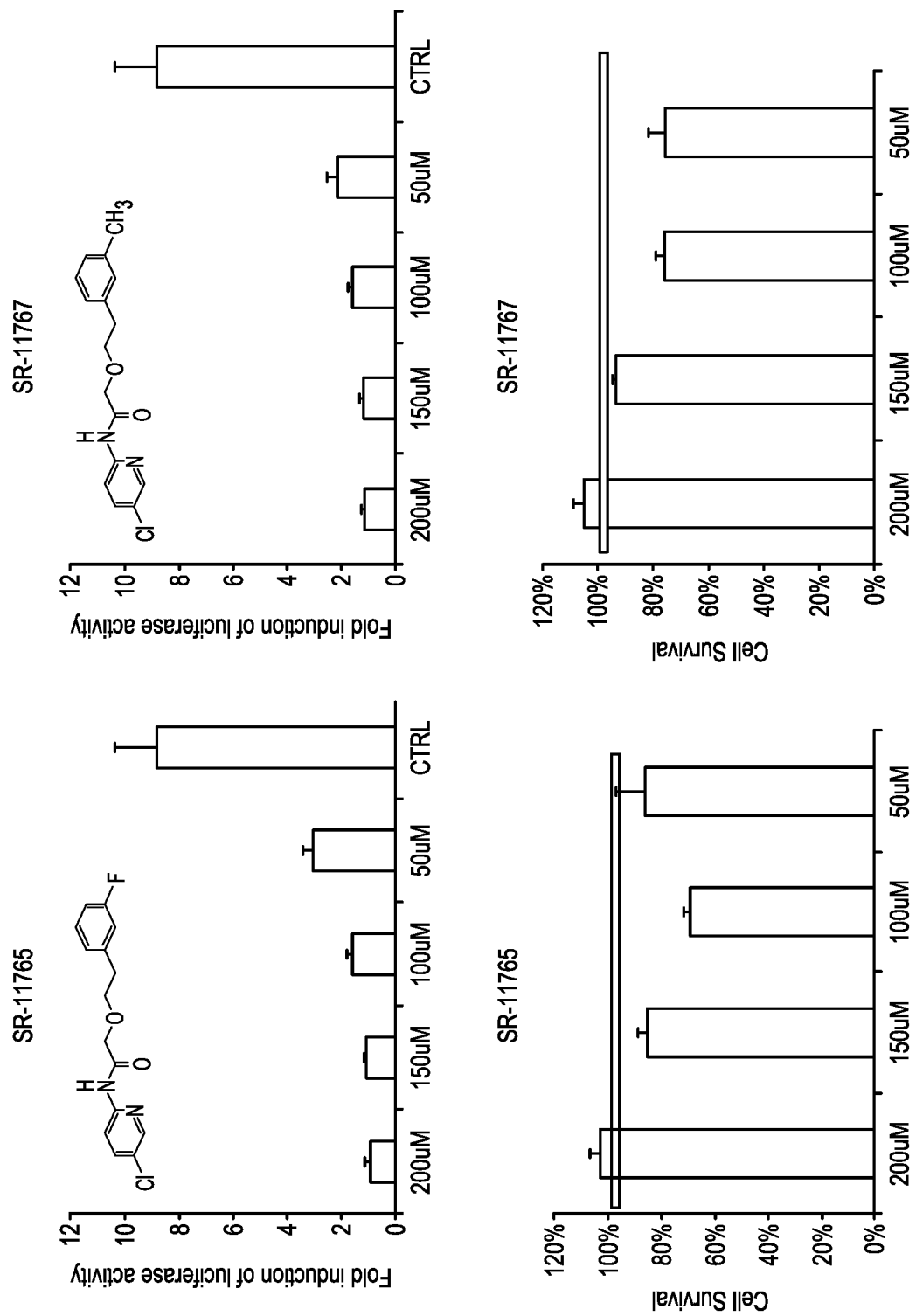
FIG. 22 shows data related to inhibition of NF-κB activity, and toxicity, treating 293-NF-κB-luciferase reporter cells with the compounds SR11765 and SR11767, followed by addition of TNF to induce NF-κB. See Table 1 for structures.
Figure 23:
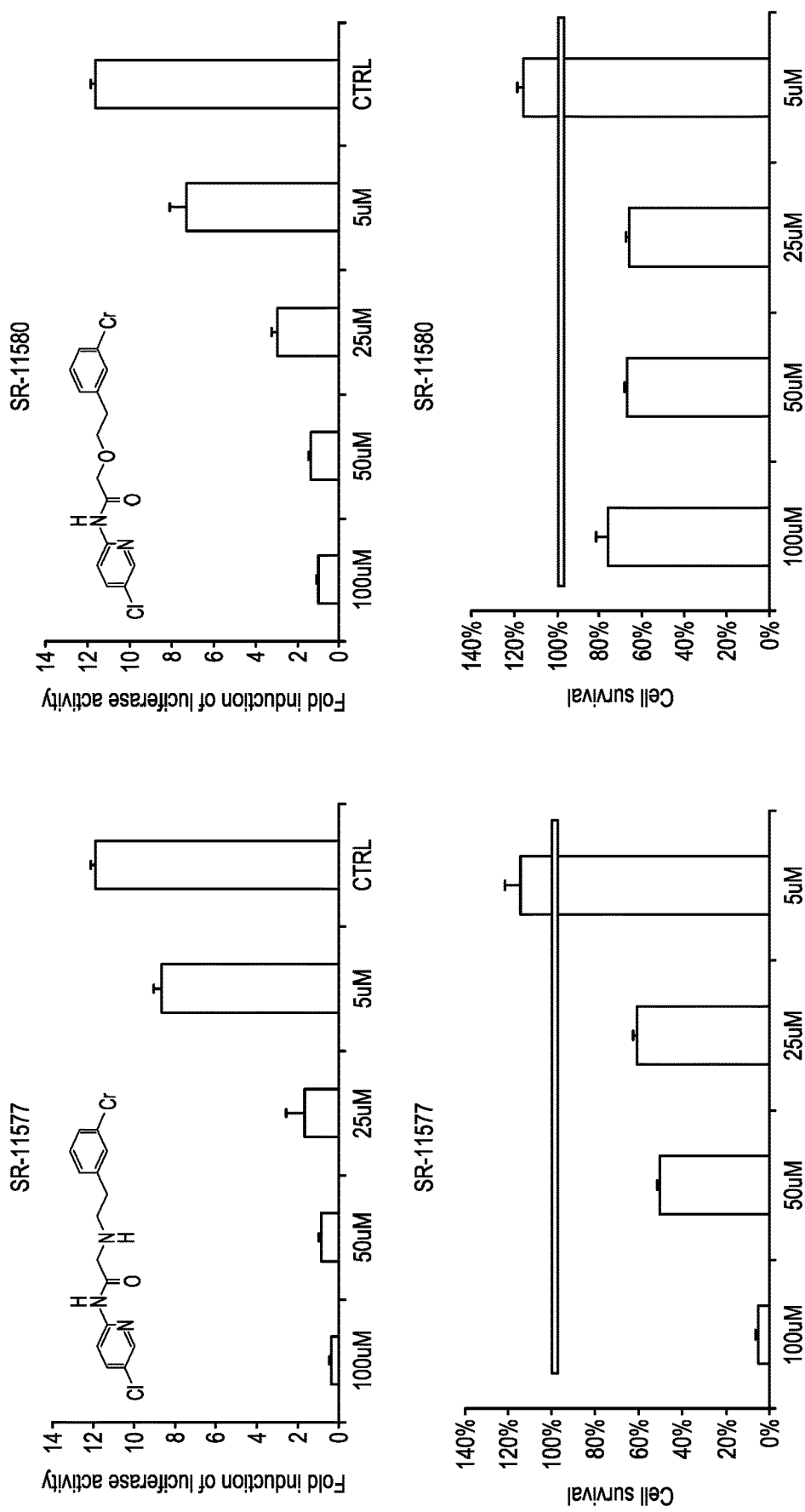
FIG. 23 shows data related to inhibition of NF-κB activity, and toxicity, treating 293-NF-κB-luciferase reporter cells with the compounds SR11577 and SR11580, followed by addition of TNF to induce NF-κB. See Table 1 for structures.
Figure 24:
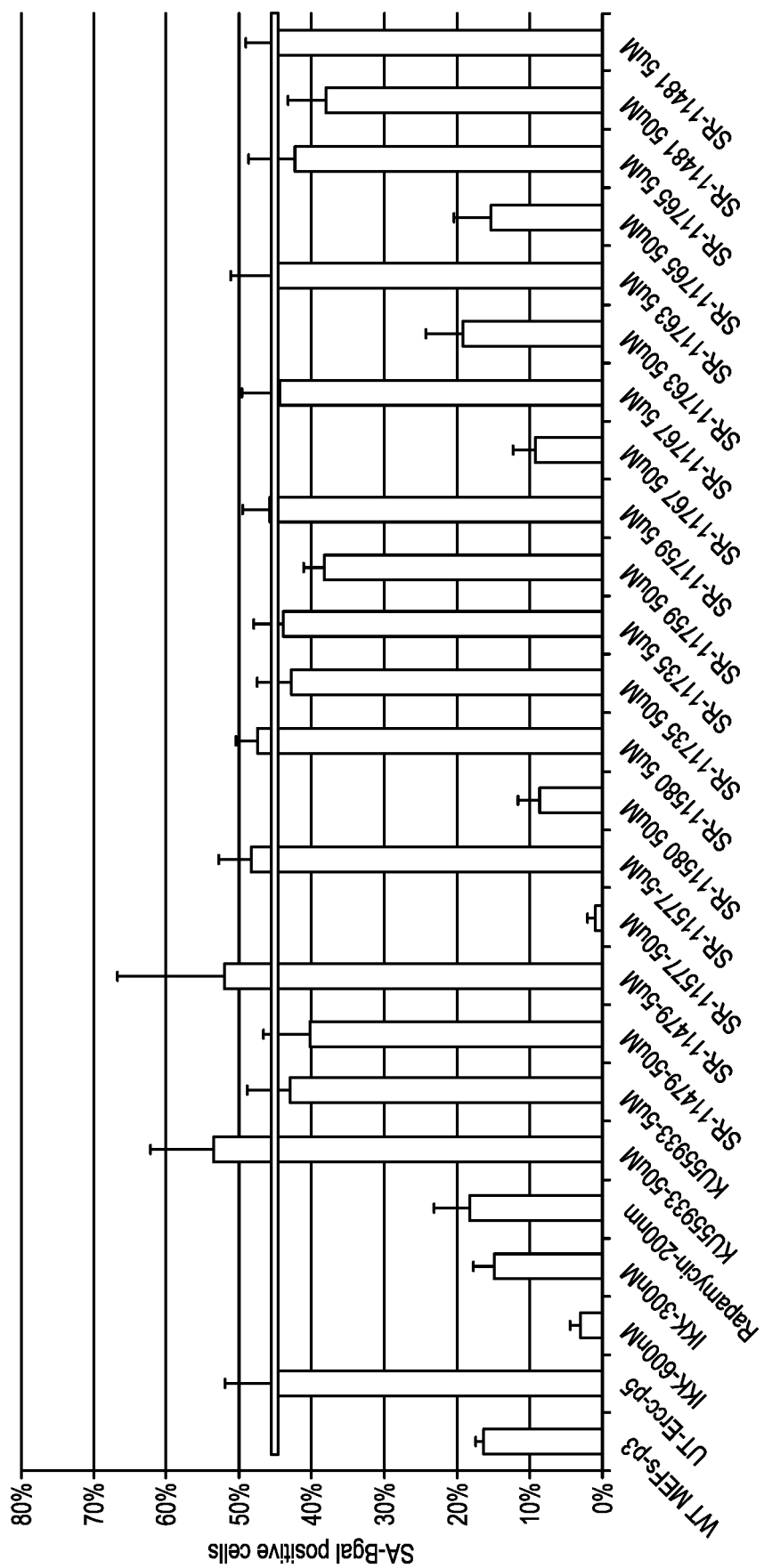
FIG. 24 shows the effect on Mouse Embryonic Fibroblasts of compounds of the invention and controls on SA-ß-gal activity in embryonic fibroblasts from Ercc1$^{-/-}$ mice maintained under oxidative stress conditions.
Figure 25:
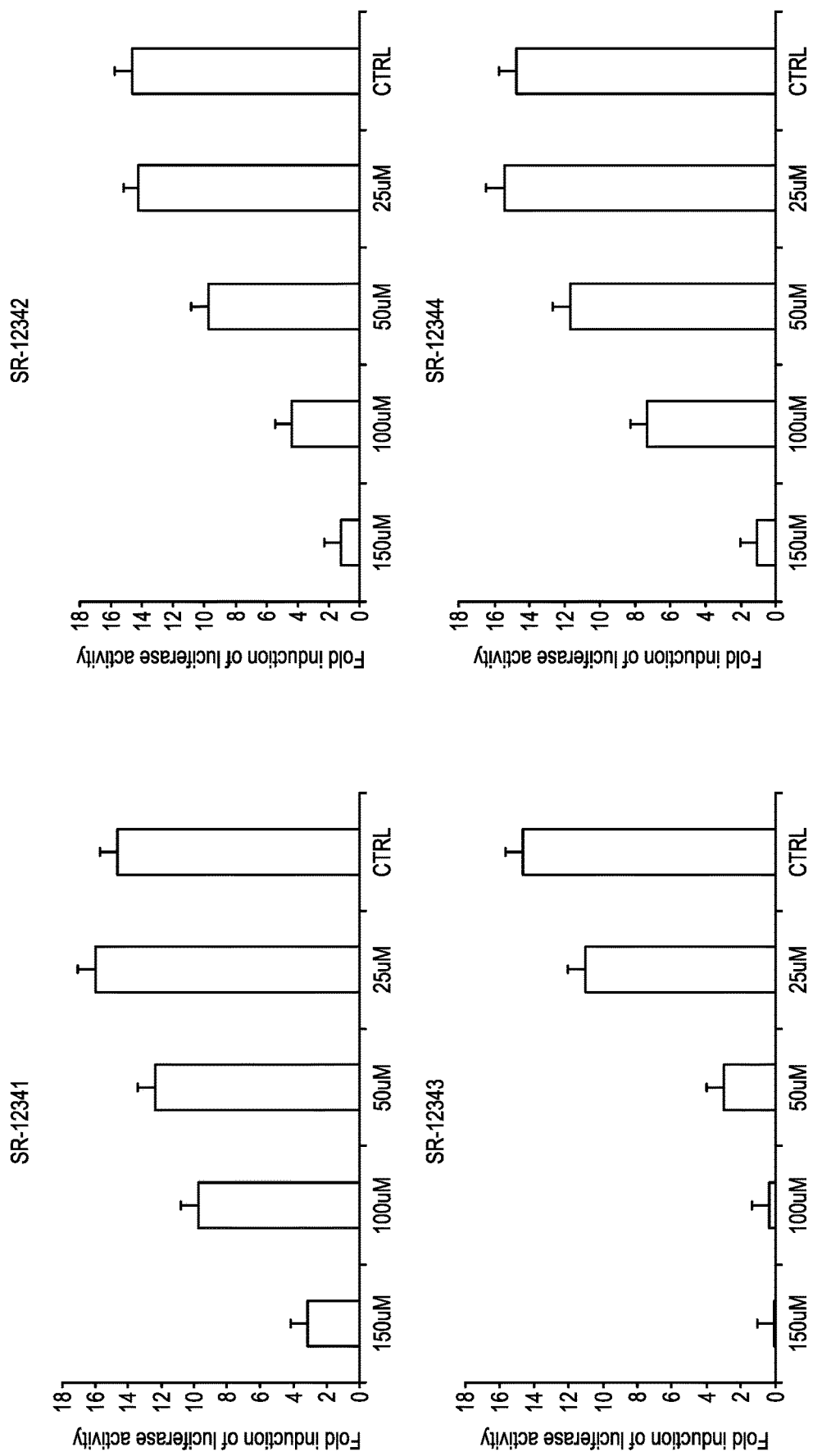
FIG. 25 shows data related to inhibition of NF-κB activity, treating 293-NF-κB-luciferase reporter cells with the compounds SR12341, SR12342, SR12343, and SR12344, followed by addition of TNF to induce NF-κB. See Table 1 for structures.
Figure 26:
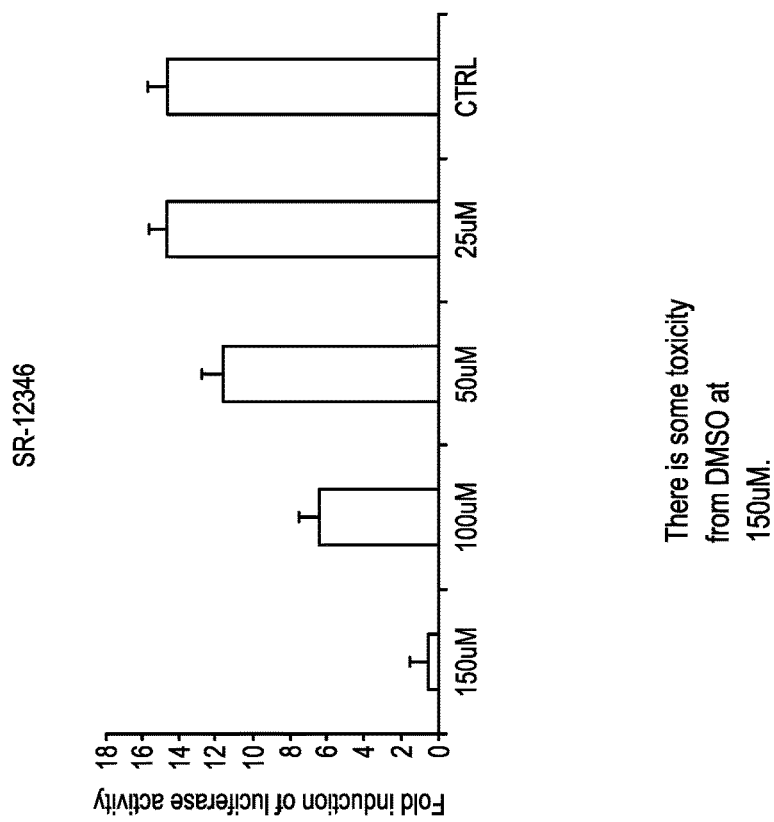
FIG. 26 shows data related to inhibition of NF-κB activity, treating 293-NF-κB-luciferase reporter cells with the compounds SR12345, SR12346, and SR12347, followed by addition of TNF to induce NF-κB. See Table 1 for structures.
Figure 26:
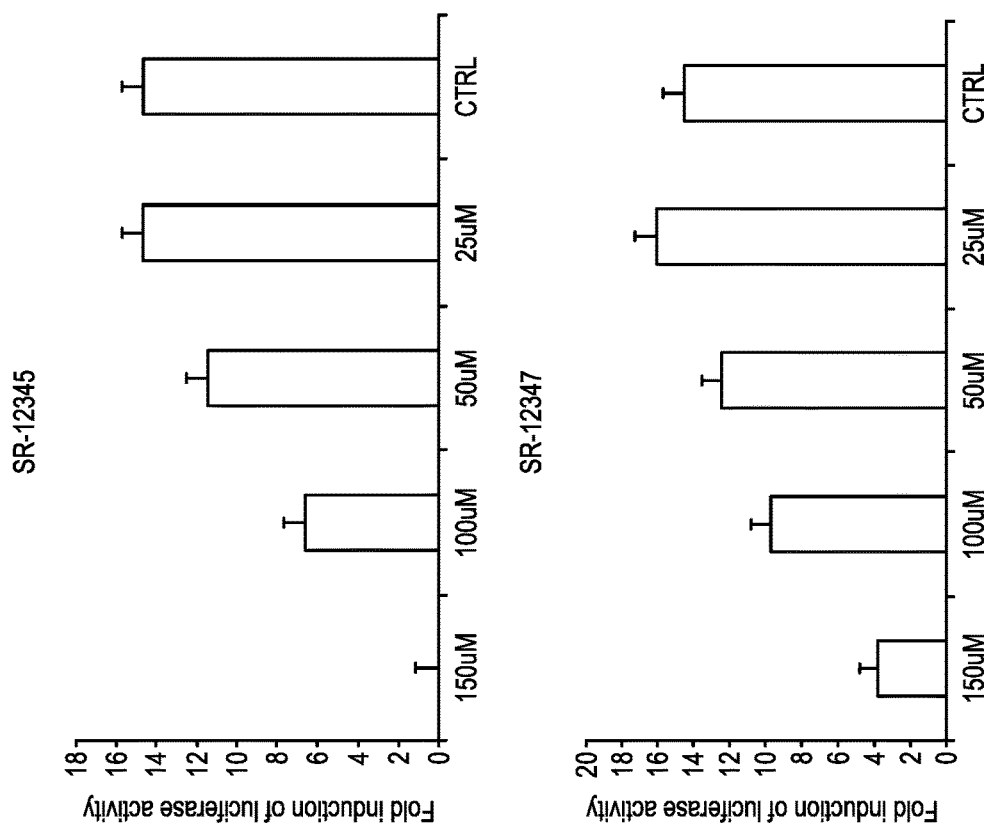
Figure 27:
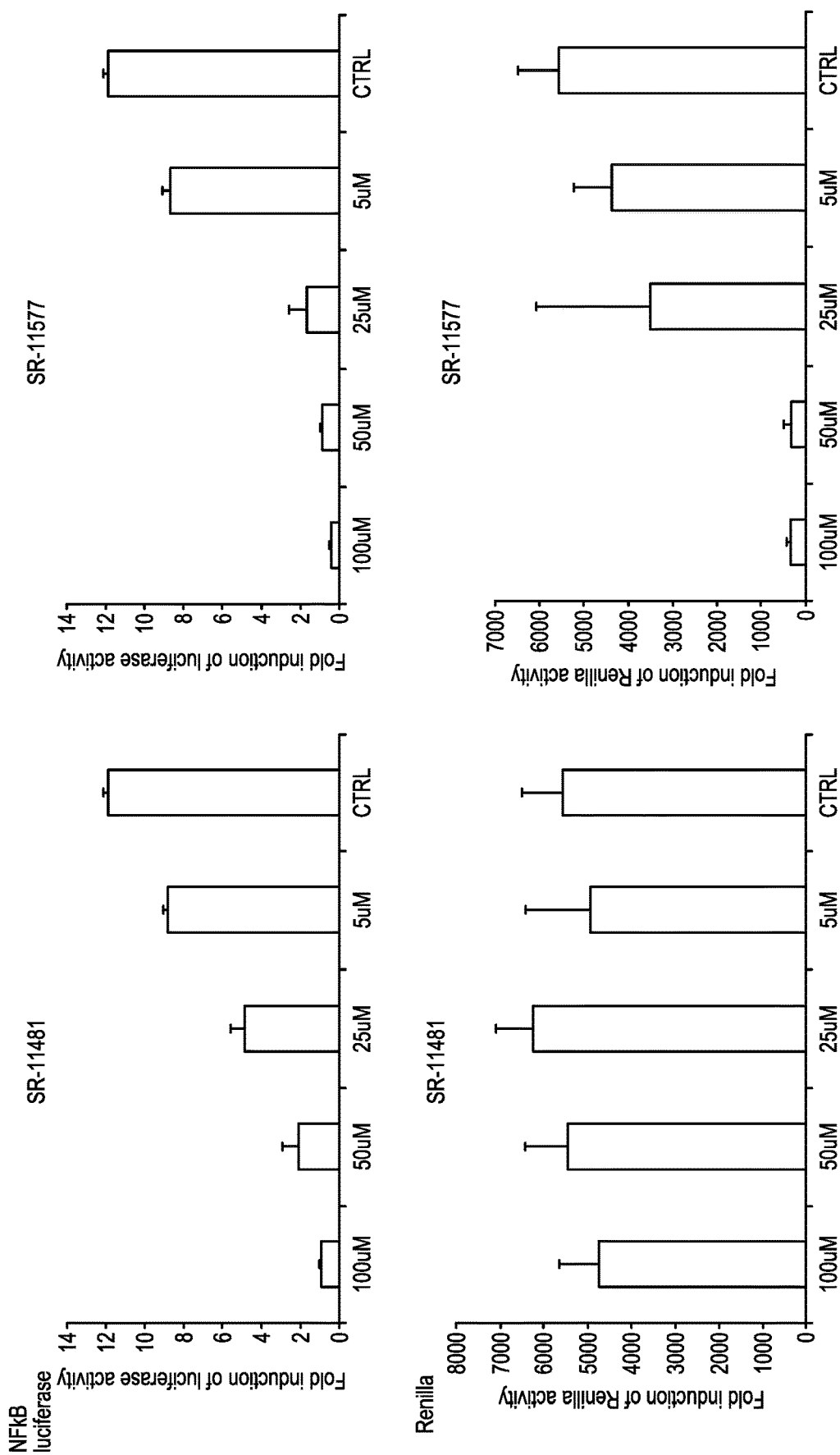
FIG. 27 shows data related to inhibition of NF-κB activity, treating 293-NF-κB-luciferase reporter cells with the compounds SR11481 and SR11577, followed by addition of TNF to induce NF-κB. Any reduction in the level of renilla, expressed from a constitutive promoter, expression indicates toxicity. See Table 1 for structures.
Figure 28:
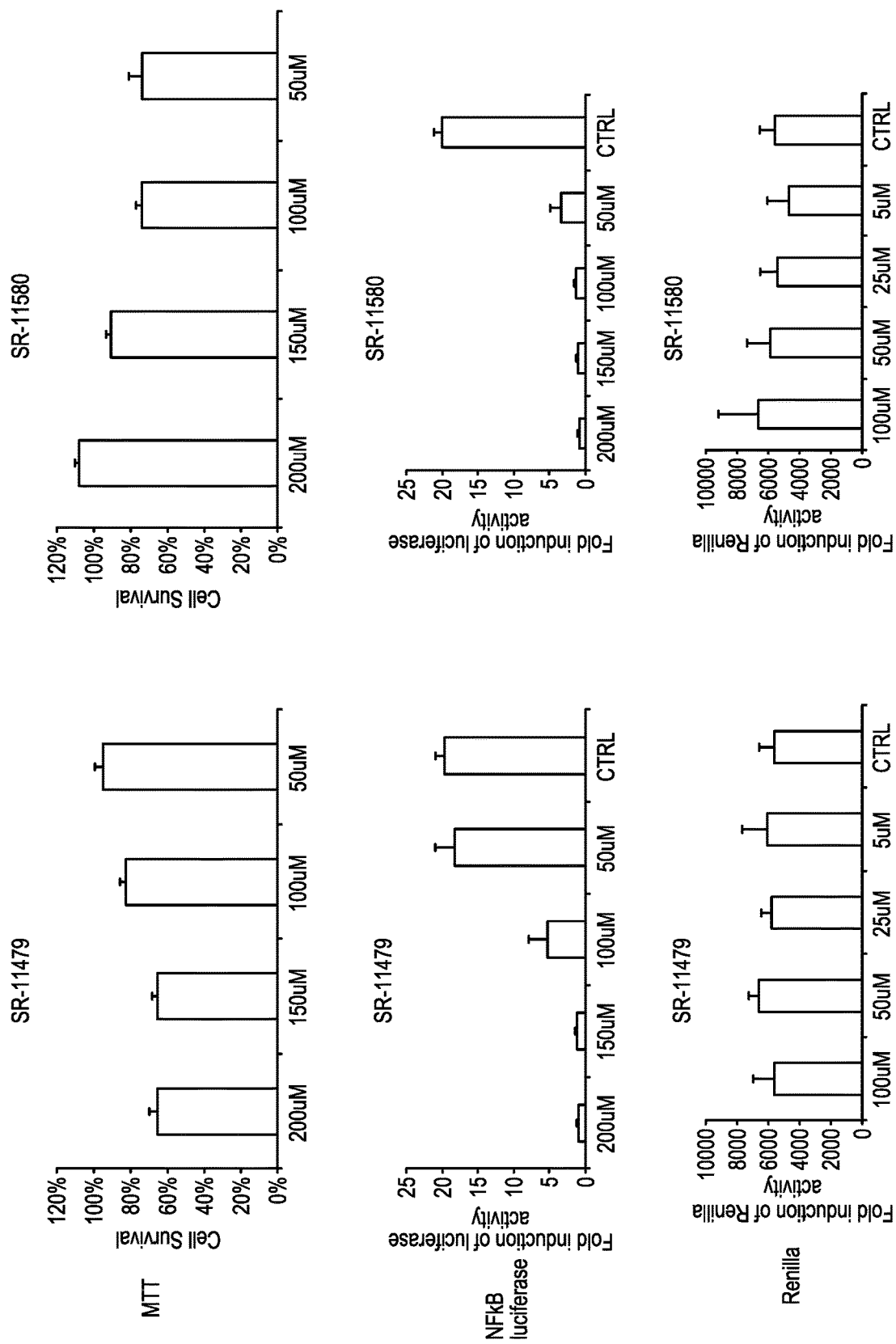
FIG. 28 shows data related to inhibition of NF-κB activity, treating 293-NF-κB-luciferase reporter cells with the compounds SR11479 and SR11580, followed by addition of TNF to induce NF-κB. A reduction in renilla expression or MTT indicates toxicity.
Figure 29:
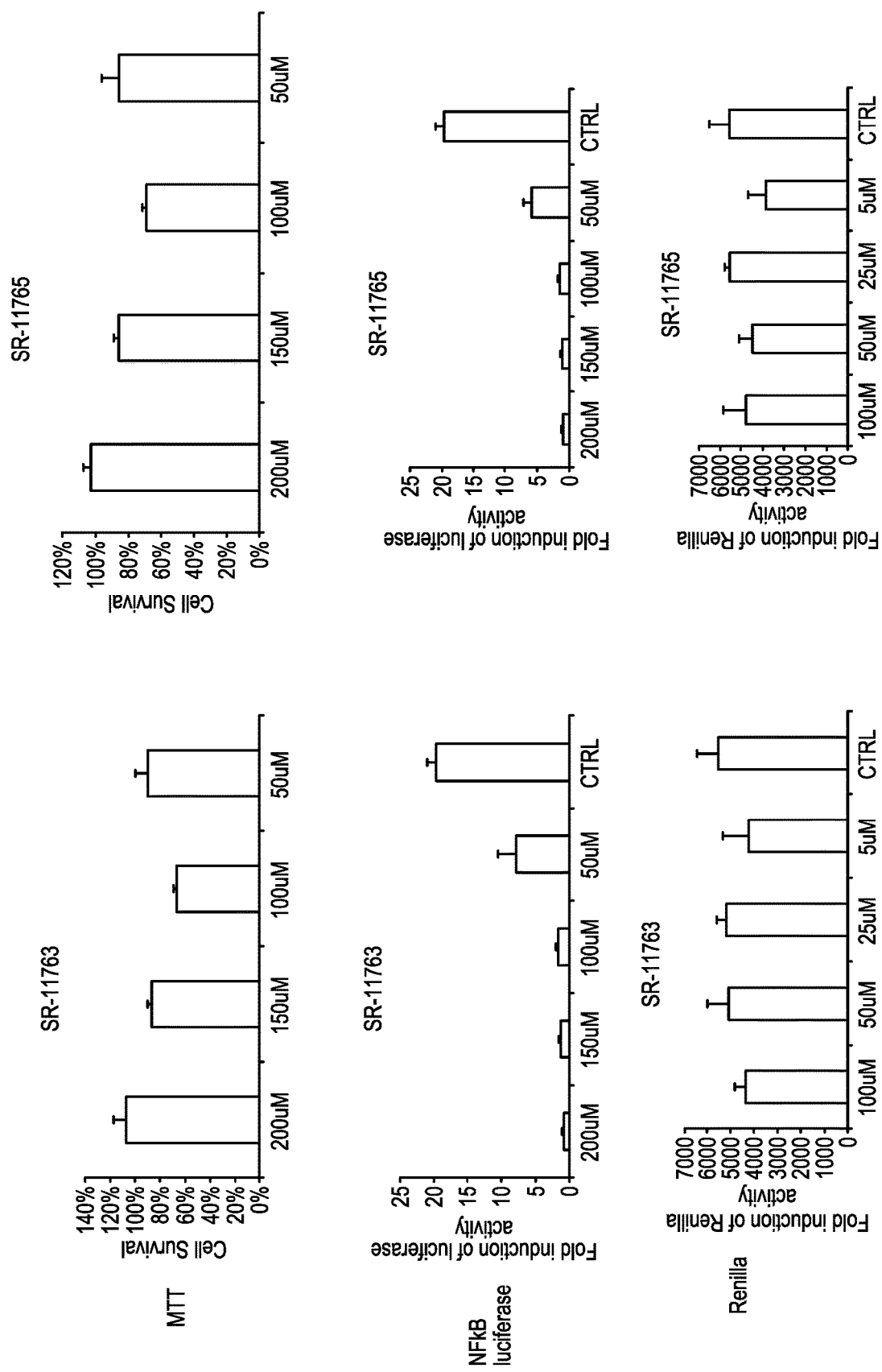
FIG. 29 shows data related to inhibition of NF-κB activity, treating 293-NF-κB-luciferase reporter cells with the compounds SR11763 and SR11765, followed by addition of TNF to induce NF-κB. A reduction in renilla expression or MTT indicates toxicity.
Figure 30:
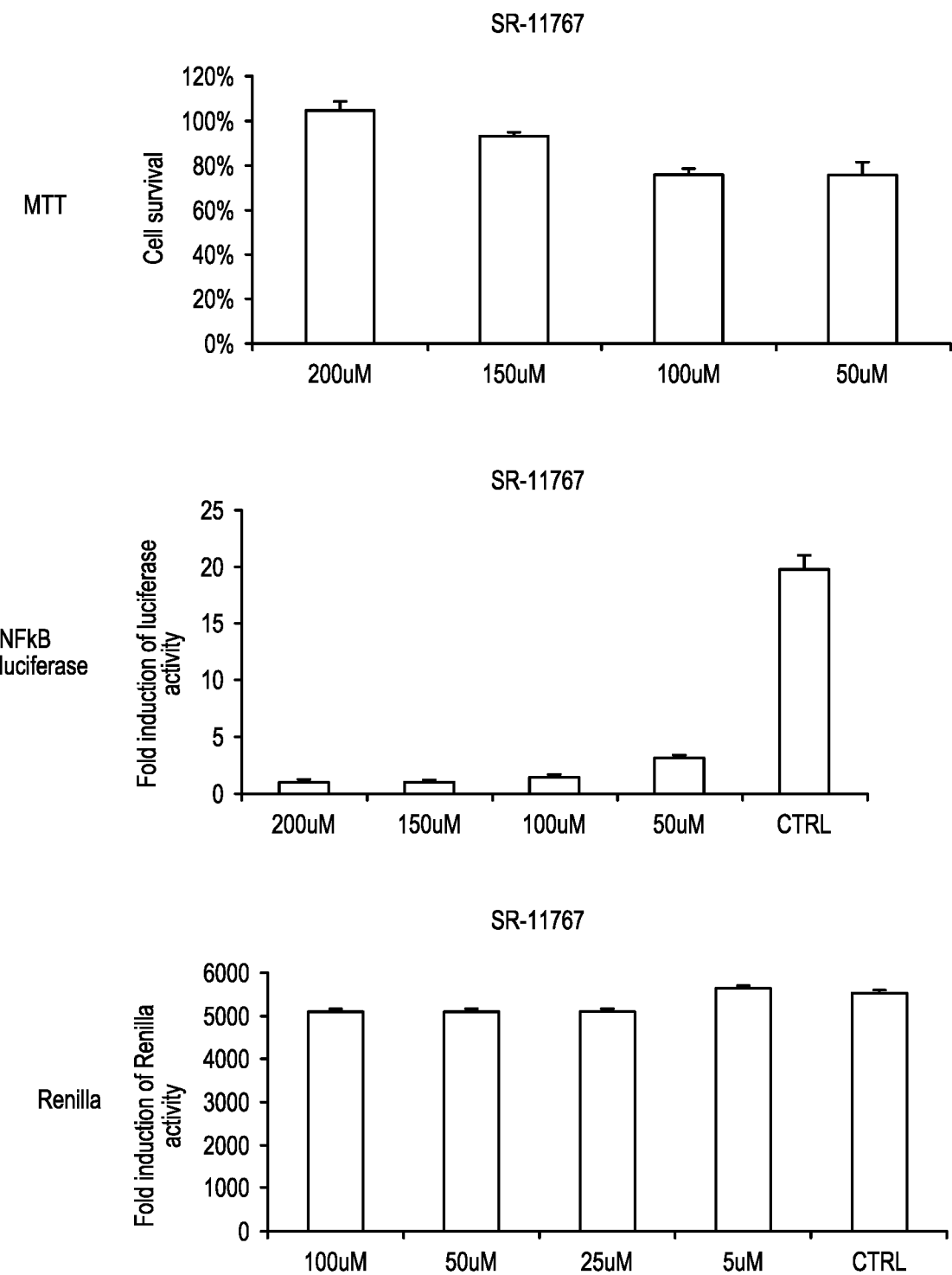
FIG. 30 shows data related to inhibition of NF-κB activity, treating 293-NF-κB-luciferase reporter cells with the compound SR11767, followed by addition of TNF to induce NF-κB. A reduction in renilla expression or MTT indicates toxicity.
Figure 31:
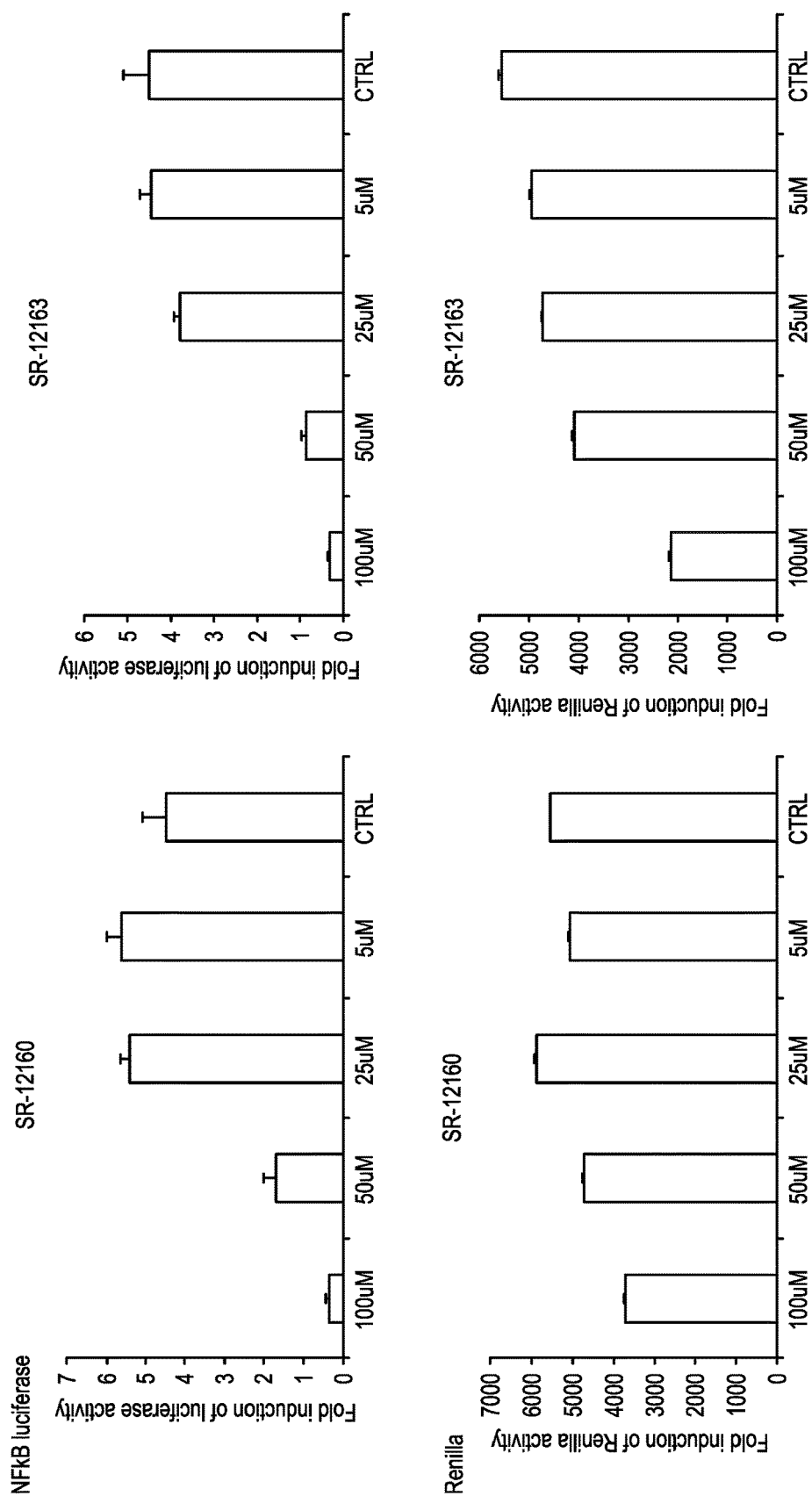
FIG. 31 shows data related to inhibition of NF-κB activity, treating 293-NF-κB-luciferase reporter cells with the compounds SR12160 and SR12163, followed by addition of TNF to induce NF-κB. A reduction in renilla expression or MTT indicates toxicity.
Figure 32:
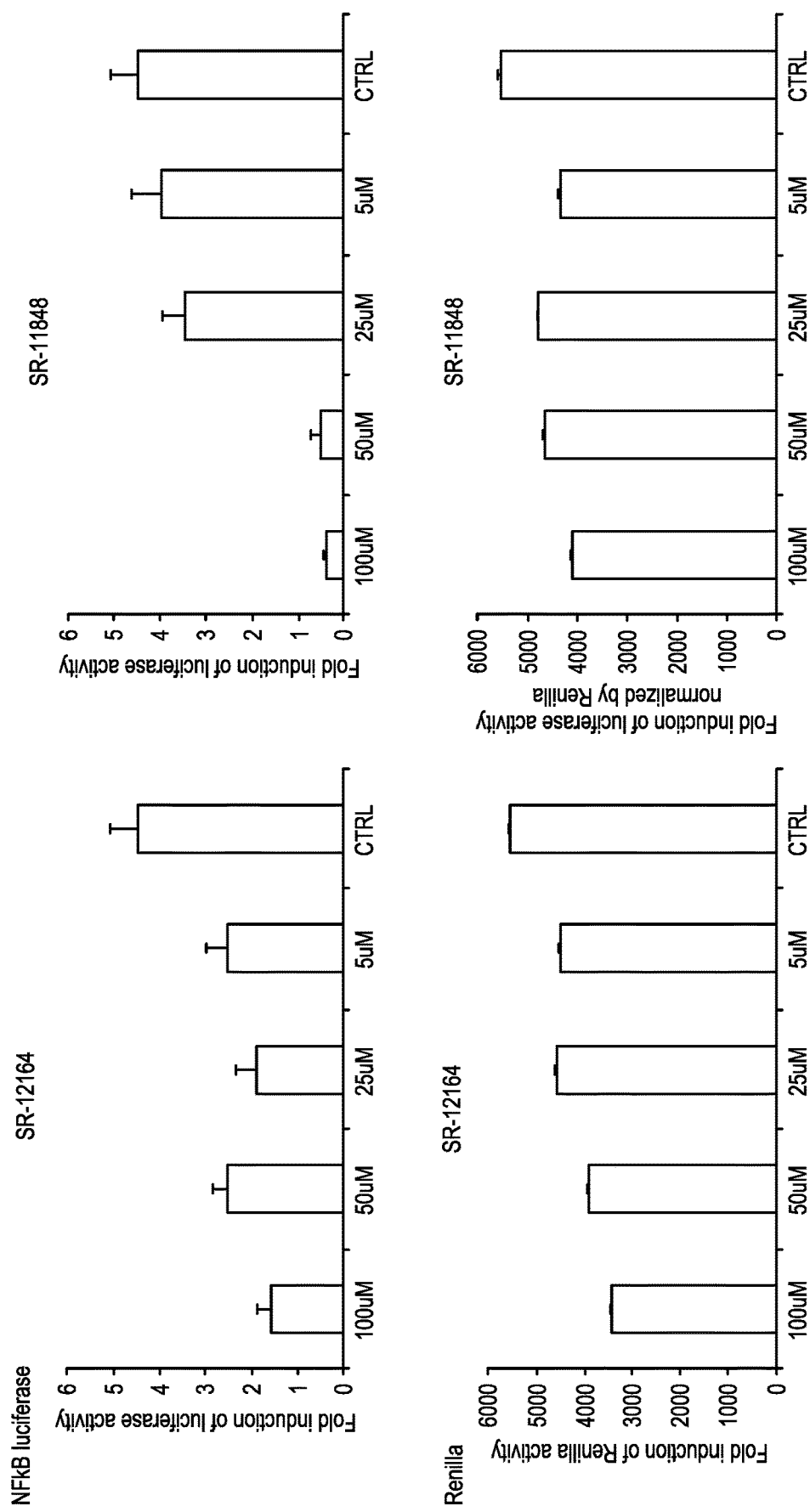
FIG. 32 shows data related to inhibition of NF-κB activity, treating 293-NF-κB-luciferase reporter cells with the compounds SR12164 and SR11848, followed by addition of TNF to induce NF-κB. A reduction in renilla expression or MTT indicates toxicity.
Figure 33:
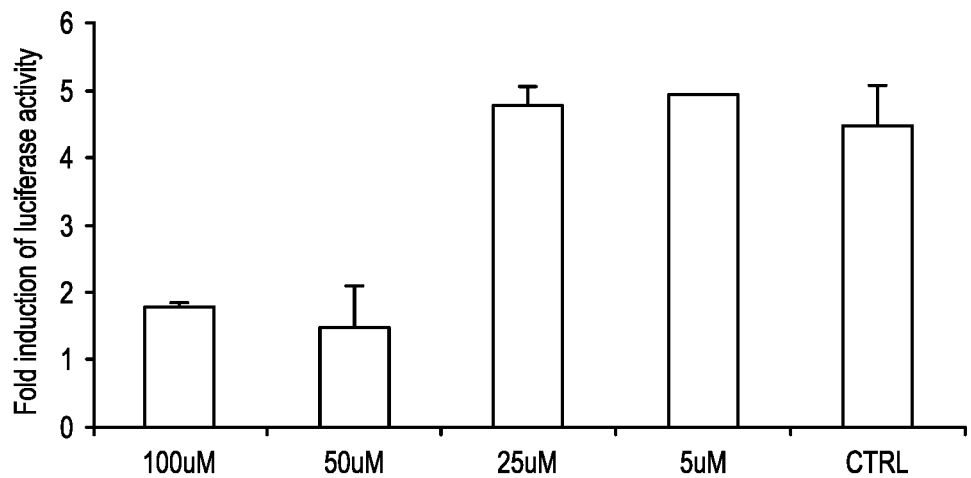
FIG. 33 shows data related to inhibition of NF-κB activity, treating 293-NF-κB-luciferase reporter cells with the compound SR12158, followed by addition of TNF to induce NF-κB. Any reduction in the level of renilla, expressed from a constitutive promoter, expression indicates toxicity.
Figure 33:
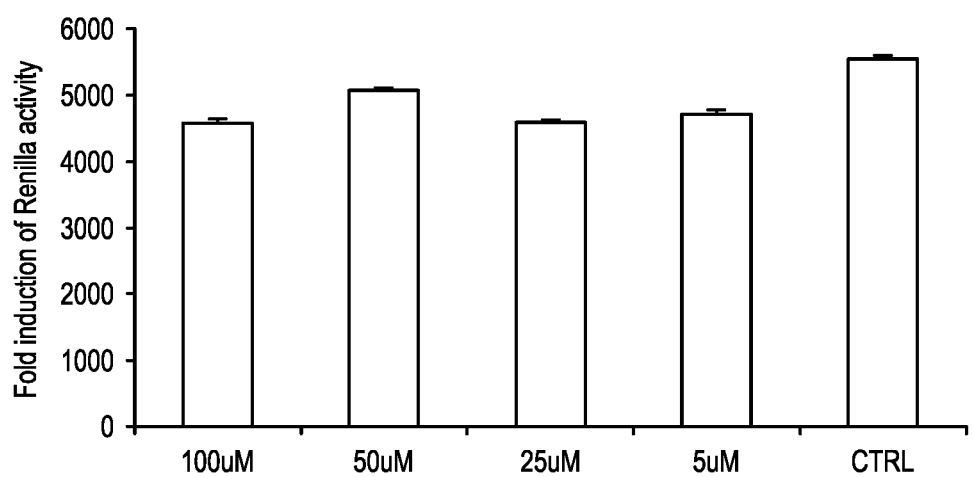

We also tested the compounds for their ability to inhibit NF-κB activity acutely in a murine model of disease. For these experiments, a mouse model of Duchenne muscular dystrophy, which has elevated NF-κB activity in muscle, was treated with Zinc-13 (NBDA-1) and Zinc-5 (NBDA-2) and the level of NF-κB activity determined by gel shift analysis at 1 and 2 hours post-treatment. As shown in FIG. 20, Zinc-13 and in particular Zinc-5, reduced NF-κB DNA binding activity in the skeletal muscle (quadricep) after treatment, similar to 8K-NBD treatment.

Development of Novel Synthetic NEMO-Binding Domain Analogs (NBDA)

Examining the active (Zinc-13 and Zinc-5) compounds originally identified from the ZINC 8.0 database, and the other thirteen compounds that had been identified and biologically tested, and found to be less effective at inhibiting, within a living cell, the interaction between NF-κB essential modulator ("NEMO") with IκB kinase-β (IKK-13) at the NEMO binding domain (NBD), we then undertook the design and synthesis of novel NBDA exhibiting dose dependent inhibition of NF-κB signaling in tissue culture and in animal models. Table 1, below, provides the structures of exemplary compounds of the invention useful for practicing methods of the invention, including a method of inhibiting, within a living cell, the interaction between NF-κB essential modulator ("NEMO") with IκB kinase-β (IKK-β) at the NEMO binding domain (NBD), comprising exposing the cell to an effective amount or concentration of a compound of the invention. As the specific dose dependent inhibition of NF-κB signaling in tissue culture and in animal models resulting from interference with this NEMO/IKK-β interaction is believed to have value in the treatment of disease, the invention also provides a method of treating a condition in a patient, wherein inhibiting the interaction between NF-κB essential modulator ("NEMO") with IκB kinase-β (IKK-β) at the NEMO binding domain (NBD) is medically indicated, comprising administering to the patient an effective dose of a compound of the invention. The condition that can be effectively treated with a compound of the invention or by a method of the invention can include muscular dystrophy, asthma, inflammatory bowel disease, multiple sclerosis, Parkinson's Disease, arthritis, diabetes, graft versus host disease, accelerated aging, heart ischemia, cancer, UV-induced skin damage, or an age-related pathology.

Accordingly, the invention provides for practice of a method of the invention, a compound of formula (I)

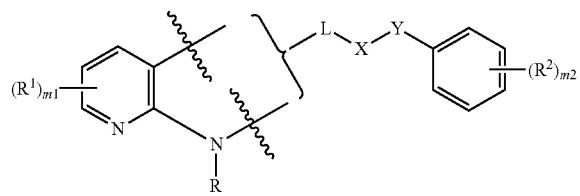

wherein a bracket indicates that the carbonyl group can be bonded to either bond indicated by a wavy line, provided that the other bond indicated by a wavy line is bonded to hydrogen;

the ring bonded to Y comprises 0 or 1 nitrogen atom;

R is H, $(C_1-C_6)$alkyl, $(C_3-C_6)$cycloalkyl$(C_1-C_6)$alkyl, or $(C_2-C_6)$acyl;

each $R^1$ is independently selected halo, alkyl, or haloalkyl; m1=0, 1, 2, or 3;

each $R^2$ is independently selected halo, alkyl, or haloalkyl; m2=0, 1, 2, or 3;

L is a bond, or is C(=O);

X is $(CH_2)_n$, O, $O(CH_2)_n$, $(CH_2)_nO$, NR, $(CH_2)_nNR$, or $NR(CH_2)_n$; or, X is a 5- or 6-membered heteroaryl ring;

Y is C(=O), C(=O)$(CH_2)_n$, NR, $NR(CH_2)_n$, C(=O)NR, or C(=O)$NR(CH_2)_n$;

n=1, 2, or 3;

or a pharmaceutically acceptable salt or a hydrate thereof.

Exemplary compounds are provided in Table 1, below.

In various embodiments, the invention provides a compound of formula (I) as a composition of matter per se, provided the compound of formula (I) is not

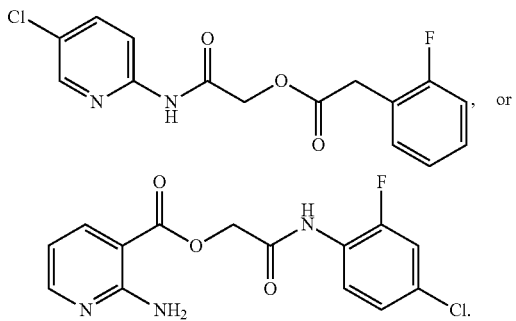

, or

The invention provides, in various embodiments, a method of inhibiting, within a living cell, the interaction of NF-κB essential modulator ("NEMO") with IκB kinase-β (IKK-β) at the NEMO binding domain (NBD), comprising exposing the cell to an effective amount or concentration of a compound of formula (I)

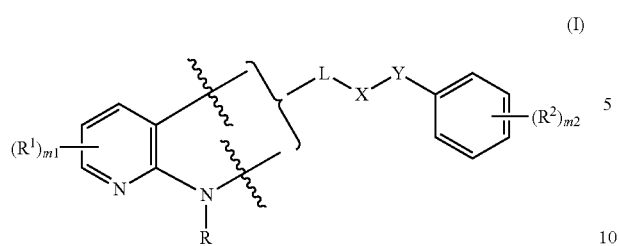

wherein a bracket indicates that the carbonyl group can be bonded to either bond indicated by a wavy line, provided that the other bond indicated by a wavy line is bonded to hydrogen;

the ring bonded to Y comprises 0 or 1 nitrogen atom;

R is H, $(C_1-C_6)$alkyl, $(C_3-C_6)$cycloalkyl$(C_1-C_6)$alkyl, or $(C_2-C_6)$acyl;

each $R^1$ is independently selected halo, alkyl, or haloalkyl; m1=0, 1, 2, or 3;

each $R^2$ is independently selected halo, alkyl, or haloalkyl; m2=0, 1, 2, or 3;

L is a bond, or is C(=O);

X is $(CH_2)_n$, O, $O(CH_2)_n$, $(CH_2)_nO$, NR, $(CH_2)_nNR$, or $NR(CH_2)_n$; or, X is a 5- or 6-membered heteroaryl ring;

Y is C(=O), C(=O)$(CH_2)_n$, NR, $NR(CH_2)_n$, C(=O)NR, or C(=O)$NR(CH_2)_n$;

n=1, 2, or 3;

or a pharmaceutically acceptable salt or a hydrate thereof.

For practice of a method of the invention, and as shown in FIG. 11, the compound of formula (I) is not any of

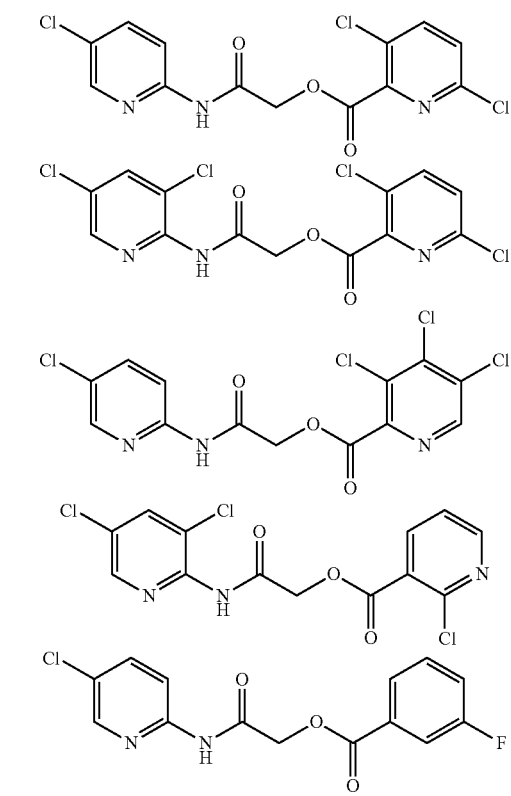

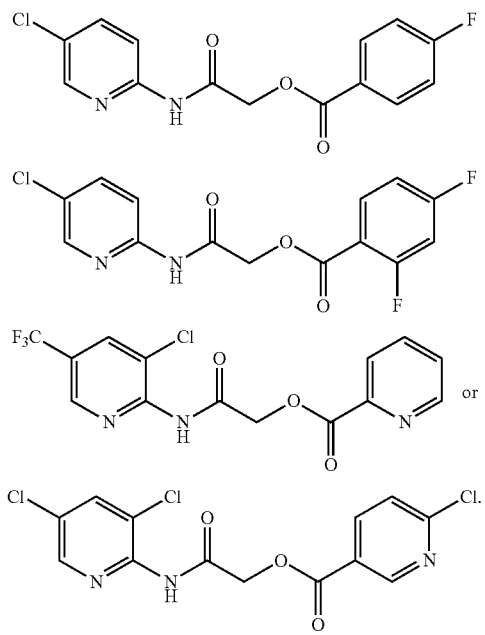

For practice of a method of the invention, the compound of formula (I) can be a compound of formula (IA)

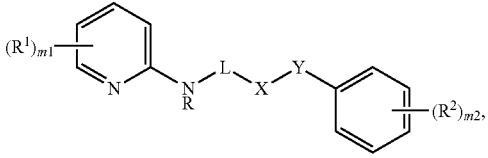

wherein the variable groups are as defined herein. For example, group L can be C=O.

More specifically, for practice of a method of the invention, the compound of formula (IA) can be any of the compounds shown in Table 1, below.

In various embodiments, for practice of a method of the invention, the compound of formula (I) can be a compound of formula (IB)

(IB)

wherein the variable groups are as defined herein. For example, group L can be C=O.

In various embodiments, the invention provides a method of treating a condition in a patient, wherein inhibiting the interaction between NF-κB essential modulator ("NEMO") with IκB kinase-β (IKK-β) at the NEMO binding domain (NBD) is medically indicated, comprising administering to the patient an effective dose of a compound of formula (I)

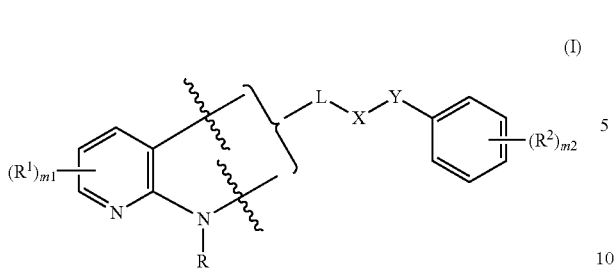

wherein a bracket indicates that the carbonyl group can be bonded to either bond indicated by a wavy line, provided that the other bond indicated by a wavy line is bonded to hydrogen;

the ring bonded to Y comprises 0 or 1 nitrogen atom;

R is H, $(C_1-C_6)$alkyl, $(C_3-C_6)$cycloalkyl$(C_1-C_6)$alkyl, or $(C_2-C_6)$acyl;

each $R^1$ is independently selected halo, alkyl, or haloalkyl; m1=0, 1, 2, or 3;

each $R^2$ is independently selected halo, alkyl, or haloalkyl; m2=0, 1, 2, or 3;

L is a bond, or is C(=O);

X is $(CH_2)_n$, O, O$(CH_2)_n$, $(CH_2)_nO$, NR, $(CH_2)_n$NR, or NR$(CH_2)_n$; or, X is a 5- or 6-membered heteroaryl ring;

Y is C(=O), C(=O)$(CH_2)_n$, NR, NR$(CH_2)_n$, C(=O)NR, or C(=O)NR$(CH_2)_n$;

n=1, 2, or 3;

or a pharmaceutically acceptable salt or a hydrate thereof; optionally in a suitable carrier.

For practice of a method of the invention, in various embodiments, for the compound of formula (I), the compound is not any of

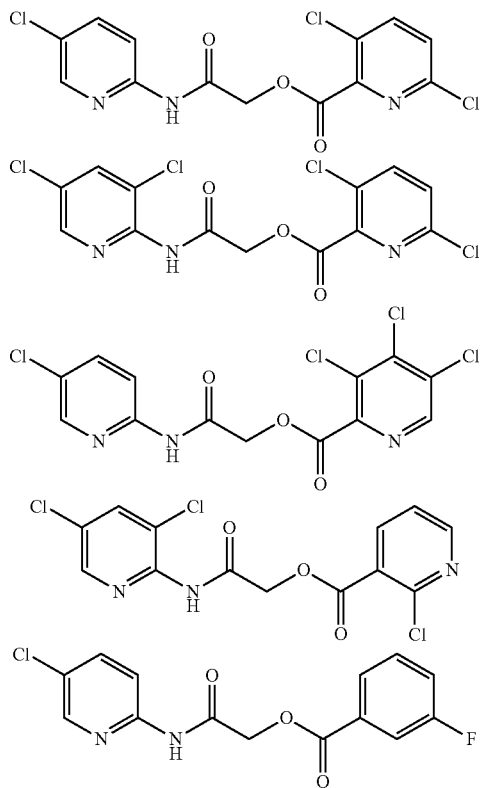

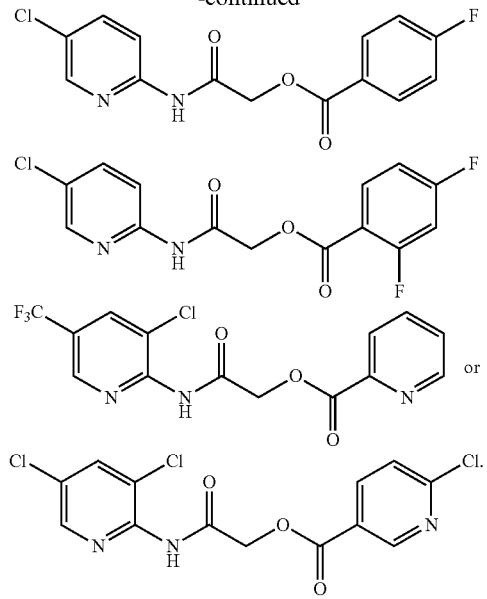

As described above, for practice of a method of treatment of the invention, the compound of formula (I) can be of formula (IA) or of formula (IB). The compound can be any of the compounds shown in Table 1, below. The compound of formula (I) can be administered topically, orally or via injection. For example, the condition in the patient can comprise muscular dystrophy, asthma, inflammatory bowel disease, multiple sclerosis, Parkinson's Disease, arthritis, diabetes, graft versus host disease, accelerated aging, heart ischemia, cancer, UV-induced skin damage, or an age-related pathology.

In various embodiments, a method of treatment of the invention can further comprise administering a second medicament to the patient, wherein the second medicament is medically indicated for muscular dystrophy, asthma, inflammatory bowel disease, multiple sclerosis, Parkinson's Disease, arthritis, diabetes, graft versus host disease, accelerated aging, heart ischemia, cancer, UV-induced skin damage, or an age-related pathology, respectively.

The invention further provides, in various embodiments, as a compound per se, a compound of formula (I)

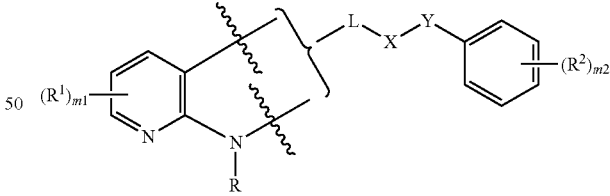

wherein a bracket indicates that the carbonyl group can be bonded to either bond indicated by a wavy line, provided that the other bond indicated by a wavy line is bonded to hydrogen;

the ring bonded to Y comprises 0 or 1 nitrogen atom;

R is H, $(C_1-C_6)$alkyl, $(C_3-C_6)$cycloalkyl$(C_1-C_6)$alkyl, or $(C_2-C_6)$acyl;

each $R^1$ is independently selected halo, alkyl, or haloalkyl; m1=0, 1, 2, or 3;

each $R^2$ is independently selected halo, alkyl, or haloalkyl; m2=0, 1, 2, or 3;

L is a bond, or is C(=O);

X is $(CH_2)_n$, O, O$(CH_2)_n$, $(CH_2)_nO$, NR, $(CH_2)_n$NR, or NR$(CH_2)_n$; or, X is a 5- or 6-membered heteroaryl ring;

Y is C(=O), C(=O)(CH$_2$)$_n$, NR, NR(CH$_2$)$_n$, C(=O)NR, or C(=O)NR(CH$_2$)$_n$;

n=1, 2, or 3;

or a pharmaceutically acceptable salt or a hydrate thereof; provided the compound is not

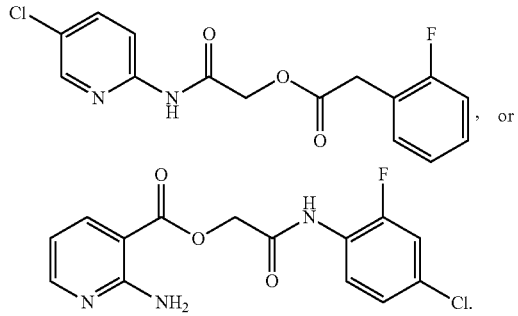

In various embodiments, the compound of formula (I) is a compound of formula (IA)

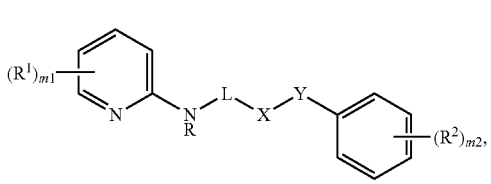

(IA)

wherein the variable groups are as defined as in claim 20. For example, group L can be C=O.

More specifically, the compound can be any of the compounds shown in Table 1, other than

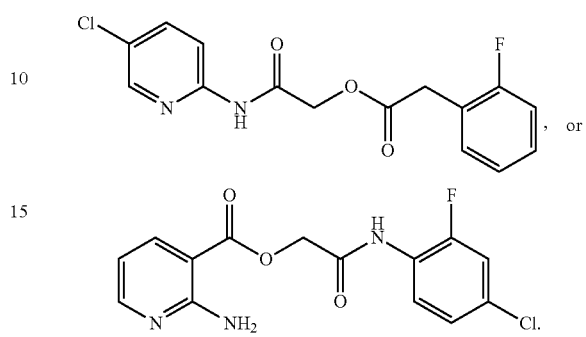

Table 1 shows examples of compounds of the invention (other than NBDA-1 and NBDA-2), and compounds that can be used for practice of a method of the invention. FIG. 11 shows compounds of the structural class that were found to be inactive in inhibiting, within a living cell, the interaction of NF-κB essential modulator ("NEMO") with IκB kinase-β (IKK-β) at the NEMO binding domain (NBD).

TABLE 1

Exemplary Compounds for Practice of Methods of the Invention

| Name | Example # | Structure |
|---|---|---|
| NBDA-1 (Zinc-13) | | 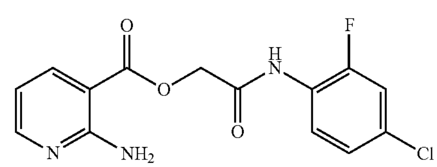 [SMILES: Nc1ncccc1C(=O)OCC(=O)Nc1ccc(Cl)cc1F] |
| NBDA-2 (Zinc-5) | | 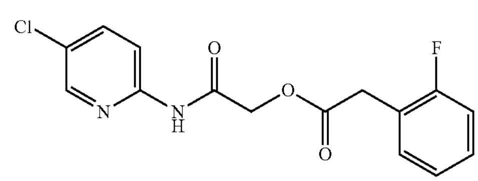 [SMILES: O=C(COC(=O)Cc1ccccc1F)Nc1ccc(Cl)cn1] |
| SR11477 | 25 | 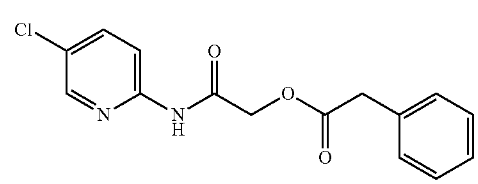 [SMILES: O=C(COC(=O)Cc1ccccc1)Nc1ccc(Cl)cn1] |
| SR11478 | 26 | 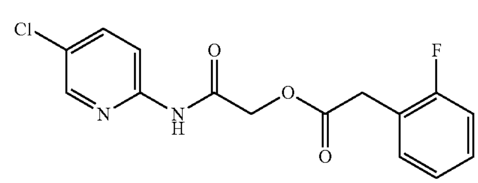 [SMILES: O=C(COC(=O)Cc1ccccc1F)Nc1ccc(Cl)cn1] |

TABLE 1-continued

Exemplary Compounds for Practice of Methods of the Invention

| Name | Example # | Structure |
|---|---|---|
| SR11479 | 27 | 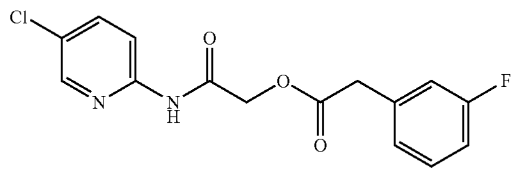 [SMILES: O=C(COC(=O)Cc1cccc(F)c1)Nc1ccc(Cl)cn1] |
| SR11480 | 28 | 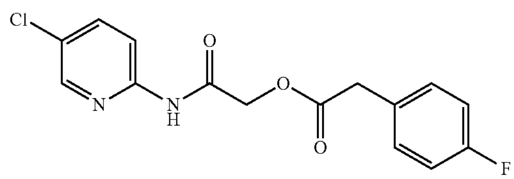 [SMILES: O=C(COC(=O)Cc1ccc(F)cc1)Nc1ccc(Cl)cn1] |
| SR11481 | 29 | 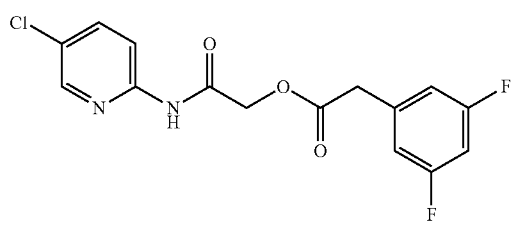 [SMILES: O=C(COC(=O)Cc1cc(F)cc(F)c1)Nc1ccc(Cl)cn1] |
| SR11482 | 30 | 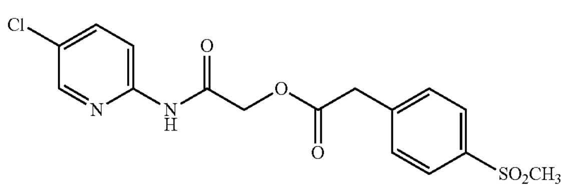 [SMILES: CS(=O)(=O)c1ccc(CC(=O)OCC(=O)Nc2ccc(Cl)cn2)cc1] |
| SR11483 | 31 | 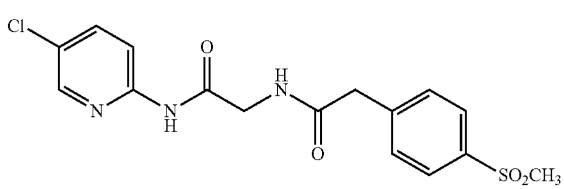 [SMILES: CS(=O)(=O)c1ccc(CC(=O)NCC(=O)Nc2ccc(Cl)cn2)cc1] |
| SR11484 | 51 | 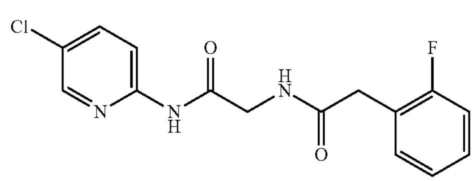 [SMILES: O=C(Cc1ccccc1F)NCC(=O)Nc1ccc(Cl)cn1] |
| SR11485 | 52 | 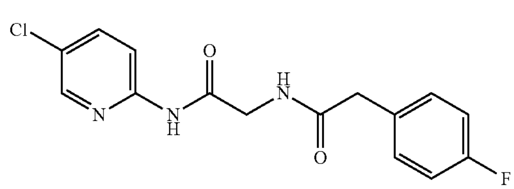 [SMILES: O=C(Cc1ccc(F)cc1)NCC(=O)Nc1ccc(Cl)cn1] |
| SR11577 | 32 | 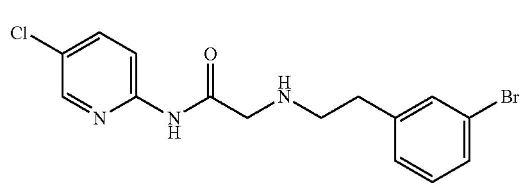 [SMILES: O=C(CNCCc1cccc(Br)c1)Nc1ccc(Cl)cn1] |

TABLE 1-continued

Exemplary Compounds for Practice of Methods of the Invention

| Name | Example # | Structure |
|------|-----------|-----------|
| SR11578 | 39 | 5-chloropyridin-2-yl NHC(O)CH2NH-CH2CH2-phenyl |
| SR11580 | 41 | 5-chloropyridin-2-yl NHC(O)CH2-O-CH2CH2-(3-bromophenyl) |
| SR11735 | 1 | pyridin-3-yl NHC(O)CH2-O-CH2CH2-(3-bromophenyl) |
| SR11759 | 42 | 5-chloropyridin-2-yl NHC(O)CH2-O-CH2CH2-(4-bromophenyl) |
| SR11761 | 43 | 5-chloropyridin-2-yl NHC(O)CH2-O-CH2CH2-(2-bromophenyl) |
| SR11763 | 44 | 5-chloropyridin-2-yl NHC(O)CH2-O-CH2CH2-(4-trifluoromethylphenyl) |
| SR11765 | 45 | 5-chloropyridin-2-yl NHC(O)CH2-O-CH2CH2-(3-fluorophenyl) |
| SR11767 | 46 | 5-chloropyridin-2-yl NHC(O)CH2-O-CH2CH2-(3-methylphenyl) |

TABLE 1-continued

Exemplary Compounds for Practice of Methods of the Invention

| Name | Example # | Structure |
|------|-----------|-----------|
| SR11847 | 3 | 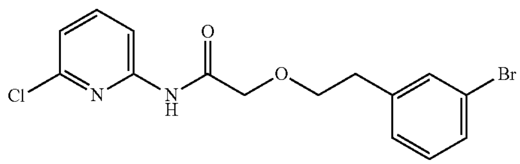 [SMILES: O=C(COCCc1cccc(Br)c1)Nc1cccc(Cl)n1] |
| SR11848 | 4 | 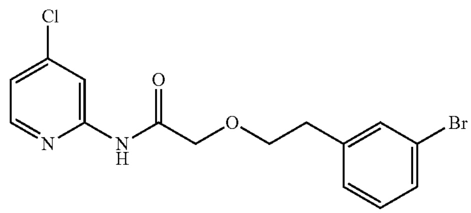 [SMILES: O=C(COCCc1cccc(Br)c1)Nc1cc(Cl)ccn1] |
| SR11849 | 5 | 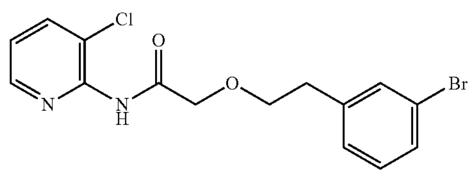 [SMILES: O=C(COCCc1cccc(Br)c1)Nc1ncccc1Cl] |
| SR12157 | 9 | 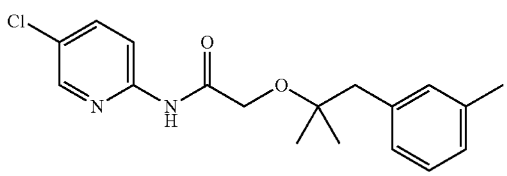 [SMILES: Cc1cccc(CC(C)(C)OCC(=O)Nc2ccc(Cl)cn2)c1] |
| SR12158 | 10 | 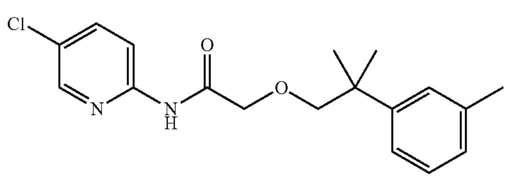 [SMILES: Cc1cccc(C(C)(C)COCC(=O)Nc2ccc(Cl)cn2)c1] |
| SR12160 | 48 | 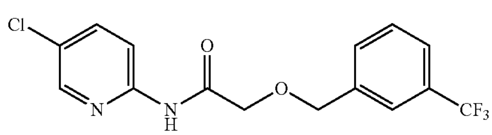 [SMILES: O=C(COCc1cccc(C(F)(F)F)c1)Nc1ccc(Cl)cn1] |
| SR12161 | 49 | 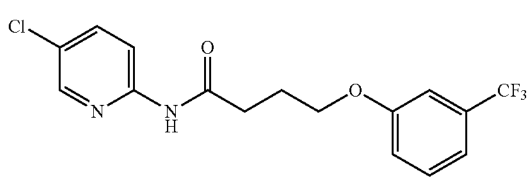 [SMILES: O=C(CCCOc1cccc(C(F)(F)F)c1)Nc1ccc(Cl)cn1] |
| SR12163 | 38 | 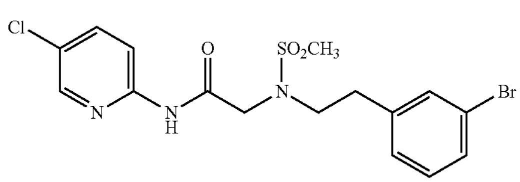 [SMILES: CS(=O)(=O)N(CCc1cccc(Br)c1)CC(=O)Nc1ccc(Cl)cn1] |

TABLE 1-continued
Exemplary Compounds for Practice of Methods of the Invention
| Name | Example # | Structure |
|------|-----------|-----------|
| SR12164 | 33 | 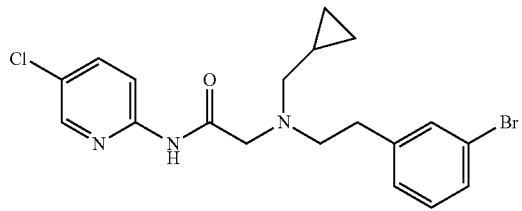 [SMILES: O=C(CN(CCc1cccc(Br)c1)CC1CC1)Nc1ccc(Cl)cn1] |
| SR12174 | 53 | 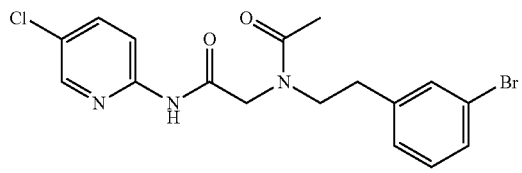 [SMILES: CC(=O)N(CCc1cccc(Br)c1)CC(=O)Nc1ccc(Cl)cn1] |
| SR12343 | 50 | 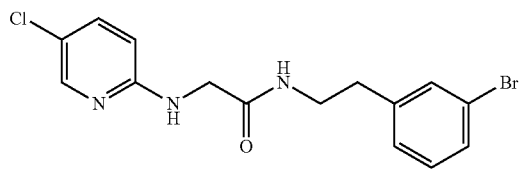 [SMILES: O=C(CNc1ccc(Cl)cn1)NCCc1cccc(Br)c1] |
| SR12344 | 55 | 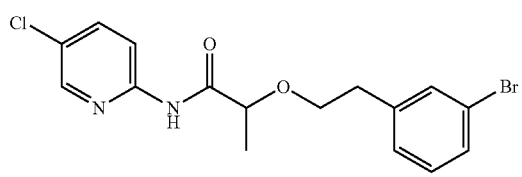 [SMILES: CC(OCCc1cccc(Br)c1)C(=O)Nc1ccc(Cl)cn1] |
| SR12345 | 12 | 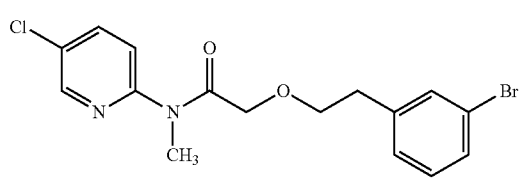 [SMILES: CN(C(=O)COCCc1cccc(Br)c1)c1ccc(Cl)cn1] |
| SR12346 | 13 | 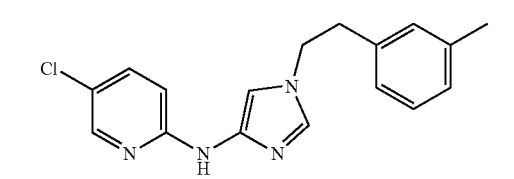 [SMILES: Cc1cccc(CCn2cnc(Nc3ccc(Cl)cn3)c2)c1] |
| SR12347 | 54 | 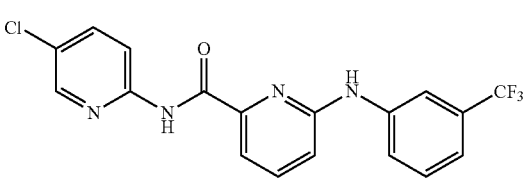 [SMILES: O=C(Nc1ccc(Cl)cn1)c1cccc(Nc2cccc(C(F)(F)F)c2)n1] |
| SR12454 | 16 | 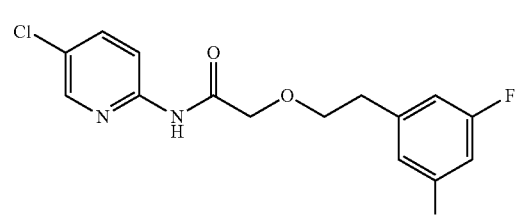 |

TABLE 1-continued

Exemplary Compounds for Practice of Methods of the Invention

| Name | Example # | Structure |
| --- | --- | --- |
| SR12460 | 22 | 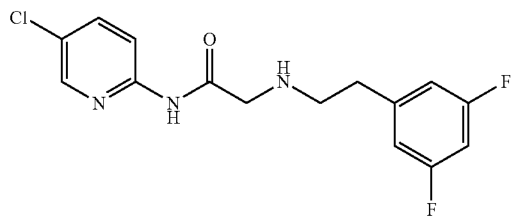 [SMILES: O=C(CNCCc1cc(F)cc(F)c1)Nc1ccc(Cl)cn1] |

TABLE 2

Small molecule derivatives selected from ZINC 10.0 data base share structural similarity to ZINC12909780.

| ZINC ID | Abbreviation | Popular name | Structure |
| --- | --- | --- | --- |
| 09642366 | ZINC1 | (5-chloro-2-pyridyl)carbamoylmethyl | 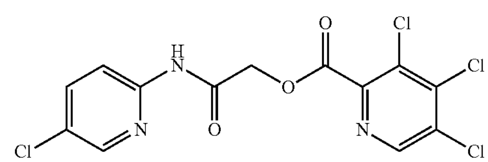 [SMILES: O=C(COC(=O)c1ncc(Cl)c(Cl)c1Cl)Nc1ccc(Cl)cn1] |
| 09645305 | ZINC2 | (3,5-dichloro-2-pyridyl)carbamoylmethyl | 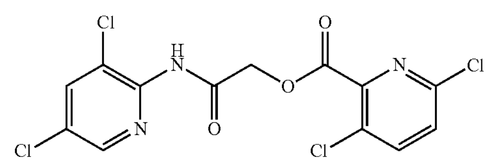 [SMILES: O=C(COC(=O)c1nc(Cl)ccc1Cl)Nc1ncc(Cl)cc1Cl] |
| 04767282 | ZINC3 | (5-chloro-2-pyridyl)carbamoylmethyl | 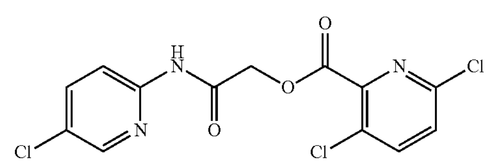 [SMILES: O=C(COC(=O)c1nc(Cl)ccc1Cl)Nc1ccc(Cl)cn1] |
| 05752323 | ZINC4 | [3-chloro-5-(trifluoromethyl)-2-pyridyl]carbamoylmethyl | 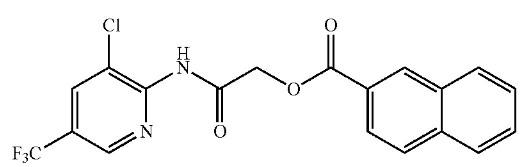 [SMILES: O=C(COC(=O)c1ccc2ccccc2c1)Nc1ncc(C(F)(F)F)cc1Cl] |
| 03369392 | ZINC5 | 2-(2-fluorophenyl)acetic-acid-[2-[(5-chloro-2-pyridyl)amino]-2-keto-ethyl]-ester | 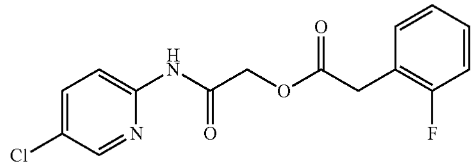 [SMILES: O=C(COC(=O)Cc1ccccc1F)Nc1ccc(Cl)cn1] |
| 03270295 | ZINC6 | 2-chloronicotin-[2-[(3,5-dichloro-2-pyridyl)amino]-2-keto-ethyl]-ester | 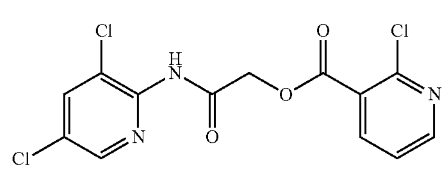 [SMILES: O=C(COC(=O)c1cccnc1Cl)Nc1ncc(Cl)cc1Cl] |

TABLE 2-continued

Small molecule derivatives selected from ZINC 10.0 data base share structural similarity to ZINC12909780.

| ZINC ID | Abbreviation | Popular name | Structure |
|---------|--------------|--------------|-----------|
| 03269263 | ZINC7 | anthracene-9-carboxylic-acid-[2-[[3-chloro-5-(trifluoromethyl)-2-pyridyl]amino]-2-keto-ethyl]-ester | 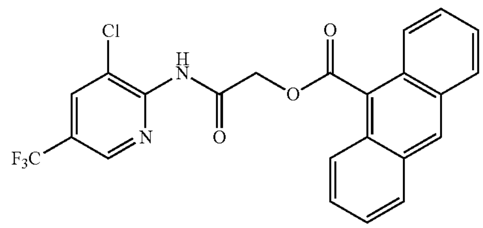 [SMILES: O=C(COC(=O)c1c2ccccc2cc2ccccc12)Nc1ncc(C(F)(F)F)cc1Cl] |
| 03269261 | ZINC8 | naphthalene-1-carboxylic-acid-[2-[[3-chloro-5-(trifluoromethyl)-2-pyridyl]amino]-2-keto-ethyl]-ester | 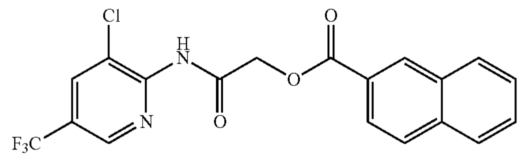 [SMILES: O=C(COC(=O)c1ccc2ccccc2c1)Nc1ncc(C(F)(F)F)cc1Cl] |
| 03264658 | ZINC9 | 2-phenylacetic-acid-[2-[(3,5-dichloro-2-pyridyl)amino]-2-keto-ethyl]-ester | 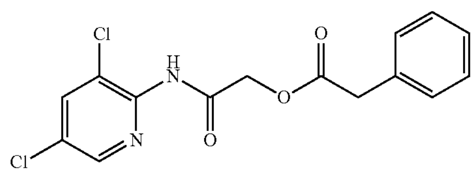 [SMILES: O=C(COC(=O)Cc1ccccc1)Nc1ncc(Cl)cc1Cl] |
| 03260222 | ZINC10 | picolin-[2-[[3-chloro-5-(trifluoromethyl)-2-pyridyl]amino]-2-keto-ethyl]ester | 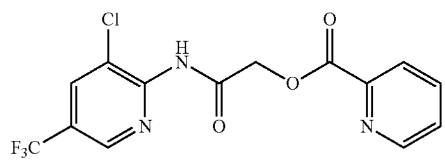 [SMILES: O=C(COC(=O)c1ccccn1)Nc1ncc(C(F)(F)F)cc1Cl] |
| 03257323 | ZINC11 | 6-chloronicotin-[2-[(3,5-dichloro-2-pyridyl)amino]-2-keto-ethyl]-ester | 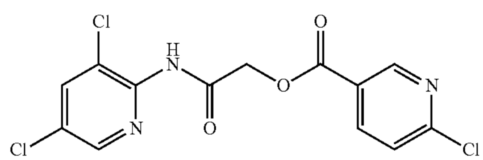 [SMILES: O=C(COC(=O)c1ccc(Cl)nc1)Nc1ncc(Cl)cc1Cl] |
| 03434956 | ZINC12 | 2,4-difluorobenzoic-acid-[2-[(5-chloro-2-pyridyl)amino]-2-keto-ethyl]-ester | 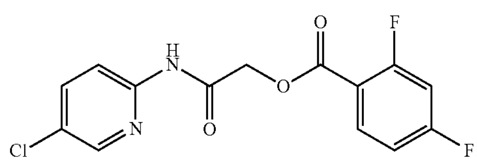 [SMILES: O=C(COC(=O)c1ccc(F)cc1F)Nc1ccc(Cl)cn1] |
| 03425523 | ZINC13 | 2-(2-fluoroanilino)nicotin-(2-amino-2-keto-ethyl)-ester | 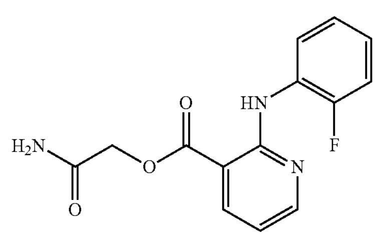 [SMILES: NC(=O)COC(=O)c1cccnc1Nc1ccccc1F] |
| 03401528 | ZINC14 | 3-fluorobenzoic-acid-[2-[(5-chloro-2-pyridyl)amino]-2-keto-ethyl]-ester | 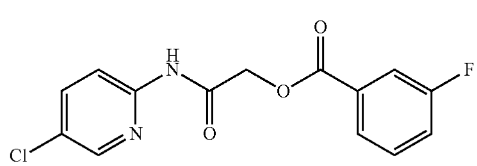 [SMILES: O=C(COC(=O)c1cccc(F)c1)Nc1ccc(Cl)cn1] |

TABLE 2-continued

Small molecule derivatives selected from ZINC 10.0 data base share structural similarity to ZINC12909780.

| ZINC ID | Abbreviation | Popular name | Structure |
|---|---|---|---|
| 03379044 | ZINC15 | 4-fluorobenzoic-acid-[2-[(5-chloro-2-pyridyl)amino]-2-keto-ethyl]-ester | 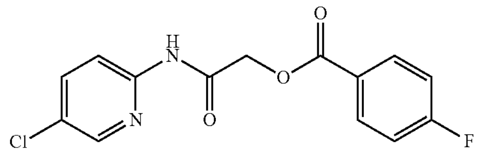 [SMILES: O=C(COC(=O)c1ccc(F)cc1)Nc1ccc(Cl)cn1] |
| 12909780 | NBDA-1 | 2-((4-chloro-2-fluorophenyl)amino)-2-oxoethyl 2-aminonicotinate | 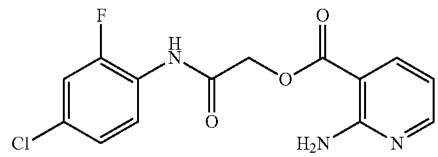 [SMILES: Nc1ncccc1C(=O)OCC(=O)Nc1ccc(Cl)cc1F] |

For purposes of clarity, it is noted that the compound designated Zinc-13 is distinct from the compound designated ZINC13, refer to Tables 1 and 2.

Generation of a Structure-Based Pharmocophore Model Using a Computational Approach Based on the Conserved Interactions Between IKKα/β and NEMO.

Recognition of small molecules by proteins is largely mediated by molecular surface complementarities. We hypothesized that the site of protein-protein interaction between NEMO and IKKβ is a potentially good target for in-silico drug development. To test this hypothesis, as briefly discussed above, we generated a structure-based pharmacophore model. The X-ray structure of the NEMO/IKKβ complex retrieved from the Protein Data Bank [PDB ID: 3BRV], was used to generate a structure-based pharmacophore to investigate the chemical features important in the protein-protein interaction. This was performed using the pharmacophore generation module of LigandScout.

Each interacting atom from each residue was "translated" into a pharmacophoric feature, resulting in the structure-based pharmacophore. The structure-based pharmacophore model consists of eight features (F1, . . . , F8) and 13 exclusion volumes (V1, . . . , V13) representing important atoms from the protein's environment.

This model was used to screen a subset of the drug-like ZINC 10.0 database set (approximately 3.5 million compounds). We identified 161 hits that matched at least 6 features out of eight (F1, . . . , F8) of the pharmacophore model. Twenty hits had an RMSD<1, and were further prioritized using Absorption, Distribution, Metabolism, Excretion, and Toxicity (ADME/Tox) predicted properties. Three compounds have successfully passed these filters and were purchased for biological testing.

Identification of Small Molecule Inhibitors of NF-κB Activation.

To test if the small molecules identified by the in silico screen inhibit NF-κB activation, a HEK293 cell line stably expressing a luciferase reporter driven by a synthetic, NF-κB-dependent promoter was utilized. To induce NF-κB activation, cells were treated with 10 ng/ml of TNF-α and harvested three hours post-treatment for analysis of luciferase activity. Treatment with compound 12909780 (Table 2) slightly downregulated NF-κB activation at a concentration of 100 μM. To determine if compound 12909780 inhibited NF-κB in a dose dependent manner, concentrations were tested at 0, 6.25, 25, 50 and 100 μM. We found that only high concentrations (50 and 100 μM) of the compound were able to inhibit TNF-α-induced NF-κB activation significantly, which is consistent with previous studies that NBD peptide tends to work at higher concentrations compared to kinase inhibitors in cell culture.

To identify NBD mimetics with higher biological activity than compound 12909780 or the NBD peptide, we next screened the ZINC 10.0 database (approximately 3.5 million compounds) in silico for structurally similar compounds (24). Fifteen analogs with a similarity score>90% were identified, and thirteen that passed all the ADME/Tox filters were acquired for testing (Table 2). Four of the compounds, 9642366 (Zinc1), 3369392 (Zinc5), 3269261 (Zinc8) and 3264658 (Zinc9), lowered NF-κB activity robustly while other analogs had minimal effects. To rule out the possibility that the reduction observed in luciferase assays was actually caused by drug toxicity, an MTT assay was performed to assess cell viability. Treatment with ZINC8 resulted in 40% of cell death at 24 hours, suggesting that at least part of the reduction in luciferase activity could be attributed to cytotoxicity. Since ZINC5 displayed potent NF-κB inhibitory efficacy in cell culture showing little toxicity (less than 10%), it was tested for dose-response inhibition of NF-kB. ZINC5 showed a greater extent of inhibitory effect compared to compound 12909780 at 50 and 100 μM, with no cell toxicity observed, suggesting a higher efficacy of ZINC5.

NBD Mimetics Inhibit NF-κB DNA Binding Activity.

To confirm that the NBD mimetics reduce IKK activity, the extent of phosphorylation of the IKK target, IκBα, in response to 10 ng/ml of TNF-α was determined by Western blot at 0, 5 and 10 min after TNF-α stimulation. ZINC5 reduced the level of p-IκBα dramatically following stimulation, while compound 12909780 led to a mild reduction. To determine if the mimetics also reduce NF-κB DNA binding activity, electrophoretic mobility shift assay (EMSA) was conducted both in vivo and in vitro. ZINC5 and compound 12909780 significantly decreased TNFα-induced NF-κB DNA binding activity at 200 μM in C2C12 cells, a mouse myoblast cell line. Similarly, a single ip injection of these two small molecules at 10 mg/kg inhibited NF-κB DNA binding activity in quadriceps in mdx mice. However, chronic treatment of mdx mice with these compounds showed no therapeutic benefit.

Optimization of the NBD Mimetics.

ZINC5 and compound 12909780 (Table 2) both contain ester bonds, leading to their rapid degradation in the presence of serum (data not shown). Thus seven rounds of structural modification and optimization were performed to improve bioactivity and stability and more than one hundred small molecules were tested (data not shown). Four lead NBD mimetics were identified that showed enhanced inhibitory effects, compared to the original ZINC compounds, including three non-esters, SR12343, SR12460 and SR12454, and one ester SR11481 (Table 1). To minimize the influence of drug toxicity on the screening assay, a renilla luciferase reporter driven by the SV40 promoter was cotransfected with the NF-κB luciferase reporter into HEK293 cells as a co-reporter for normalization. Three non-esters showed markedly enhanced inhibition of TNF-α-mediated NF-κB activation: SR12460 with an $IC_{50}$ of 11.34 μM, SR12454 of 20.24 μM and SR12343 of 37.02 μM (Table 3).

The $IC_{50}$ of NBD Mimetics.

Inhibitory effects of NBD mimetics on NF-κB activation were measured by luciferase assays at multiple concentrations: 0, 25, 50, 100 and 150 μM. $IC_{50}$ of NBD mimetics was determined based on the dose-dependent curve by using GraphPad.

TABLE 3

The $IC_{50}$ of NBD Mimics

| NBD Mimic | $IC_{50}$ (μM) |
|---|---|
| SR12460 | 11.23 |
| SR12454 | 20.24 |
| SR12343 | 37.02 |
| SR11481 | 45.03 |

The ester SR11481 only worked at a higher concentration, with an $IC_{50}$ of 45.03 μM, possibly due to the instability of the ester bond. To determine whether these more potent, novel NBD mimetics disrupt NEMO and IKKβ binding, co-immunoprecipitation was performed using Raw 264.7 macrophages and HEK293 cells (data not shown). After treatment with the mimetics or NBD peptide, NEMO was immunoprecipitated by an anti-NEMO antibody and IKKβ was immunoblotted to determine the binding of IKKβ to NEMO. The control 8K-NBD peptide was able to disrupt the protein-protein interaction in macrophages at 400 μM. All four of the mimetics dissociated IKKβ-NEMO interaction at 100 μM, with SR12343, having the strongest activity.

To determine whether the inhibitory effect of the mimetics is TNF-α-dependent, LPS-mediated NF-κB activation via TLR4 was examined to determine a broader inhibitory effect of the novel NBD mimetics. NF-κB was stimulated in Raw 264.7 by 1 ug/ml of LPS for 2 hr and genes transcriptionally regulated by NF-κB were determined by qRT-PCR analysis. Both an IKK active site inhibitor IKKi VII (2 μM) and the 8K-NBD peptide (400 μM) were included as positive controls and the expression of COX2, IL-6, IL-1β, TNF-α, IκBα and iNOS were assessed. SR12460 and SR12454, which are closely structure-related, were able to significantly downregulate the transcription of all NF-κB target genes tested, indicating a comprehensive inhibition of LPS-induced NF-κB activation. SR12343 displayed a similar profile to 8K-NBD peptide, showing significant inhibition on COX2, IL-6 and iNOS expression at a much lower concentration (50 μM) compared to NBD peptide (400 μM). SR11481 failed to suppress all NF-κB target genes, likely due to its poor stability. Interestingly, IKKi VII, while able to inhibit most NF-κB target gene expression, failed to downregulate iNOS expression, which was significantly inhibited by the NBD peptide and all non-ester NBD mimetics. This suggests that IKK inhibitors targeting the ATP-binding pocket, likely downregulates the expression of a distinct subset of genes.

To confirm the qRT-PCR result, LPS-mediated IL-6 production was analyzed in Raw 264.7 cells by ELISA. SR12460 and SR12454 were able to decrease mIL-6 production in a dose-dependent manner, decreasing by half at 25 μM and even to a greater extent at 50 μM. Similarly, SR12343 suppressed mIL-6 production in a dose-dependent manner. However, SR12343 exhibited a less potent inhibitory effect and required a higher working concentration, which is consistent with the $IC_{50}$ in HEK293 cells. Although SR11481 failed to downregulate IL-6 significantly at the mRNA level, there was reduction in the accumulation of IL-6 protein at 24 hr. Moreover, SR11481 appears to work more efficiently at a lower concentration around 25 μM. Taken together, four lead compounds were identified through seven rounds of optimization and modification. They exhibited suppression on both TNF-α- and LPS-induced NF-κB activation by blocking NEMO and IKKβ association at a significantly lower concentration than NBD peptide.

Novel NBD Mimetics Suppress LPS-Induced Acute Pulmonary Inflammation In Vivo.

To determine the stability of the NBD mimetics in vivo, the pharmacokinetics of the compounds was determined in serum following ip injection. SR12460 showed significant stability 2 hr after injection. SR12343 and SR12454 showed moderate stability, whereas SR11481 was extremely unstable with undetectable levels at 2 hr. Since SR12454 and SR12460 share very similar chemical structures and SR11481 is extremely unstable in vivo, SR12460 and SR12343 were selected for further in vivo analysis.

SR12343 and SR12460 initially were tested in an acute model of LPS-induced systemic endotoxemia to determine their NF-κB inhibitory effects in vivo. C57BL/6J mice were pretreated with vehicle control, 8K-NBD peptide or NBD mimetics at 10 mg/kg for 30 min, followed by LPS induction at 10 mg/kg. Lung and liver were harvested 2-4 hr post-treatment for qRT-PCR analysis of NF-κB target genes. SR12343 was able to downregulate NF-κB transcriptional activity significantly in lung, as demonstrated by the inhibition of iNOS, ikBα, COX2 and IL-6, while leaving TNF-α unchanged. Its NF-κB inhibitory effect in liver was less effective compared to lung, inhibiting only COX2 expression significantly. Intriguingly, although SR12460 is much more stable than SR12343, its inhibition of NF-κB/IKK in liver and lung were less potent compared to SR12343. Taken together, the results demonstrate that SR12343 and SR12460 are effective at attenuating LPS-induced acute lung inflammation by suppressing NF-κB target gene expression.

Novel NBD Mimetics Alleviate Necrosis and Muscle Degeneration in Mdx Mice.

Since SR12343 and SR12460 both reduced LPS-induced NF-κB activation in vivo, they were further tested in mdx mice, a mouse model of Duchenne muscular dystrophy. Mdx mice develop normally at birth, and then undergo a massive myonecrosis starting at three weeks. Treatment of mdx mice with IKK/NF-kB inhibitors effectively reduces inflammation, block necrosis and increase muscle regeneration. Mdx mice were chronically treated with vehicle, SR12343, SR12460 or 8K-NBD starting from day 21, 3 times/week for 4 weeks. No significant weight loss was observed in chronically treated mdx mice. To determine if SR12343 and SR12460 improve muscle pathology, tibialis anterior (TA) muscle was stained with hematoxylin and eosin (H&E) to assess inflammatory infiltration, necrosis, central nucleation and fibrosis. Vehicle treated TA muscles exhibited extensive infiltration and necrosis as reflected by clusters of inflammatory cells, disorganized myofibers and nonuniform staining, with limited muscle regeneration. Consistent with previous studies, 8K-NBD peptide reduced inflammatory cell infiltration and necrosis and also promoted muscle regeneration as shown by centralized nuclei. Interestingly, SR12343 treatment led to the most significant pathological improvement, as represented by limited infiltration and enhanced muscle reconstruction. Similarly, SR12460 treatment partly improved muscle pathology, although not as significant as SR12343. As compared to the control group, qRT-PCR analysis revealed significant improvement of myofiber regeneration in SR12343 treated TA muscle, by increasing expression of eMyHC as well as Pax 7, a marker of skeletal muscle satellite cells. SR12460 and 8K-NBD also increased eMyHC expression, but to a lower extent compared to SR12343. Fiber size in centrally nucleated and non-centrally nucleated myofibers was also smaller in mice treated with SR12343 and 8K-NBD, indicating active reconstruction of myofiber during the regenerative phase.

To determine muscle strength post-treatment, grip strength test on forelimbs was performed 2 weeks and 4 weeks post-treatment. Compared to vehicle group, SR12343 significantly improved forelimb strength after 2 weeks of treatment, indicating rapid muscle repair and inflammatory flameout. All treatment groups, compared to control, significantly strengthened forelimb muscles 4 weeks post-treatment. Taken together, the two lead compounds, SR12460 and, in particular, SR12343, markedly improved muscle function and muscular pathology in mdx mice.

NBD Mimetics Selectively Inhibit IKK/NF-κB Activity

Thus, we have identified and optimized several novel NBD mimetics that selectively inhibit IKK/NF-κB activity. The two lead compounds, SR12343 and SR12460, inhibit both TNF-α- and LPS-induced NF-κB activation more effectively and at a lower concentration than the NBD peptide in both HEK293 and Raw 264.7 cells. We also demonstrate that the NBD mimetics, distinct from the existing ATP-competitive inhibitors targeting IKKβ or IKKα, could disrupt the IKK complex shown by the co-immunoprecipitation. Interestingly, although SR12343 is less stable compared to SR12460 as shown by the pharmacokinetic analysis, it display stronger inhibitory and therapeutic effects in the LPS-induced ALI model and mdx mice, where the pathology is mainly mediated by activated immune cells.

To identify the NBD mimetics, a computational screening based on the pharmacophore model was used. A crystal structure study identified amino acid residues W741, W739 and F734 as the essential hydrophobic motifs interacting with NEMO. Consistently, a mutated 11-mer NBD peptide (735-745), with substitutions of arginine for W741 and W739, was unable to bind to NEMO. A longer IKKβ-derived peptide (701-746) containing all residues and domains, exhibited the strongest affinity to NEMO with $IC_{50}$ around 10 nM, compared to the traditional 11-mer NBD peptide that was less potent, with $IC_{50}$ around 100 μm. To identify NBD mimetics with higher affinity and bioactivity, the third residue F734 that was left out of the 11-mer NBD peptide, was included in our pharmacophore model and in silico screening. The novel NBD mimetics were able to inhibit NF-κB activity in a dose-dependent manner with an $EC_{50}$ around 10-40 μM, which is lower than 11-mer NBD peptide. These results are consistent with current evidence that although $IKK\beta_{737-742}$ is the core component essential for IKK complex formation, $IKK\beta_{701-746}$ contributes greatly to the binding affinity between IKKβ and NEMO.

We demonstrate that a structure-based pharmacophore model is able to identify small molecules selectively targeting protein-protein interface. The novel, identified NBD mimetics could dissociate preformed NEMO/IKKβ complexes robustly in multiple cell lines, consistent with previous reports that NBD peptide also blocks the association of preformed IKK complexes. Although it is unclear if the small molecule NBD mimetics disrupt the binding of NEMO and IKKα, there is evidence suggesting that NBD peptide preferably forces IKKβ, but not IKKα, to leave the IKK complex. In addition, NBD peptide has been shown to disrupt the association between IKKα and NEMO and reduce IL-1 induced IKKβ-independent NF-κB activation via IKKa, at a much lower affinity. This could explain why NBD peptide exhibited greater therapeutic efficacy in various in vivo models than IKK kinase inhibitors, most of which only preferentially target IKKβ. Clearly, further analysis of the interaction of not only the mimetics with IKK, but also the NBD peptide is needed.

The NBD peptide appears not to affect basal activity of NF-κB and thus has minimal undesirable side effects. This is of interest since complete abrogation of NF-κB activity in mice lacking IKKβ leads to generalized apoptosis, tissue injury and embryonic lethality, due to TNFα-induced apoptosis. We observed no apparent signs of liver or kidney toxicity, nor infection tendency from the chronically treated mice. It is of interest that the NBD mimetics inhibited a unique subset of target genes compared to IKK kinase inhibitors, particularly iNOS both in vitro and vivo. The expression of iNOS in response to LPS can be downregulated by 6 fold in Raw264.7 cells and by 50% in both lung and liver, by the treatment with NBD mimetics. iNOS is involved in arginine metabolism, leading to the production of citrulline and nitric oxide (NO), the latter of which, acting as a free radical, promotes cytotoxicity and tissue injury. Its role, as a central mediator of neutrophil recruitment, has been well established in the pathophysiology of LPS-induced ALI and sepsis. iNOS-knockout mice or mice treated with NOS inhibitors have been reported to exhibit an attenuated inflammatory response and tissue injury in multiple models of lung inflammation. Additionally, increased production of iNOS, by metabolizing arginine to NO in macrophages, has been linked to M1 macrophages that is characterized by $iNOS^{high}/CD206^{low}$, and their NO-dependent cytolysis function, iNOS-null mdx mice have been demonstrated to have significantly reduced macrophage cytolysis and decreased myofiber injury at both acute, necrotic phase (4 weeks) and regenerative phage (6-12 weeks), suggesting a critical role of NO-mediated myonecrosis in the pathology of mdx mice. Our results demonstrated a robust inhibition of iNOS expression by the treatment of NBD mimetics and NBD peptide in Raw264.7 cells in response to LPS, which suggests that the improvement observed in muscle pathology in mdx mice may be mediated by suppressed NO-dependent macrophage killing. Indeed, our data showed reduced necrosis in treated mice in comparison to controls, in particular, in SR12343 treated mice, confirming the central role of macrophges in mediating a secondary mucular injury in mdx mice.

Similar to the finding of mdx mice treated with NBD peptide, we found increased myogenesis, in addition to reduction in necrosis and inflammation, in particular by SR12343 treatment, as shown by higher expression of eMyHC and Pax 7 and smaller size of centrally-nucleated fibers. This is in line with previous report that NF-κB regulates cell differentiation via its transcriptional regulation on cyclin D1. The study provides compelling evidence that the small molecule NBD mimetics can simultaneously inhibit pro-inflammatory responses, reduce macrophage cytotoxicity and improve muscle degeneration, showing an even greater improvement in pathology than NBD peptide. Thus, novel NBD mimetics could be used clinically to treat DMD.

We previously have demonstrated that chronic treatment of the Ercc1$^{-/\Delta}$ mouse model of accelerated aging with the NBD peptide delayed onset of numerous age-related symptoms, improved pathology and reduced cellular senescence. Similar to the NBD peptide, chronic treatment of Ercc1$^{-/\Delta}$ mice with SR12343 resulted in an extension of healthspan. In addition, in a mouse model of skin photoaging, topical treatment with SR12343 improved molecular markers of skin aging as well as the overall appearance of the skin. Thus these novel NBD mimetics could be used not only for treatment of inflammatory and degenerative diseases, but also aging.

Collectively, our data demonstrate that the novel small molecule NBD mimetics are potent and highly selective IKK inhibitors by disrupting the association of IKK complexes. They exhibited significant inhibitory effects on NF-κB activation in the model of LPS-induced ALI and the murine model of DMD (mdx mice), indicating that NBD mimetics can become a distinct class of anti-inflammatory drugs. Taken together, NBD mimetics can provide therapeutic values for the chronic management of inflammatory diseases and cancers.

Biological Results

Compounds for practice of a method of the invention, including NBDA-1, NBDA-2, SR11479, SR11481, SR11577, SR11580, SR11735, SR11759, SR11763, SR11765, SR11767, SR11848, SR12158, SR12160, SR12163, SR12164, SR12345, SR12346, and SR12347, (see Table 1), were evaluated for their NF-κB suppressing bioactivity, and for their cellular toxicity. Results are shown in FIGS. 21-33. Toxicity data are indicated by the results obtained with Renilla and MTT bioassays.

Figure 34:
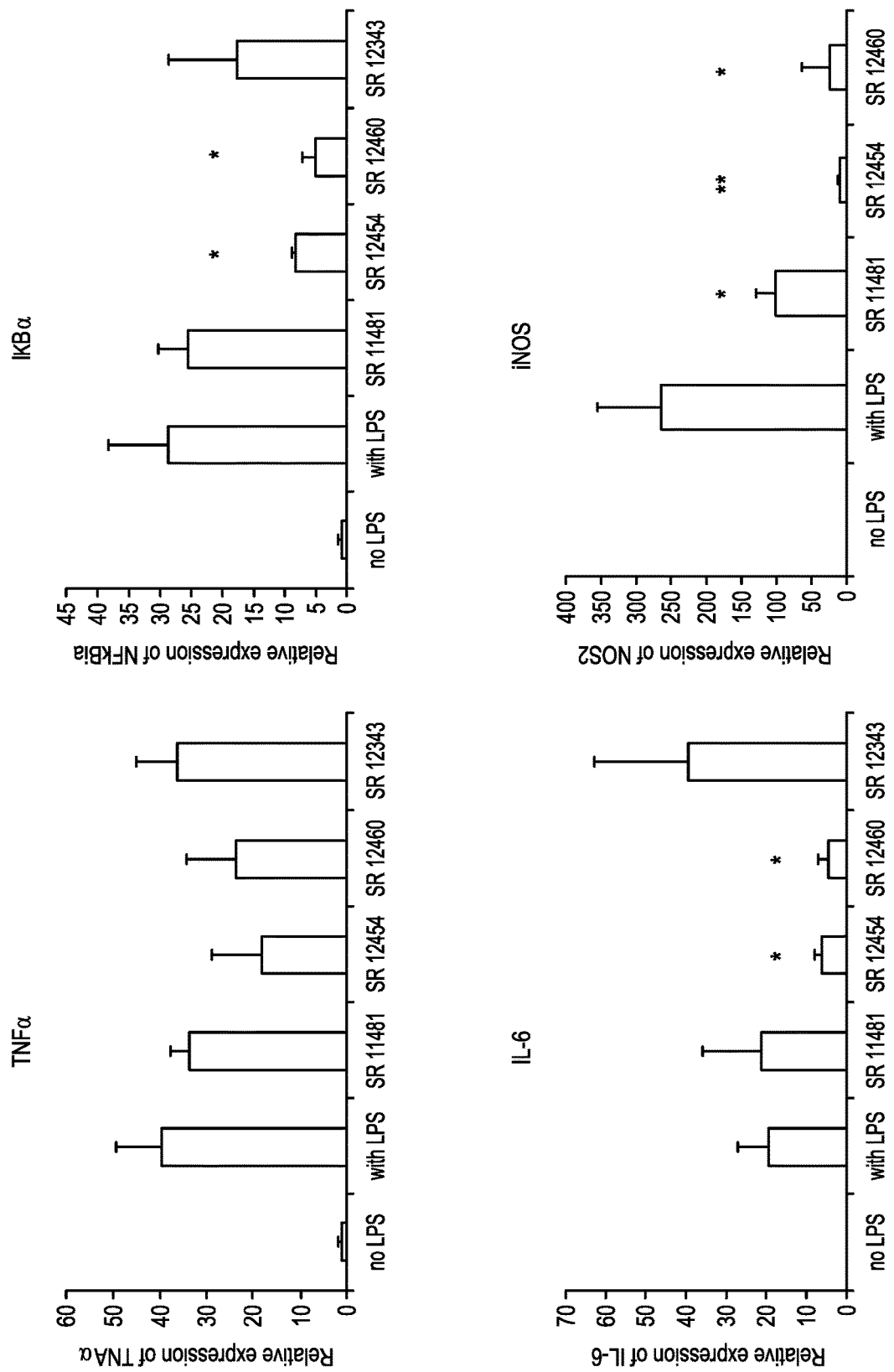
FIG. 34 shows the relative expression of TNFα, IκBα, IL-6, and iNOS with compounds SR11481, SR12454, SR12460, and SR12343, versus controls with and without LPS. Effect of the NBD mimetics on expression of NF-kB regulated genes in the Raw mouse macrophage cell line. Treatment of the Raw cells with the indicated drugs prior to addition of LPS reduced NF-kB-mediated gene expression as measured by RT-PCR.
Figure 35:
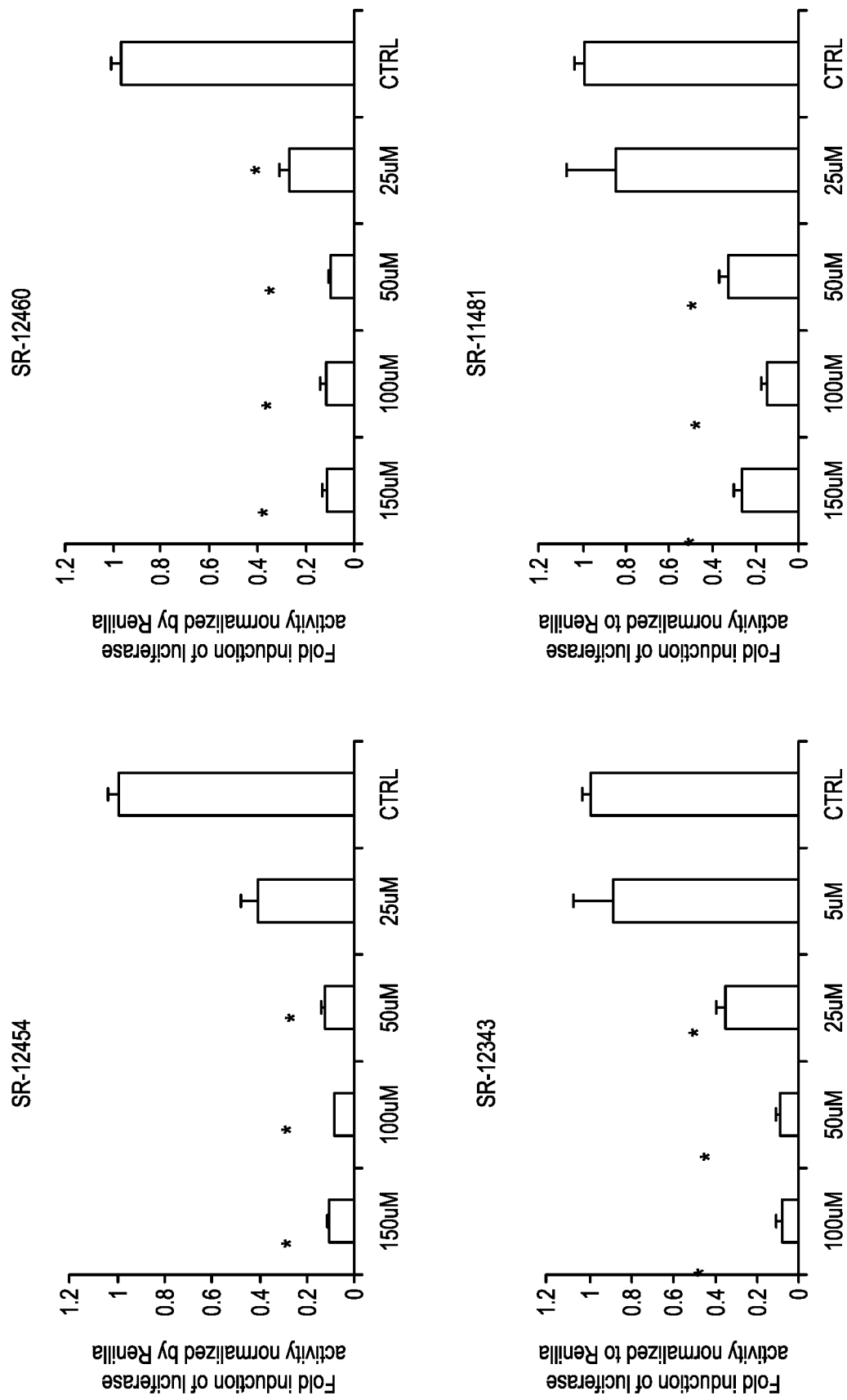
FIG. 35 shows data related to inhibition of NF-κB activity, and toxicity, treating 293-NF-κB-luciferase reporter cells with the compounds SR11481, SR12343, SR12454, and SR12460, followed by addition of TNF to induce NF-κB. Effect of the NBD mimetics on expression of a NF-kB-luciferase reporter in 293 cells. The indicated concentrations of the drugs were added to a 293-NF-kB luciferase reporter cells followed by addition of TNF-α. The levels of luciferase were then measured 24 later. See Table 1 for structures.
Figure 36:
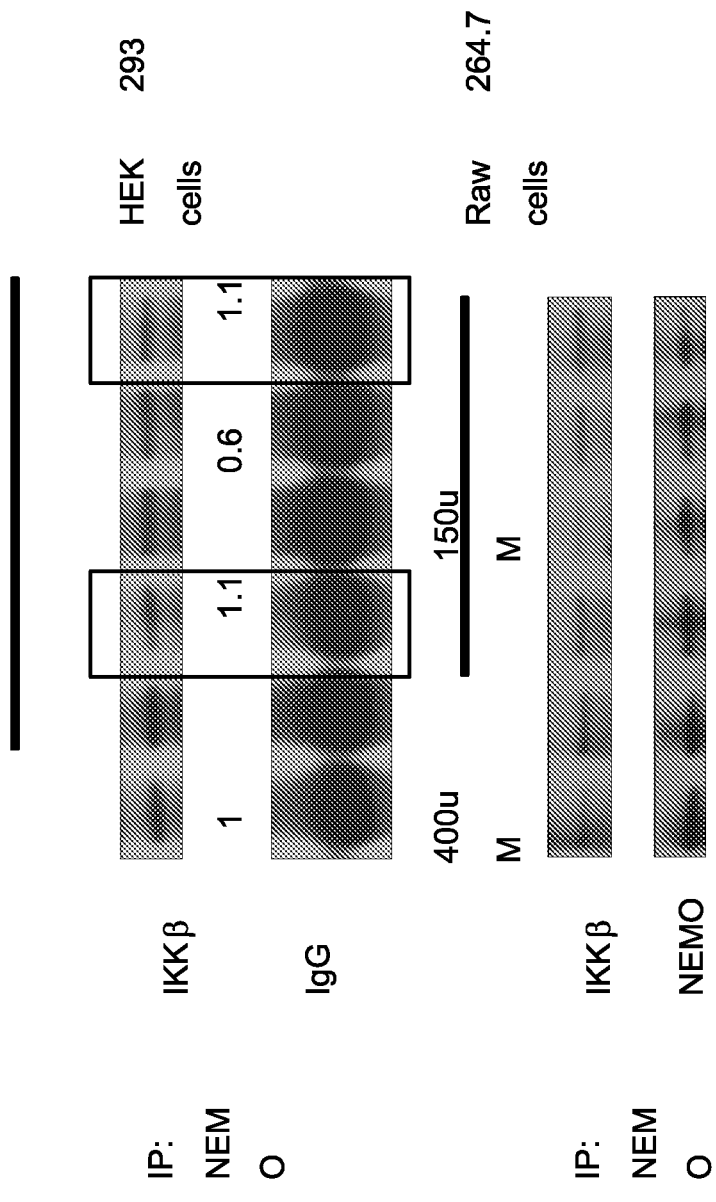
FIG. 36 shows Western analysis of IKKß following immunoprecipitation of NEMO, indicating disruption of the association between NEMO and IKK-β by NBD mimetics SR11481, SR12343, SR12454, and SR12460. The NBD mimetics reduce the interaction between IKKg (NEMO) and IKKß. The indicated concentrations of the drugs were added to HEK 293 or Raw 264.7 cells and cell extracts prepared 30 minutes later. Following immunoprecipitation (IP) of NEMO, the Western was probed for IKKß.
Figure 37:
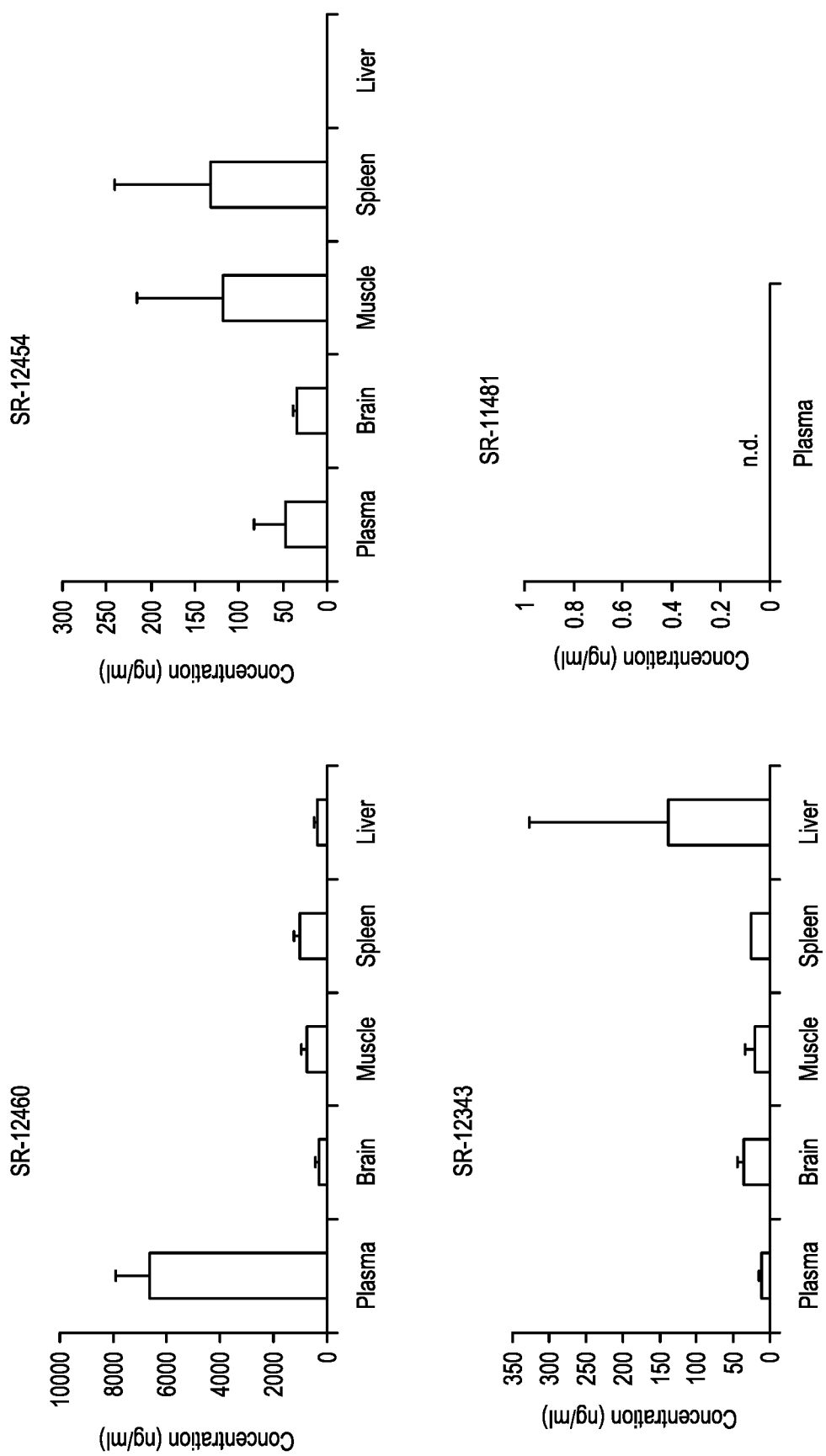
FIG. 37 depicts data obtained by use of mass spectrometry indicating the qualitative stability over time of each of the four indicated compounds, SRI 1481, SR12343, SR12454, and SR12460, in various tissues 2 hours post IP injection. The levels of the NBD mimetics are shown in plasma and tissues two hours post-IP injection
Figure 38:
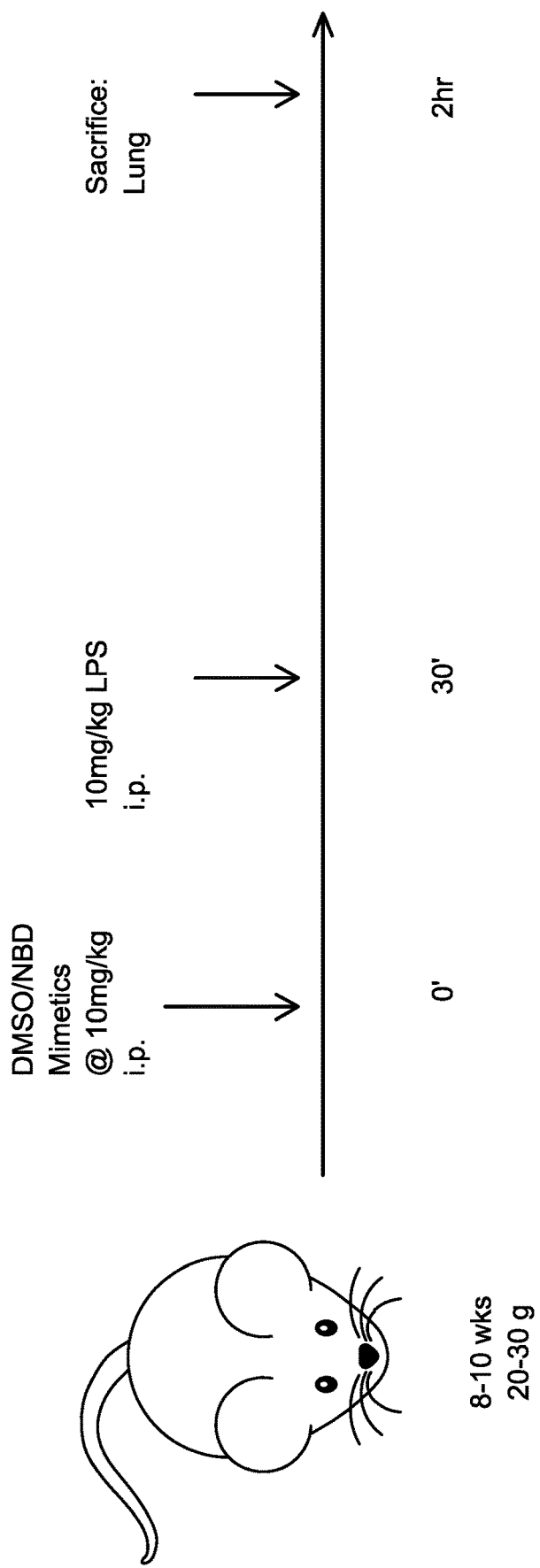
FIG. 38 shows a schematic view of the protocol used to evaluate NBD mimetics in a lipopolysaccharide (LPS) induced acute inflammation model in mice.
Figure 39:
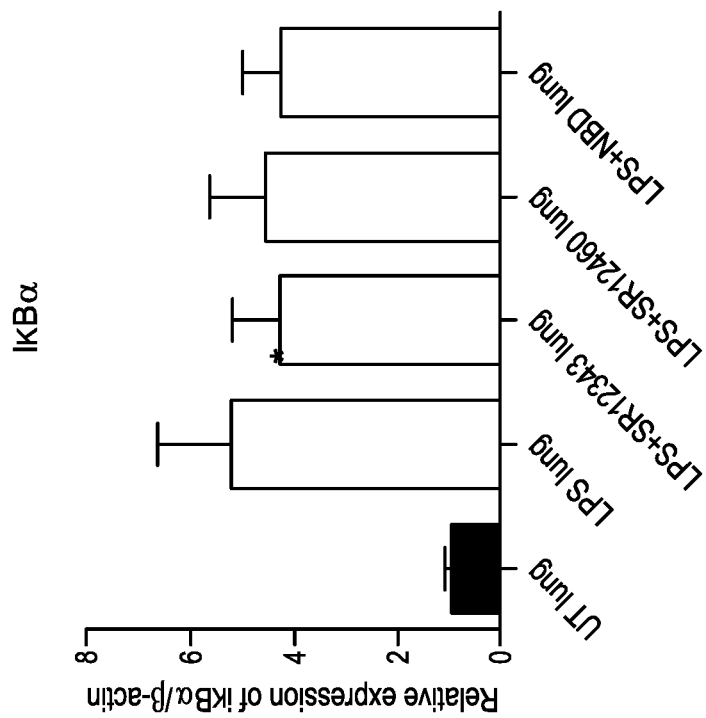
FIG. 39 shows bar graphs indicating the relative level of expression of NF-κB target genes in lung following their LPS-induced activation as measured by RT-PCR. The NBD mimetics reduce expression of iNOS and IkB, as measured by RT-PCR in lung tissue more effectively than the NBD peptide following acute LPS treatment.
Figure 39:
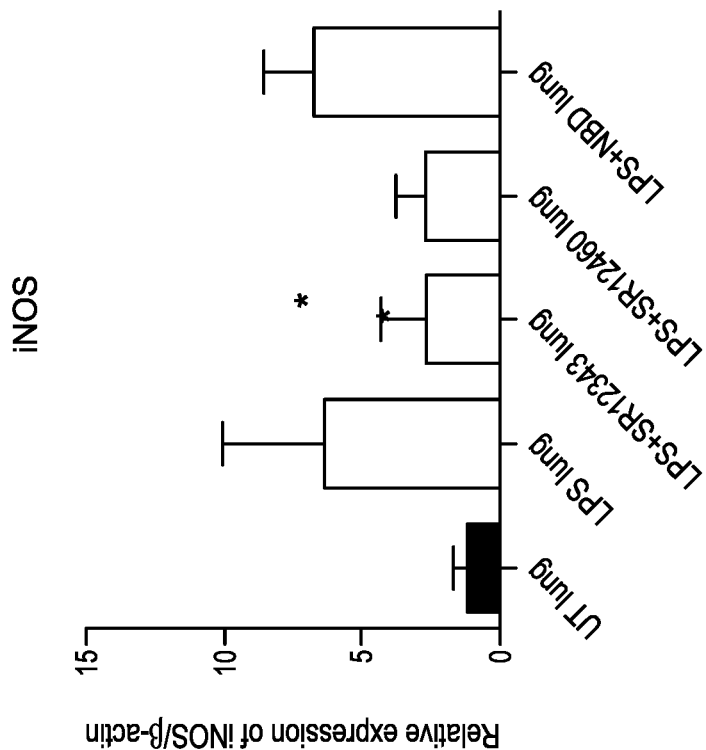
Figure 40:
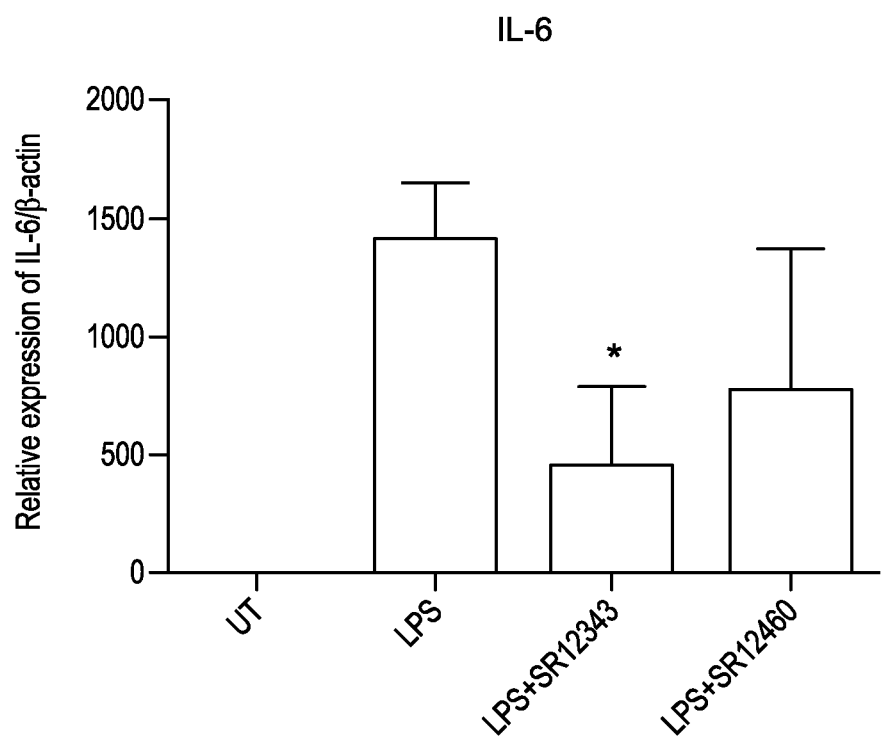
FIG. 40 shows a bar graph indicating the pooled level of expression of NF-κB target genes in lung following their LPS-induced activation as measured by RT-PCR. The NBD mimetics reduce expression of IL-6, as measured by RT-PCR in lung tissue, following acute LPS treatment FIG. 41 summarizes the regimen and endpoints for the study of the effects of NBD mimetics on aging using the Ercc1$^{-/\Delta}$ mouse model of accelerated aging
Figure 41:
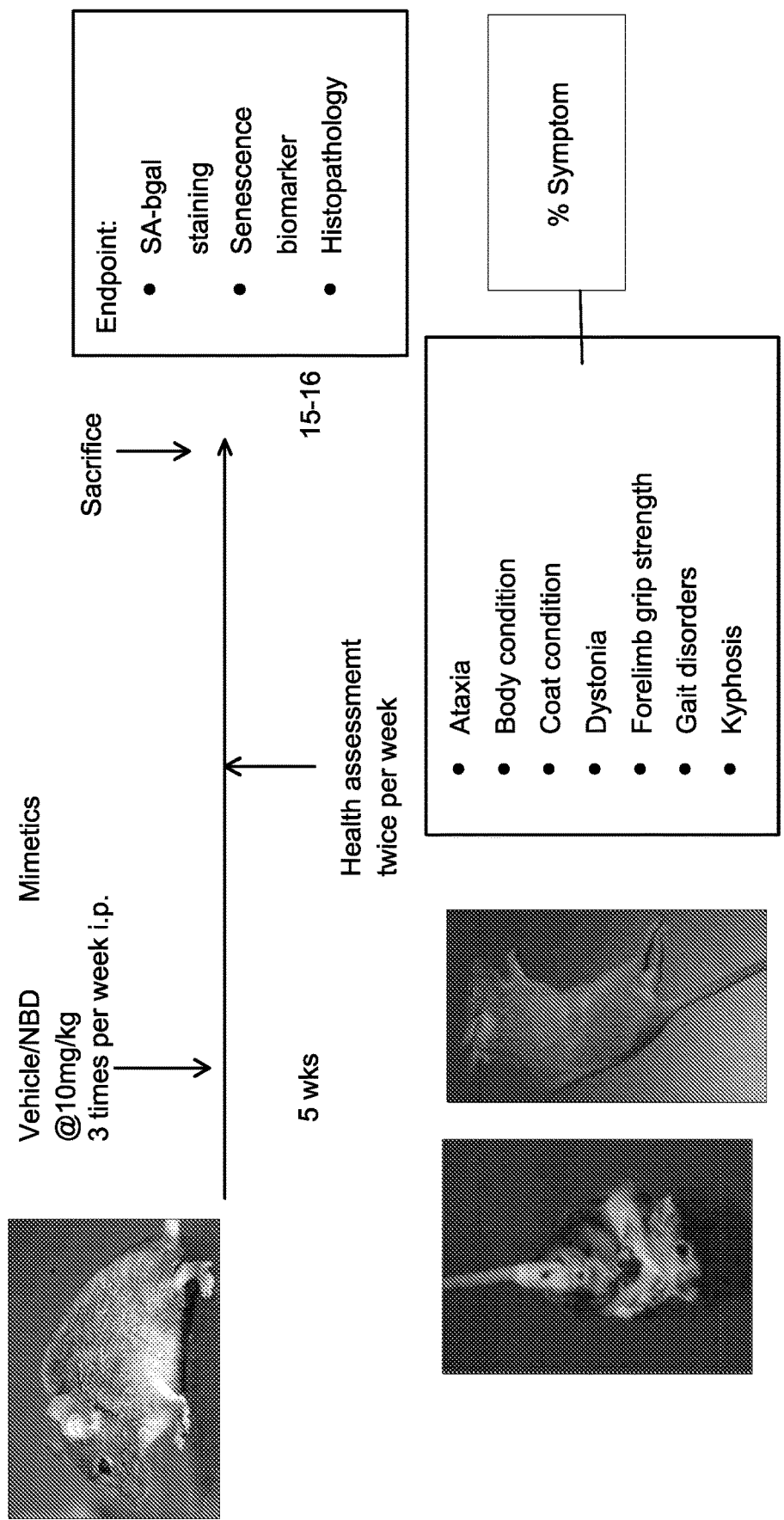
Figure 42:
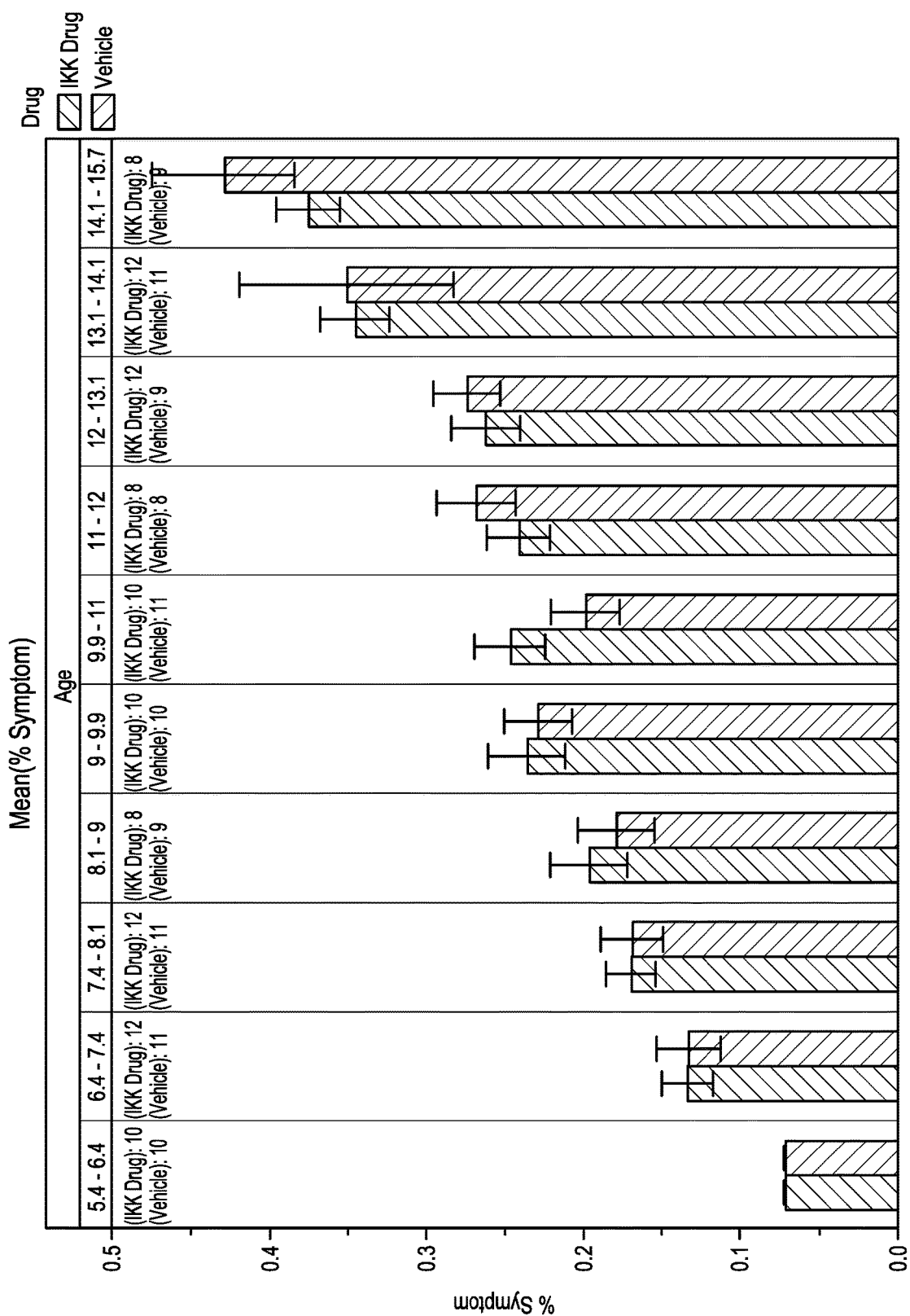
FIG. 42 shows the effect of SR12343 on the overall score of the aging symptoms outlined in FIG. 41 at different ages in Ercc1$^{-/\Delta}$ mice. The NBD mimetic SR12343 reduces the onset of symptoms with chronic treatment of Ercc1$^{-/\Delta}$ mice.
Figure 43:
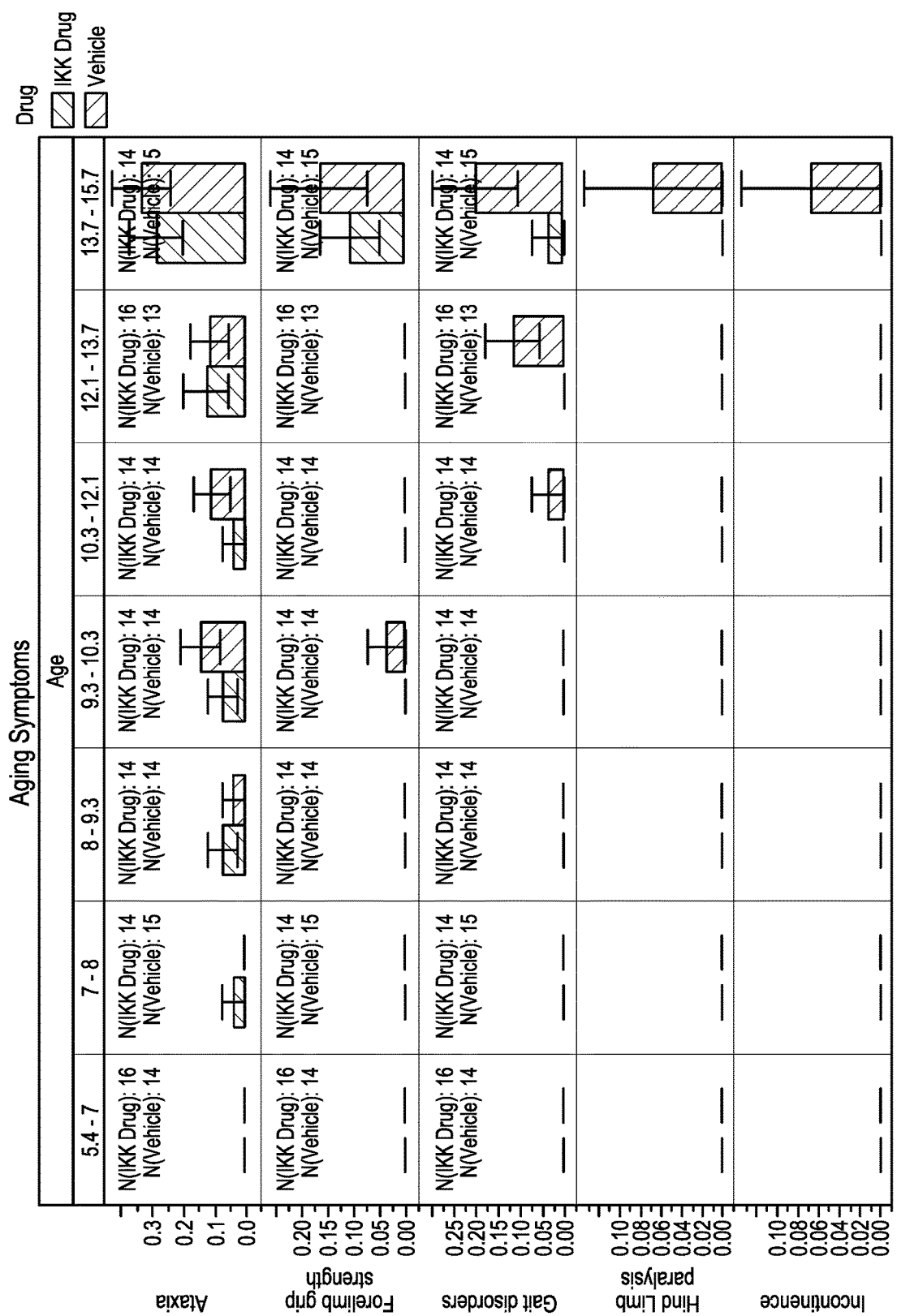
FIG. 43 shows the effect of SR12343 on the specific aging symptoms associated with frailty at different ages in Ercc1$^{-/\Delta}$ mice. The NBD mimetic SR12343 reduces the onset of symptoms associated with frailty with chronic treatment of Ercc1$^{-/\Delta}$ mice.
Figure 44:
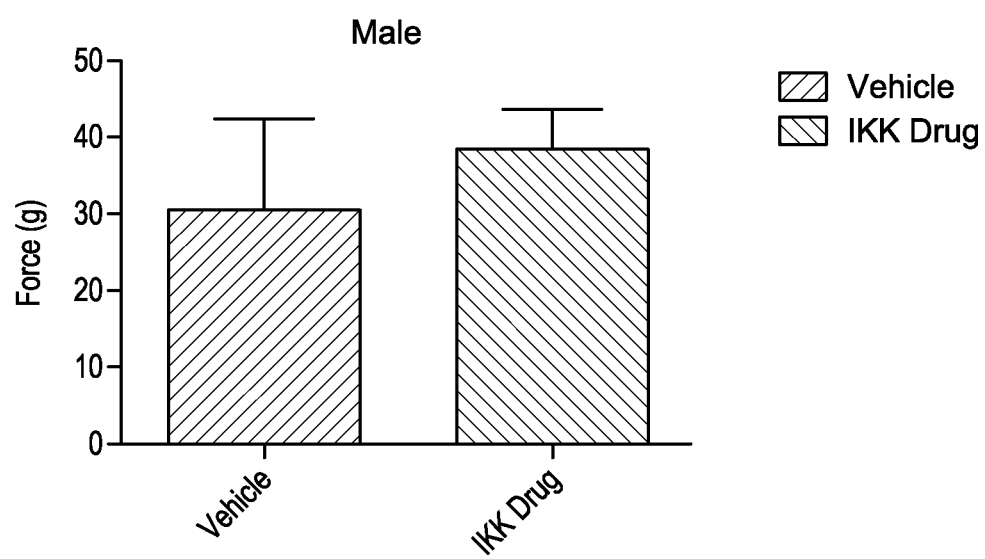
FIG. 44 is a bar graph showing the effect of SR12343 on muscle strength using forelimb strength grip of treated and untreated Ercc1$^{-/\Delta}$ mice. The NBD mimetic SR12343 improves grip strength in male mice with chronic treatment of Ercc1$^{-/\Delta}$ mice.
Figure 45:
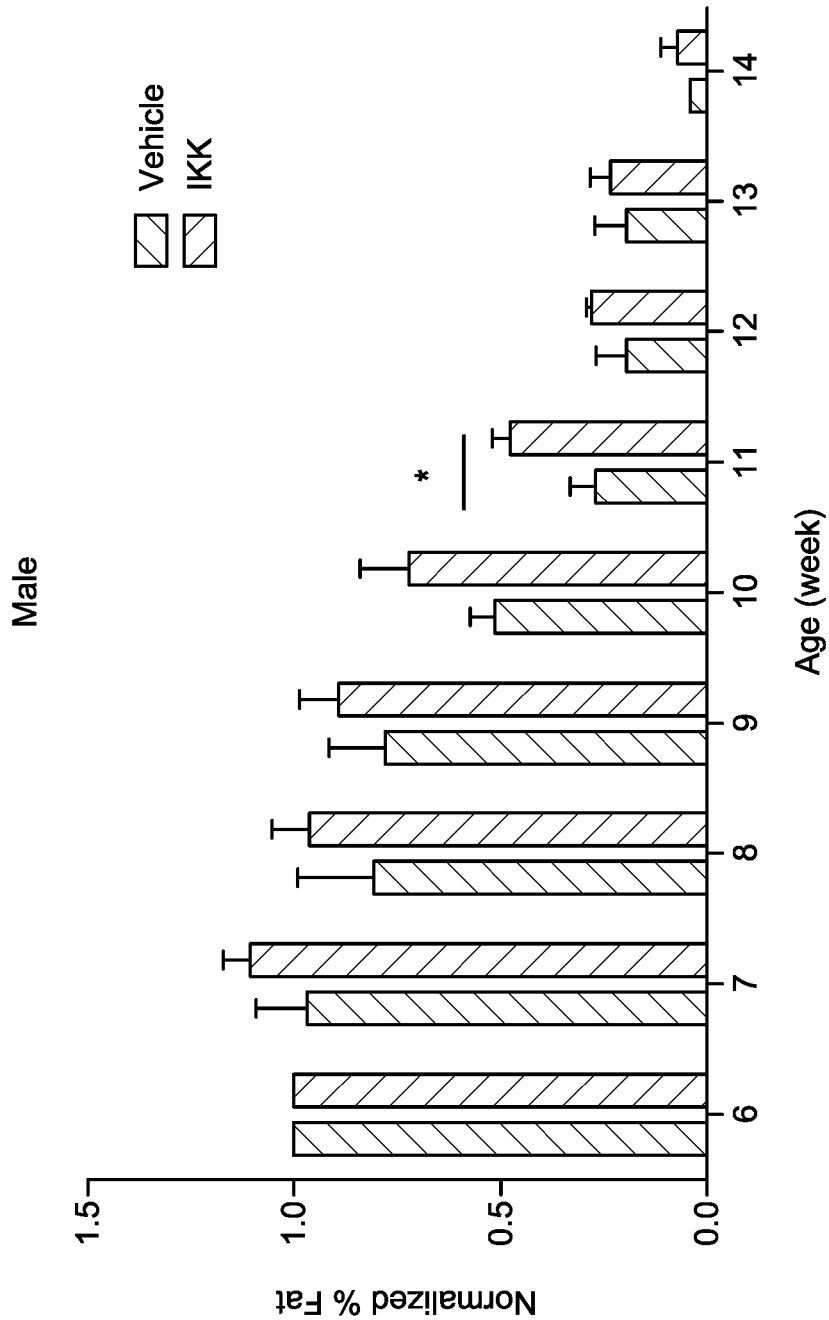
FIG. 45 shows a time course of body fat percentage in Ercc1$^{-/\Delta}$ male mice as determined by nuclear magnetic resonance (NMR) spectroscopy. The NBD mimetic 12343 reduces loss of fat in male mice with chronic treatment of Ercc1$^{-/\Delta}$ mice.
Figure 46:
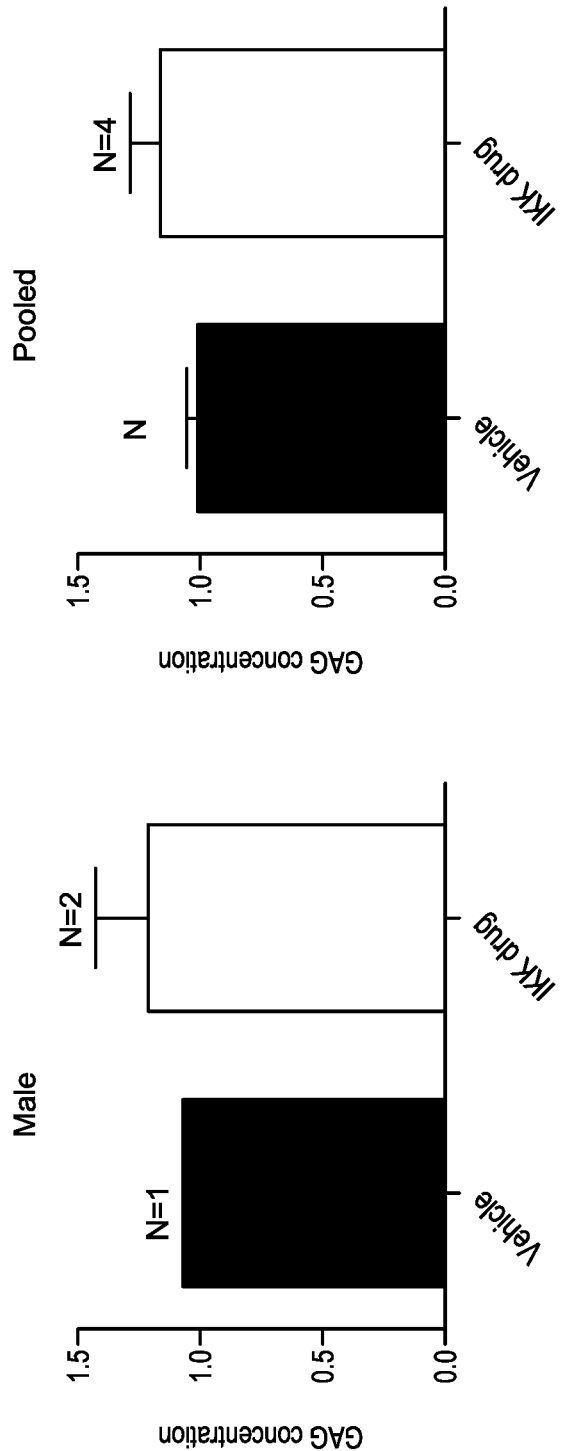
FIG. 46 shows a protective effect of SR12343 on glycosaminoglycan (GAG) concentrations, a marker of disc degeneration, in the intervertebral disc nucleus pulposus (NP). The NBD mimetic SR12343 improves pathology in the intervertebral disc as determined by measuring proteoglycans (GAG) with chronic treatment of Ercc1$^{-/\Delta}$ mice.
Figure 47:
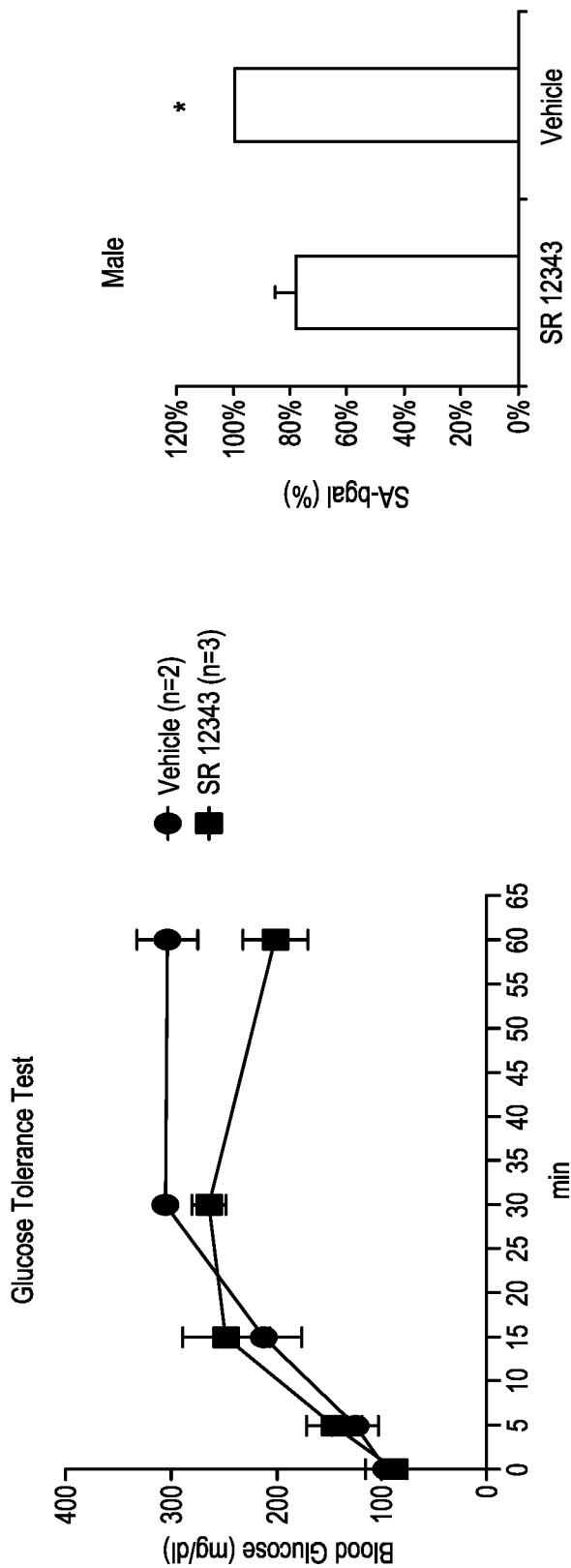
FIG. 47 shows graphic evidence of the effect of SR12343 on improving clearance of blood glucose and reducing senescence in 15 wk-old Ercc1$^{-/\Delta}$ mice treated chronically with the NBD mimetic SR12343. The NBD mimetic 12343 improves clearance of glucose in an oral glucose tolerance test and reduces senescence with chronic treatment of Ercc1$^{-/\Delta}$ mice.
Figure 48:
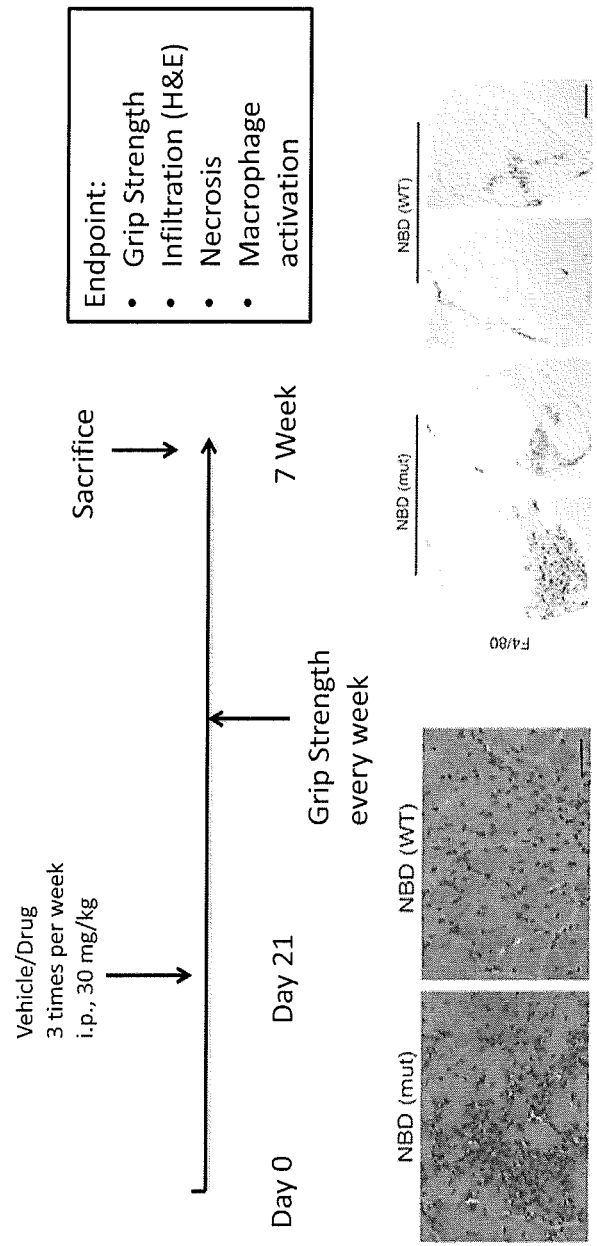
FIG. 48 shows the treatment regimen and endpoints in a mouse model of Duchenne Muscular Dystrophy (DMD)-mdx mice.
Figure 49:
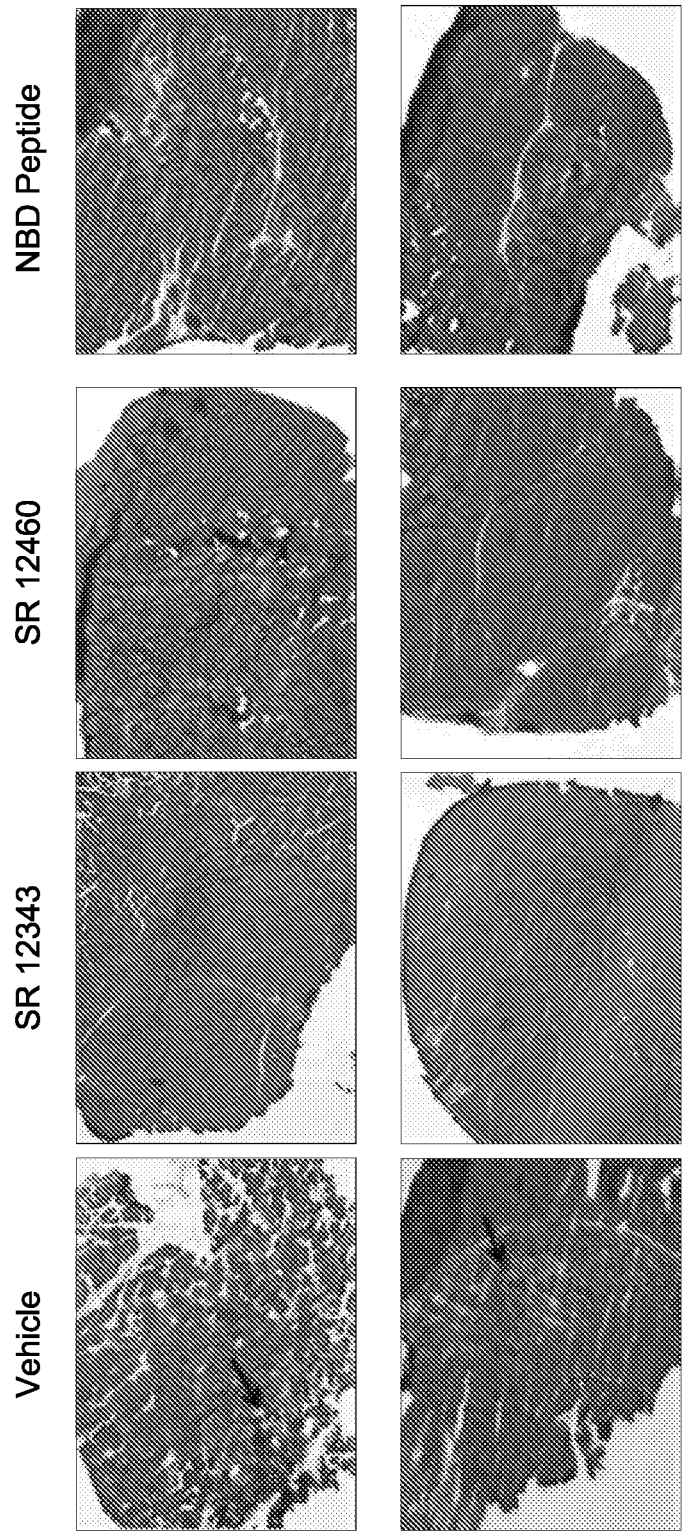
FIG. 49 is a series of microscopic images showing that NBD mimetics improve the histopathology in Tibialis anterior muscle (TA) in mdx mice.
Figure 50:
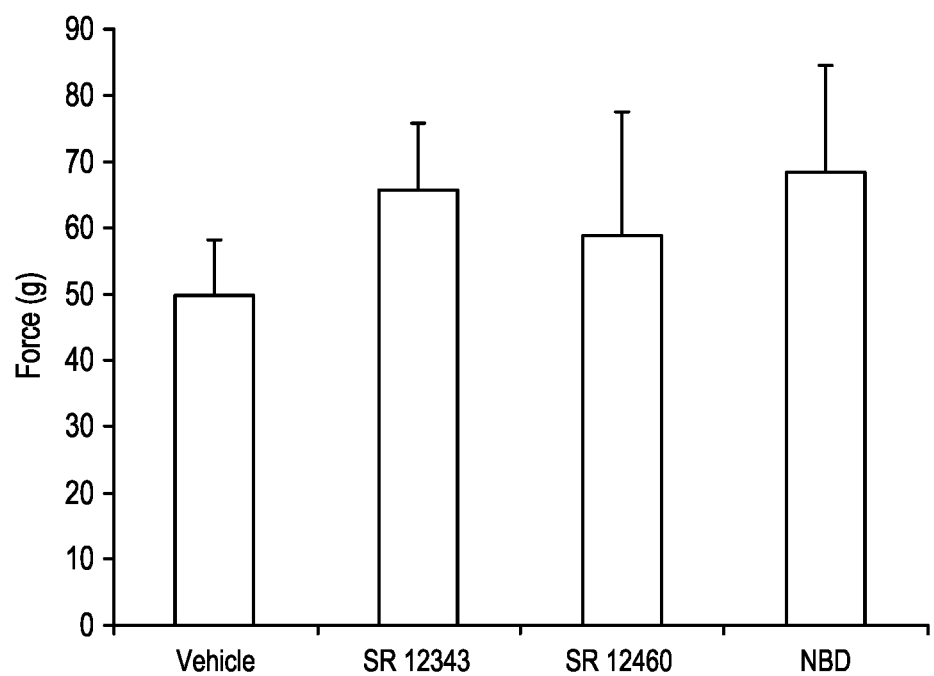
FIG. 50 is a bar graph showing the trend towards increased grip strength in mdx mice treated with NBD mimetics.

FIG. 34 shows the relative expression of TNFα, IκBα, IL-6, and iNOS with compounds SR11481, SR12454, SR12460, and SR12343, versus controls with and without LPS. Raw 264.7 cells were treated with a 50 μM solution of the SR compound for 30 minutes, and then the mRNA was harvested 2 hours after addition of 1 μg/mL LPS. As can be seen, the SR compounds can effect the expression level as seen by the reduction in mRNA.

Taken together these results suggest we have identified small molecules that are able to block the interaction between IKKβ and NEMO to inhibit IKK activation and stimulation of NF-κB transcriptional activity. These drugs could be used to treat a wide range of human diseases safely, effectively and cheaply. Also, it is likely that these drugs could be made orally active. In specific, non-limiting embodiments of the invention, the NBDA is administered alone or optionally with a suitable pharmaceutical carrier.

Signs of Aging that May be Modulated

The present invention may be used to inhibit the development or progression of one or more signs of aging, including, but not limited to, epidermal atrophy, epidermal hyperpigmentation, rhytid (wrinkles), photoaging of the skin, hearing loss, visual impairment, cerebral atrophy, cognitive deficits, trembling, ataxia, cerebellar degeneration, hypertension, renal insufficiency, renal acidosis, incontinence, decreased liver function, hypoalbuminemia, hepatic accumulation of glycogen and triglycerides, anemia, bone marrow degeneration, osteopenia, kyphosis, degenerative joint disease, intervertebral disc degeneration, sarcopenia, muscle weakness, dystonia, increased peroxisome biogenesis, increased apoptosis, decreased cellular proliferation, cachexia, and decreased lifespan. "Inhibiting the development" of a sign of aging means delaying the onset, slowing the progression, or reducing the manifestation, of a sign of aging.

The present invention may be used to improve age-related performance in a geriatric subject. "Improving performance" refers to any aspect of performance, including cognitive performance or physical performance, such as, but not limited to, the ability to be self-sufficient, to take care of (some but not necessarily all) personal needs, to be ambulatory or otherwise mobile, or interaction with others.

The present invention may be used to prolong survival of a geriatric subject, for example, relative to an age-matched, clinically comparable control not treated according to the invention.

Methods of Treatment

Accordingly, in one set of embodiments, the present invention provides for a method of inhibiting one or more signs of aging in a subject in need of such treatment, comprising administering, to the subject, an effective amount of an inhibitor of NF-κB activation. Examples include muscular dystrophy, asthma, inflammatory bowel disease, multiple sclerosis, Parkinson's Disease, arthritis, diabetes, graft versus host disease, accelerated aging, heart ischemia, cancer, UV-induced skin damage, or an age-related pathology.

In a related set of embodiments, the present invention provides for a method of improving age-related performance in a geriatric subject, comprising administering to a subject an effective amount of an inhibitor of NF-κB activation. In another related set of embodiments, the present invention provides for a method of prolonging survival of a geriatric subject, comprising administering, to the subject, an effective amount of an inhibitor of NF-κB activation.

The inhibitor of NF-κB activation may be administered systemically to achieve distribution throughout the body or may be administered to achieve a local effect such as by intra-articular injection or topical treatment. The route of administration may be selected depending on the intended effect. As non-limiting examples, systemic administration, to achieve therapeutic levels throughout the body, may be achieved using an inhibitor suitable for distribution throughout the body, administered via any standard route, including but not limited to oral, intravenous, inhalation, subcutaneous, or intramuscular routes. Non-limiting examples of local administration include, but are not limited to, intrathecal administration to treat central nervous system manifestations of aging, ocular instillation to treat visual disturbances, intramuscular injection may be used to treat muscle wasting, topical administration to prevent or reverse skin aging etc.

Topical formulations may include administering the NF-κB activation inhibitor, optionally comprised in microsphere, microcapsule, or liposome, in a cream, lotion, organic solvent, or aqueous solution.

Inhibitors according to the invention may be administered in a suitable pharmaceutical carrier (e.g. sterile water, normal saline, phosphate buffered saline, etc.). Not by way of limitation, inhibitors may be administered as a solution, as a suspension, in solid form, in a sustained release formulation, in a topical cream formulation, etc. In particular non-limiting examples, an inhibitor may be incorporated into a microcapsule, nanoparticle or liposome.

An effective dose may be calculated by determining the amount needed to be administered to produce a concentration sufficient to achieve the desired effect in the tissue to be treated, taking into account, for example, route of administration, bioavailability, half-life, and the concentration which achieves the desired effect in vitro or in an animal model system, using techniques known in the art.

Non-limiting examples of doses of NBD peptide inhibitors include between 0.1 and 50 mg/kg, or between 1 and 25 mg/kg, or between 2 and 20 mg/kg, or about 2 mg/kg, or about 10 mg/kg, which may be administered daily, at least 5 times a week, at least 3 times a week, at least twice a week, at least once a week, at least twice a month, at least once a month, at least once every three months, or at least once every six months. For the Zinc compounds, we used a concentration of 2 mg/kg.

In any of the foregoing, the dose may be administered daily, at least 5 times a week, at least 3 times a week, at least twice a week, at least once a week, at least twice a month, at least once a month, at least once every three months, or at least once every six months.

EXAMPLES

Compounds of the invention or for practice of methods of the invention, other than NBDA-1 and NBDA-2 (which were purchased from a commercial outlet), were prepared according to the synthetic procedures described herein, in conjunction with ordinary skill and knowledge.

Compounds of the invention can be synthesized according to established literature procedures for analogous compounds and general techniques and reactions well known to persons of ordinary skill in the art.

As shown in General Synthetic Scheme I, below, an appropriately substituted N-acylated aminoheterocycle which contains an alpha-leaving group (Y=halogen) can be coupled with an appropriately substituted arylalkyl amine or alcohol ($X=NH_2$, OH) to give the final product. Alternatively, if Y=OH or Y=NH, and $X=CO_2H$, the two fragments can be coupled using standard peptide coupling conditions (i.e., HATU or EDCI) to afford the final product.

General Synthetic Scheme I

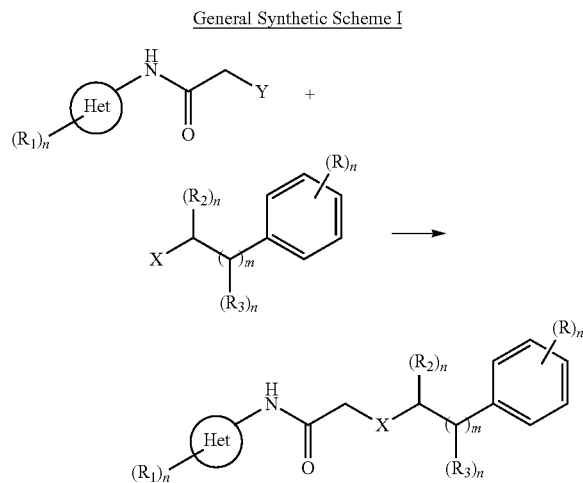

Alternatively, an appropriately substituted heterocyclic amine can be coupled to a substituted alkylaryl acid using standard peptide coupling conditions known to those skilled in the art.

General Synthetic Scheme II

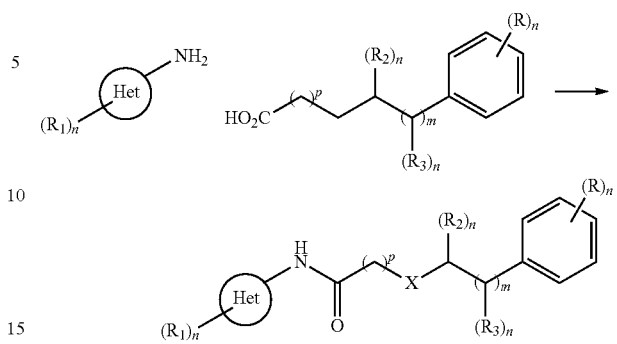

Example 1

2-(3-bromophenethoxy)-N-(pyridin-3-yl)acetamide

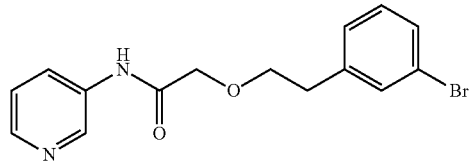 [SMILES: O=C(COCCc1cccc(Br)c1)Nc1cccnc1]

Step 1: tert-butyl 2-(3-bromophenethoxy)acetate

To a solution of 2-(3-bromophenyl)ethanol (2 g, 9.9 mmol) in dry THF (15 mL) under argon at 0° C., was added dropwise NaHMDS 1M in THF (14.8 mL, 14.8 mmol). The reaction mixture was stirred at 0° C. for 30 min. Tert-butyl 2-bromoacetate (3.9 g, 19.9 mmol) in THF (2 mL) was slowly added. The reaction mixture was stirred at rt for 3 h. The completion of the reaction was monitored by anal. HPLC. The reaction was quenched with a solution of $NH_4Cl$, washed with brine and dried over $Na_2SO_4$ and filtered. The filtrate was concentrated in vacuo to obtain the crude product which was purified by flash chromatography (DCM/MeOH) to obtain the title compound.

Step 2: 2-(3-bromophenethoxy)acetic acid

A mixture of tert-butyl 2-(3-bromophenethoxy)acetate (2 g, 6.3 mmol) in TFA/DCM (3 mL) was stirred at rt for 2 h. The completion of the reaction was monitored by anal. HPLC. The solvent was removed to obtain the title compound which is used to the next step without further purification.

Step 3: 2-(3-bromophenethoxy)-N-(pyridin-3-yl)acetamide

To a mixture of 2-(3-bromophenethoxy)acetic acid (30 mg, 0.1 mmol) in DMF (2 mL) was added DIEA (26 mg, 0.2 mmol) and HATU (38 mg, 0.1 mmol). The mixture was stirred for 5 min, and then pyridin-3-amine (9.4 mg, 0.1 mmol) was added. The reaction mixture was stirred at 40° C. overnight. The completion of the reaction was monitored by analytical HPLC. The solvent was removed in vacuo to obtain the crude which was purified by reverse phase prep-HPLC (MeOH/$CH_3CN$/water). ESI-MS (m/z): 336 $[M+H]^+$.

Example 2

2-(3-bromophenethoxy)-N-(pyridin-4-yl)acetamide

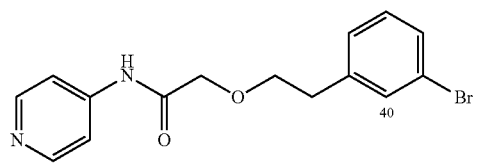 [SMILES: O=C(COCCc1cccc(Br)c1)Nc1ccncc1]

The title compound was prepared following the same general procedure as described in step 3, Example 1, using pyridin-4-amine instead of pyridin-3-amine. ESI-MS (m/z): 336 [M+H]$^+$.

Example 3

2-(3-bromophenethoxy)-N-(6-chloropyridin-2-yl)acetamide

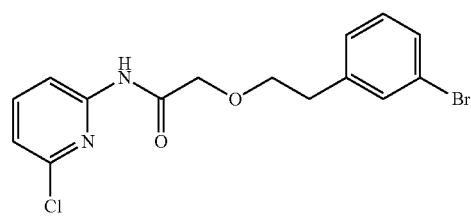 [SMILES: O=C(COCCc1cccc(Br)c1)Nc1cccc(Cl)n1]

The title compound was prepared following the same general procedure as described in step 3, Example 1, using 6-chloropyridin-2-amine instead of pyridin-3-amine. ESI-MS (m/z): 370 [M+H]$^+$.

Example 4

2-(3-bromophenethoxy)-N-(4-chloropyridin-2-yl)acetamide

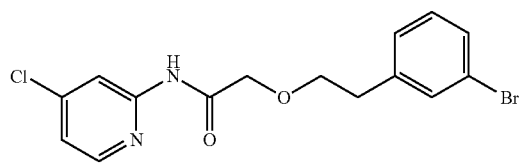 [SMILES: O=C(COCCc1cccc(Br)c1)Nc1cc(Cl)ccn1]

The title compound was prepared following the same general procedure as described in step 3, Example 1, using 4-chloropyridin-2-amine instead of pyridin-3-amine. ESI-MS (m/z): 370 [M+H]$^+$.

Example 5

2-(3-bromophenethoxy)-N-(3-chloropyridin-2-yl)acetamide

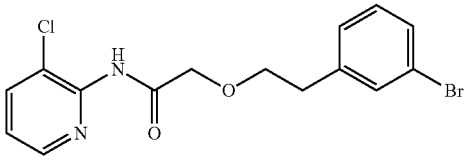 [SMILES: O=C(COCCc1cccc(Br)c1)Nc1ncccc1Cl]

The title compound was prepared following the same general procedure as described in step 3, Example 1, using 3-chloropyridin-2-amine instead of pyridin-3-amine. ESI-MS (m/z): 370 [M+H]$^+$.

Example 6

2-(3-bromophenethoxy)-N-(4-chlorophenyl)acetamide

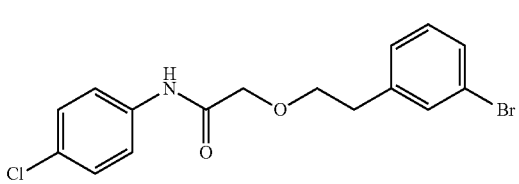 [SMILES: O=C(COCCc1cccc(Br)c1)Nc1ccc(Cl)cc1]

The title compound was prepared following the same general procedure as described in step 3, Example 1, using 4-chloroaniline instead of pyridin-3-amine. ESI-MS (m/z): 369 [M+H]$^+$.

Example 7

2-(3-bromophenethoxy)-N-(6-chloropyridin-3-yl)acetamide

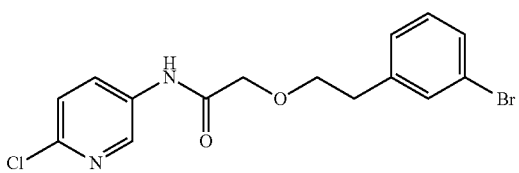 [SMILES: O=C(COCCc1cccc(Br)c1)Nc1ccc(Cl)nc1]

The title compound was prepared following the same general procedure as described in step 3, Example 1, using 6-chloropyridin-3-amine instead of pyridin-3-amine. ESI-MS (m/z): 370 [M+H]$^+$.

Example 8

2-((7-bromonaphthalen-2-yl)oxy)-N-(5-chloropyridin-2-yl)acetamide

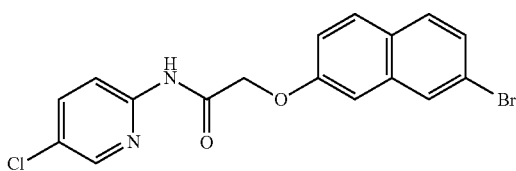 [SMILES: O=C(COc1ccc2ccc(Br)cc2c1)Nc1ccc(Cl)cn1]

Step 1: tert-butyl 2-((7-bromonaphthalen-2-yl)oxy)acetate

The title compound was prepared following the same general procedure as described in step 1, Example 1, using 7-bromonaphthalen-2-ol instead of 2-(3-bromophenyl)ethanol. $^1$H NMR (400 MHz, CDCl$_3$-d$_6$): δ(ppm) 1.46 (s, 9H, 3×CH$_3$), 6.89 (d, J=2.53 Hz, 1H), 7.15 (dd, J=2.53, 8.84 Hz, 1H), 7.33 (dd, J=1.77, 8.84 Hz, 1H), 7.54 (d, J=8.59 Hz, 1H), 7.64 (d, J=9.09 Hz, 1H), 7.79 (d, J=1.77 Hz, 1H).

Step 2: 2-((7-bromonaphthalen-2-yl)oxy)acetic acid

The title compound was prepared following the same general procedure as described in step 2, Example 1, tert-butyl 2-((7-bromonaphthalen-2-yl)oxy)acetate instead tert-butyl 2-(3-bromophenethoxy)acetate.

Step 3: 2-((7-bromonaphthalen-2-yl)oxy)-N-(5-chloropyridin-2-yl)acetamide

The title compound was prepared following the same general procedure as described in step 3, Example 1, using 5-chloropyridin-2-amine instead of pyridin-3-amine. ESI-MS (m/z): 392 [M+H]$^+$.

Example 9

N-(5-chloropyridin-2-yl)-2-((2-methyl-1-(m-tolyl)propan-2-yl)oxy)acetamide

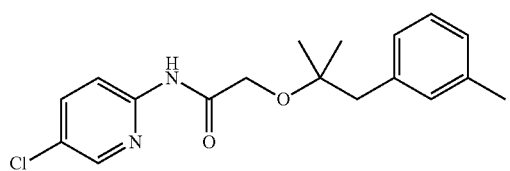 [SMILES: Cc1cccc(CC(C)(C)OCC(=O)Nc2ccc(Cl)cn2)c1]

Step 1: 2-methyl-1-(m-tolyl)propan-2-ol

At 0° C., under argon methyl 2-(m-tolyl)acetate (1 g, 6.1 mmol) in 4 mL of dry THF was slowly added dropwise to 18 mL of a 3M solution of methylmagnesium bromide over 1 h. The reaction mixture was stirred at rt for 30 min and for 3 h under reflux. The reaction mixture was allowed to cool to room temperature and a saturated ammonium chloride solution was slowly added dropwise. The mixture was left to stand overnight. Then 5 mL of 0.5 M HCl solution was added and the mixture was stirred for 5 min. The crude was diluted in AcOEt and washed with brine. The aqueous layer is extracted with AcOEt twice. The organics are combined, dried over Na$_2$SO$_4$ and filtered. The filtrate was concentrated in vacuo to obtain the title compound. $^1$H NMR (400 MHz, CDCl$_3$-d$_6$): δ (ppm) 1.27 (s, 6H, 2×CH$_3$), 2.39 (s, 3H), 2.77 (s, 2H), 7.08 (m, 3H), 7.24 (m, 1H).

Step 2: tert-butyl 2-((2-methyl-1-(m-tolyl)propan-2-yl)oxy)acetate

The title compound was prepared following the same general procedure as described in step 1, Example 1, using 2-methyl-1-(m-tolyl)propan-2-ol instead of 2-(3-bromophenyl)ethanol. $^1$H NMR (400 MHz, CDCl$_3$-d$_6$): δ (ppm) 1.49 (s, 9H, 3×CH$_3$), 2.35 (s, 3H), 2.74 (s, 2H), 3.76 (s, 2H), 7.04 (m, 3H), 7.21 (m, 1H).

Step 3: 2-((2-methyl-1-(m-tolyl)propan-2-yl)oxy)acetic acid

The title compound was prepared following the same general procedure as described in step 2, Example 1, using tert-butyl 2-((2-methyl-1-(m-tolyl)propan-2-yl)oxy)acetate instead of tert-butyl 2-(3-bromophenethoxy)acetate.

Step 4: N-(5-chloropyridin-2-yl)-2-((2-methyl-1-(m-tolyl)propan-2-yl)oxy)acetamide The title compound was prepared following the same general procedure as described in step 3, Example 1, using 5-chloropyridin-2-amine instead of pyridin-3-amine. ESI-MS (m/z): 333 [M+H]$^+$.

Example 10

N-(5-chloropyridin-2-yl)-2-(2-methyl-2-(m-tolyl)propoxy)acetamide

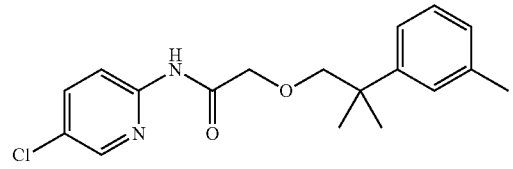 [SMILES: Cc1cccc(C(C)(C)COCC(=O)Nc2ccc(Cl)cn2)c1]

Step 1: methyl 2-methyl-2-(m-tolyl)propanoate

To a solution of methyl 2-(m-tolyl)acetate (1 g, 6.1 mmol) in dry DMF (15 mL) under argon at 0° C., was added tBuOK (2 g, 18.3 mmol). The reaction mixture was stirred at 0° C. for 30 min. Iodomethane (1.9 mL, 30.5 mmol) was slowly added. The reaction mixture was stirred at rt for 3 h. The completion of the reaction was monitored by anal. HPLC. The reaction was quenched with a solution of NH$_4$Cl, washed with brine and dried over Na$_2$SO$_4$ and filtered. The filtrate was concentrated in vacuo to obtain the crude product which was purified by flash chromatography (AcOEt/hexane) to obtain the title compound. $^1$H NMR (400 MHz, CDCl$_3$-d$_6$): δ (ppm) 1.68 (s, 6H, 2×CH$_3$), 2.43 (s, 3H), 3.69 (s, 3H), 7.13 (m, 1H), 7.27 (m, 3H).

Step 2: 2-methyl-2-(m-tolyl)propan-1-ol

The methyl 2-(m-tolyl)acetate is added dropwise to a suspension of LiAlH$_4$ in THF at 0° C. under argon. The reaction mixture is stirred at reflux for 7 h. The reaction mixture was allowed to cool to room temperature and at 0° C. is slowly added water and a 15% aqueous NaOH. saturated ammonium chloride solution was slowly added dropwise. The precipitate was filtered, washed with ether. The filtrate was concentrated in vacuo to obtain the title compound which was used without further purification.

Step 2: tert-butyl 2-(2-methyl-2-(m-tolyl)propoxy)acetate

The title compound was prepared following the same general procedure as described in step 1, Example 1, using 2-methyl-2-(m-tolyl)propan-1-ol instead of 2-(3-bromophenyl)ethanol. $^1$H NMR (400 MHz, CDCl$_3$-d$_6$): δ(ppm) 1.03 (s, 6H, 2×CH$_3$), 1.30 (s, 9H, 3×CH$_3$), 2.15 (s, 3H), 2.54 (s, 2H), 3.38 (s, 2H), 6.85 (m, 3H), 6.98 (m, 1H).

Step 3: 2-(2-methyl-2-(m-tolyl)propoxy)acetic acid

The title compound was prepared following the same general procedure as described in step 2, Example 1, using tert-butyl 2-(2-methyl-2-(m-tolyl)propoxy)acetate instead of tert-butyl 2-(3-bromophenethoxy)acetate.

Step 4: N-(5-chloropyridin-2-yl)-2-(2-methyl-2-(m-tolyl)propoxy)acetamide

The title compound was prepared following the same general procedure as described in step 3, Example 1, using 5-chloropyridin-2-amine instead of pyridin-3-amine. ESI-MS (m/z): 333 [M+H]$^+$.

Example 11

2-(3-bromophenethoxy)-N-(5-chloropyridin-2-yl) propanamide

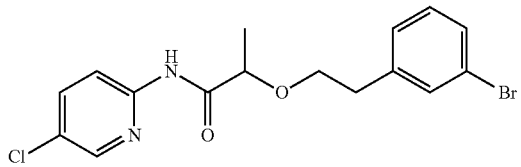

Step 1: tert-butyl 2-(3-bromophenethoxy)propanoate

To a solution of 2-(3-bromophenyl)ethan-1-ol (120 mg, 0.6 mmol) and tert-butyl 2-bromopropanoate (150 mg, 0.72 mmol) in dry DMF (5 mL) under argon, was added NaH (244 mg, 1.8 mmol). The reaction mixture was stirred at reflux. The completion of the reaction was monitored by anal. HPLC. The reaction was quenched with a solution of 0.5N HCl and diluted in AcOEt. The mixture was washed with saturated aqueous NaHCO3, brine and dried over Na$_2$SO$_4$ and filtered. The filtrate was evaporated in vacuo to obtain the title compound.

Step 2: 2-(3-bromophenethoxy)propanoic acid

The title compound was prepared following the same general procedure as described in step 2, Example 1, using tert-butyl 2-(3-bromophenethoxy)propanoate instead of tert-butyl 2-(3-bromophenethoxy)acetate.

Step 3: 2-(3-bromophenethoxy)-N-(5-chloropyridin-2-yl)propanamide

The title compound was prepared following the same general procedure as described in step 3, Example 1, using 5-chloropyridin-2-amine instead of pyridin-3-amine. ESI-MS (m/z): 384 [M+H]$^+$.

Example 12

2-(3-bromophenethoxy)-N-(5-chloropyridin-2-yl)-N-methylacetamide

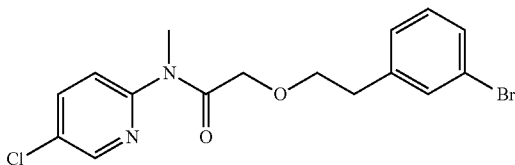 [SMILES: CN(C(=O)COCCc1cccc(Br)c1)c1ccc(Cl)cn1]

To a solution of 2-(3-bromophenethoxy)-N-(6-chloropyridin-3-yl)acetamide (example 7) (30 mg, 0.06 mmol) in dry DMF (5 mL) under argon, was added NaH (4 mg, 0.16 mmol). The reaction mixture was stirred at rt for 30 min and then was added MeI (30 µL, 0.48 mmol). The reaction mixture was stirred at rt overnight. The completion of the reaction was monitored by anal. HPLC. The reaction was quenched with a solution of 0.5N HCl and diluted in AcOEt. The mixture was washed with saturated aqueous NaHCO3, brine and dried over Na$_2$SO$_4$ and filtered. The solvent was removed in vacuo to obtain the crude which was purified by reverse phase prep-HPLC (MeOH/CH$_3$CN/water). ESI-MS (m/z): 384 [M+H]$^+$.

Example 13

5-chloro-N-(1-(3-methylphenethyl)-1H-imidazol-4-yl)pyridin-2-amine

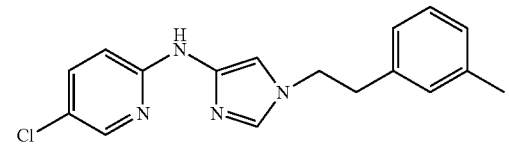 [SMILES: Cc1cccc(CCn2cnc(Nc3ccc(Cl)cn3)c2)c1]

Step 1: 5-chloro-N-(1H-imidazol-4-yl)pyridin-2-amine

The title compound was prepared following the same general procedure as described in step 1, Example 1. $^1$H NMR (400 MHz, CDCl$_3$-d$_6$): δ(ppm) 6.49 (dd, J=0.77, 8.84 Hz, 1H), 7.06 (d, J=1.52, 1H), 7.40 (dd, J=2.53, 8.84 Hz, 1H), 7.61 (d, J=1.26 Hz, 1H), 8.00 (dd, J=0.77, 2.53 Hz, 1H).

Step 2: 5-chloro-N-(1-(3-methylphenethyl)-1H-imidazol-4-yl)pyridin-2-amine

To a solution of 5-chloro-N-(1H-imidazol-4-yl)pyridin-2-amine (50 mg, 0.26 mmol) and 1-(2-bromoethyl)-3-methylbenzene (51 mg, 0.26 mmol) in DMAC (5 mL) under argon, was added Cs₂CO₃ (169 mg, 0.52 mmol). The reaction mixture was stirred at reflux overnight. The completion of the reaction was monitored by anal. HPLC. The reaction was quenched with a solution of 0.5N HCl and diluted in AcOEt. The mixture was washed with saturated aqueous NaHCO3, brine and dried over Na₂SO₄ and filtered. The solvent was removed in vacuo to obtain the crude which was purified by reverse phase prep-HPLC (MeOH/CH₃CN/water). ESI-MS (m/z): 314 [M+H]⁺.

Example 14

N4-(3-chlorobenzyl)-N2-(5-chloropyridin-2-yl)pyrimidine-2,4-diamine

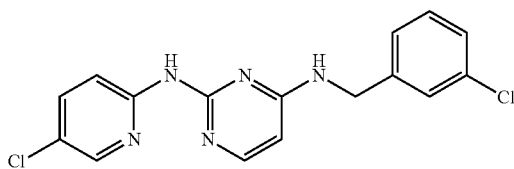 [SMILES: Clc1ccc(Nc2nccc(NCc3cccc(Cl)c3)n2)nc1]

Step 1.
2-chloro-N-(3-chlorobenzyl)pyrimidin-4-amine

To a solution of 2, 4-dichloropyrimidine (600 mg, 4.03 mmol) and isopropanol (10 ml) in a microwave vial, diisopropylethylamine (0.84 ml, 4.83 mmol) and (3-chlorophenyl)methanamine (589 µl, 4.83 mmol) were added. The reaction mixture was heated via a microwave reactor for 1 hr at 100° C. The solvent was removed in vacuo and the crude residue was purified by chromatography on silica gel (Hex/EtOAc) to give the title compound. ESI-MS (m/z): 254 [M]⁺

Step 2. N4-(3-chlorobenzyl)-N2-(5-chloropyridin-2-yl)pyrimidine-2,4-diamine

A mixture of 2-chloro-N-(3-chlorobenzyl)pyrimidin-4-amine (50 mg, 197 µmol), 5-chloropyridin-2-amine (25 mg, 197 µmol), Pd(OAc)₂ (9 mg, 40 µmol), xantphos (34 mg, 59 µmol), and Cs₂CO₃ (192 mg, 590 µmol) in dioxane (2 ml) was purged with argon, and then stirred at 100° C. overnight. The reaction was cooled, filtered through a pad of silica gel and concentrated in vacuo. The crude residue was then purified by reverse-phase preparative HPLC to afford the title compound. ESI-MS (m/z): 346, 348 [M]⁺, [M+2]⁺.

Example 15

N4-(3-chlorobenzyl)-N6-(5-chloropyridin-2-yl)pyrimidine-4,6-diamine

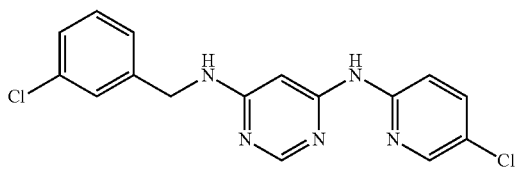 [SMILES: Clc1ccc(Nc2cc(NCc3cccc(Cl)c3)ncn2)nc1]

Step 1.
6-chloro-N-(5-chloropyridin-2-yl)pyrimidin-4-amine

A mixture of 4,6-dichloropyrimidine (1.00 g, 6.71 mmol), 5-chloropyridin-2-amine (863 mg, 6.71 mmol), Pd(OAc)₂ (60 mg, 269 µmol), BINAP (250 mg, 402 µmol), and Na₂CO₃ (2.85 g, 26.9 mmol) in dioxane (10 ml) was purged with argon, and then stirred at 100° C. overnight. The reaction was cooled, filtered through a pad of silica gel. The crude was dissolved in EtOAc and washed with sat'd NaHCO₃, brine and then dried (MgSO₄). The crude residue was then purified by chromatography on silica gel (Hex/EtOAc) to give the title compound. ESI-MS (m/z): 241 [M]⁺

Step 2. N4-(3-chlorobenzyl)-N6-(5-chloropyridin-2-yl)pyrimidine-4,6-diamine

To a solution of 6-chloro-N-(5-chloropyridin-2-yl)pyrimidin-4-amine (50 mg, 207 µmol) and ethanol (2 ml) in a microwave vial, diisopropylethylamine (108 µl, 622 µmol) and (3-chlorophenyl)methanamine (88 mg, 622 µmol) were added. The reaction mixture was heated via a microwave reactor for 1 hr at 120° C. The reaction was cooled and concentrated in vacuo. The crude reaction mixture was then purified by reverse-phase preparative HPLC to afford the title compound. ESI-MS (m/z): 346, 348 [M]⁺, [M+2]⁺.

Example 16

N-(5-chloropyridin-2-yl)-2-(3,5-difluorophenethoxy)acetamide

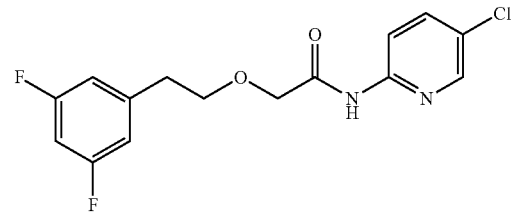 [SMILES: O=C(COCCc1cc(F)cc(F)c1)Nc1ccc(Cl)cn1]

Step 1. 2-(3,5-difluorophenyl)ethan-1-ol 2-(3,5-difluorophenyl)acetic acid (250 mg, 1.45 mmol) was dissolved in 10 ml of THF and cooled to 0° C. 1M Borane THF complex solution (2.18 ml, 2.18 mmol) was then added dropwise over 15 mins. The reaction was then allowed to warm to room temperature overnight and then quenched with water at 0° C. The reaction mixture was diluted with EtOAc and washed with water, brine, dried (MgSO₄), and concentrated. The crude residue was concentrated in vacuo to give the title compound as a clear oil which was used without further purification. ¹H NMR (CHCl₃, 400 MHz) δ 6.68 (m, 2H), 6.55 (m, 1H), 3.75 (t, J=6.5 Hz, 2H), 2.74 (t, J=6.5 Hz, 2H).

Step 2. 2-bromo-N-(5-chloropyridin-2-yl)acetamide 2-bromoacetyl chloride (1.18 ml, 9.33 mmol) and 5-chloropyridin-2-amine (1.20 g, 9.33 mmol) in 12 ml of dichloroethane were combined in a microwave tube. The reaction mixture was heated via a microwave reactor for 15 minutes at 85° C. The solvent was removed in vacuo. The crude was dissolved in EtOAc and washed with sat'd NaHCO₃, brine and then dried (MgSO₄). The crude residue was then purified by chromatography on silica gel (Hex/EtOAc) to give the title compound as a white powder. ESI-MS (m/z): 249, 251 [M]⁺, [M+2]⁺.

Step 3. N-(5-chloropyridin-2-yl)-2-(3,5-difluorophenethoxy)acetamide 2-(3,5-difluorophenyl)ethan-1-ol (20 mg, 126 μmol) was dissolved in 1 ml of DMF and cooled to 0° C. NaH (3.03 mg, 126 μmol) was then added and stirred to RT over 30 mins. 2-bromo-N-(5-chloropyridin-2-yl)acetamide (32 mg, 126 μmol) was then added and the reaction slowly heated to 80° C. for 2 hours. The reaction was cooled to RT and the solvent was removed in vacuo. The crude residue was then purified by reverse-phase preparative HPLC to afford the title compound. ESI-MS (m/z): 327 [M+1]$^+$.

Example 17

2-(3,5-bis(trifluoromethyl)phenethoxy)-N-(5-chloropyridin-2-yl)acetamide

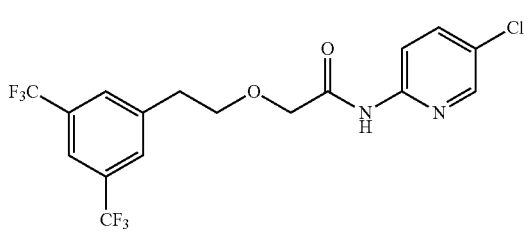 [SMILES: O=C(COCCc1cc(C(F)(F)F)cc(C(F)(F)F)c1)Nc1ccc(Cl)cn1]

The title compound was synthesized following the same general protocol as described for N-(5-chloropyridin-2-yl)-2-(3,5-difluorophenethoxy)acetamide in Example 16, starting with 2-(3,5-bis(trifluoromethyl)phenyl)acetic acid. ESI-MS (m/z): 427 [M+1]$^+$

Example 18

N-(5-chloropyridin-2-yl)-2-(3,5-dibromophenethoxy)acetamide

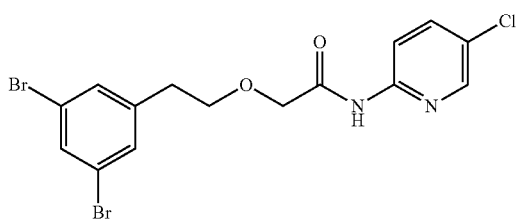 [SMILES: O=C(COCCc1cc(Br)cc(Br)c1)Nc1ccc(Cl)cn1]

The title compound was synthesized following the same general protocol as described for N-(5-chloropyridin-2-yl)-2-(3,5-difluorophenethoxy)acetamide in Example 16, starting with 2-(3,5-dibromophenyl)acetic acid. ESI-MS (m/z): ESI-MS (m/z): 448, 450 [M]$^+$, [M+2]$^+$.

Example 19

N-(3-bromophenethyl)-2-((5-chloropyridin-2-yl)amino)-2-methylpropanamide

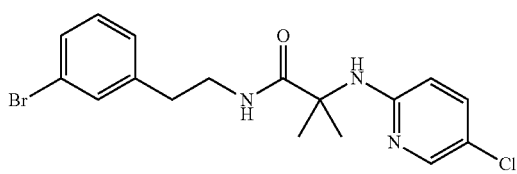 [SMILES: CC(C)(Nc1ccc(Cl)cn1)C(=O)NCCc1cccc(Br)c1]

Step 1. 2-bromo-N-(3-bromophenethyl)-2-methylpropanamide

To a solution of 2-(3-bromophenyl)ethan-1-amine (100 mg, 500 μmol) in DCM was added DIPEA (261 μl, 1.50 mmol) followed by 2-bromo-2-methylpropanoic acid (83 mg, 500 μmol) and HATU (190 mg, 500 μmol). The reaction was allowed to stir at room temperature for 1 hr then concentrated in vacuo. The crude residue was taken up in EtOAc and washed with sat aq. NaHCO$_3$, 1M HCl, brine, dried (MgSO$_4$), and concentrated to yield the title product without further purification. ESI-MS (m/z): 349, 350 [M]$^+$, [M+2]$^+$.

Step 2. N-(3-bromophenethyl)-2-((5-chloropyridin-2-yl)oxy)-2-methylpropanamide 2-bromo-N-(3-bromophenethyl)-2-methylpropanamide (45 mg, 129 μmol) and 5-chloropyridin-2-amine (16.5 mg, 129 μmol) were dissolved in a mixture of 50% aqueous NaOH/DCM (4 ml) and stirred. Tetra-n-butylammonium bromide was then added and the reaction stirred at room temperature for 2 hours. The Aqueous phase was discarded and the organic phase was immediately purified by reverse-phase preparative HPLC to afford the title compound. ESI-MS (m/z): 398 [M+2]$^+$.

Example 20

3-bromophenethyl 2-((5-chloropyridin-2-yl)oxy)-2-methylpropanoate

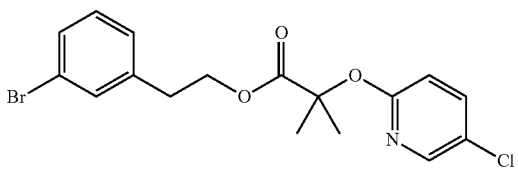 [SMILES: CC(C)(Oc1ccc(Cl)cn1)C(=O)OCCc1cccc(Br)c1]

The title compound was synthesized following the same general protocol as described for 3N-(3-bromophenethyl)-2-((5-chloropyridin-2-yl)oxy)-2-methylpropanamide in example 19 using 5-chloropyridin-2-ol. ESI-MS (m/z): 397, 399 [M]$^+$, [M+2]$^+$.

Example 21

N-(2-((5-chloropyridin-2-yl)amino)ethyl)-2-(3,5-difluorophenyl)acetamide

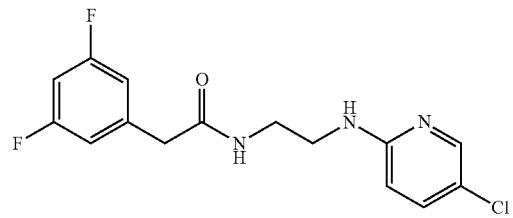 [SMILES: O=C(Cc1cc(F)cc(F)c1)NCCNc1ccc(Cl)cn1]

Step 1. N1-(5-chloropyridin-2-yl)ethane-1,2-diamine 5-chloro-2-fluoropyridine (325 μl, 2.04 mmol) was dissolved in 4 ml of ethane-1,2-diamine and stirred at 80° C. for 4 hr. The ethane-1,2-diamine was then removed in vacuo to yield the title compound as a red-brown oil. ESI-MS (m/z): 172 [M+1]⁺.

Step 2. N-(2-((5-chloropyridin-2-yl)amino)ethyl)-2-(3,5-difluorophenyl)acetamide To a solution of N1-(5-chloropyridin-2-yl)ethane-1,2-diamine (25 mg, 146 µmol) in DCM was added DIPEA (76 µl, 434 µmol) followed by 2-(3,5-difluorophenyl)acetic acid (25 mg, 146 µmol) and HATU (55 mg, 146 µmol). The reaction was allowed to stir at room temperature for 1 hr then concentrated in vacuo. The crude residue was taken up in EtOAc and washed with sat aq. NaHCO₃, 1M HCl, brine, dried (MgSO₄), concentrated and was immediately purified by reverse-phase preparative HPLC to afford the title compound. ESI-MS (m/z): 326 [M+1]⁺.

Example 22

N-(5-chloropyridin-2-yl)-2-((3,5-difluorophenethyl)amino)acetamide

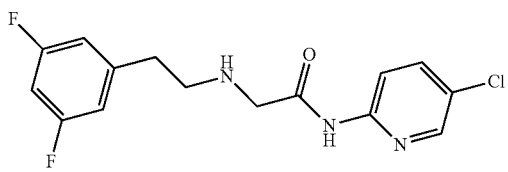 [SMILES: O=C(CNCCc1cc(F)cc(F)c1)Nc1ccc(Cl)cn1]

2-chloro-N-(5-chloropyridin-2-yl)acetamide (50 mg, 244 µmol), 2-(3,5-difluorophenyl)ethan-1-amine (39 µl, 292 µmol), K₂CO₃ (67 mg, 488 µmol), and KI (4 mg, 24 µmol) were dissolved in 2 ml of acetonitrile and stirred at reflux for 5 hr. The solvent was removed in vacuo and was taken up in EtOAc and washed with sat aq. NaHCO₃, brine, dried (MgSO₄), concentrated and was immediately purified by reverse-phase preparative HPLC to afford the title compound. ESI-MS (m/z): 326 [M+1]⁺.

Example 23 2-((5-chloropyridin-2-yl)amino)-N-(3,5-difluorophenethyl)acetamide

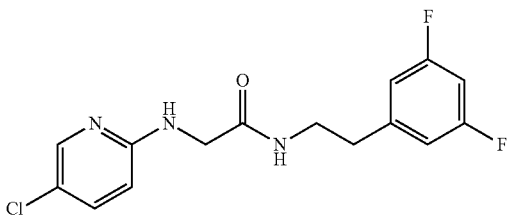 [SMILES: O=C(CNc1ccc(Cl)cn1)NCCc1cc(F)cc(F)c1]

Step 1. 2-bromo-N-(3,5-difluorophenethyl)acetamide

To a solution of 2-(3,5-difluorophenyl)ethan-1-amine (67 µl, 504 µmol) in DCM was added DIPEA (262 µl, 1.51 mmol) followed by 2-bromoacetic acid (70 mg, 503 µmol) and HATU (191 mg, 503 µmol). The reaction was allowed to stir at room temperature for 1 hr then concentrated in vacuo. The crude residue was taken up in EtOAc and washed with sat aq. NaHCO₃, 1M HCl, brine, dried (MgSO₄), and concentrated to yield the title product without further purification. ESI-MS (m/z): 279 [M+1]⁺.

Step 2. 2-((5-chloropyridin-2-yl)amino)-N-(3,5-difluorophenethyl)acetamide 2-bromo-N-(3,5-difluorophenethyl)acetamide (65 mg, 234 µmol), 5-chloropyridin-2-amine (45 mg, 350 µmol) and DIPEA (122 µl, 701 µmol) was dissolved in ACN and stirred under reflux overnight. The solvent was removed in vacuo and was taken up in EtOAc and washed with sat aq. NaHCO₃, brine, dried (MgSO₄), concentrated and was immediately purified by reverse-phase preparative HPLC to afford the title compound. ESI-MS (m/z): 326 [M+1]⁺.

Example 24

N-(5-Chloropyridin-2-yl)-6-((3-(trifluoromethyl)phenyl)amino)picolinamide

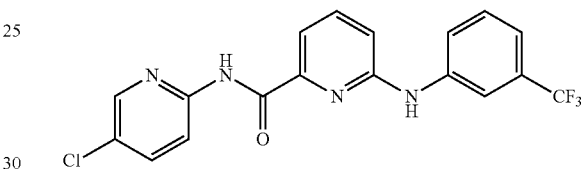

Step 1. Methyl 6-bromopicolinate

To a solution of 6-bromopicolinic acid (300 mg, 1.49 mmol) in DMF (3 mL) were added K₂CO₃ (411 mg, 2.98 mmol) and methyl iodide (186 µL, 2.98 mmol). The resultant mixture was stirred at room temperature for 16 h and then partitioned between EtOAc (20 mL) and H₂O (20 mL). The organic layer was separated, washed with brine (20 mL), dried over Na₂SO₄, filtered and the solvent evaporated under reduced pressure to yield the title compound (310 mg, 97%) as a white solid: LC-MS$_T$: $R_t$=4.38 min; MS (ESI) m/z 216.12 (M+H)⁺.

Step 2. Methyl 6-((3-(trifluoromethyl)phenyl)amino)picolinate

A suspension of methyl 6-bromopicolinate (300 mg, 1.40 mmol), 3-(trifluoromethyl)aniline (192 µL, 1.54 mmol), Cs₂CO₃ (1.37 g, 4.20 mmol), tris(dibenzylideneacetone)dipalladium (256 mg, 0.28 mmol) and Xantphos (243 mg, 0.42 mmol) in 1,4-dioxane (10 mL) was stirred at 90° C. for 16 h. The suspension was cooled to room temperature and filtered through a pad of celite. The filtrate was diluted with EtOAc (20 mL), washed with brine (20 mL), dried over Na₂SO₄, filtered and the solvent evaporated under reduced pressure to yield the title compound (150 mg, 36%) as a brown solid: LC-MS$_T$: $R_t$=5.98 min; MS (ESI) m/z 297.10 (M+H)⁺.

Step 3. 6-((3-(Trifluoromethyl)phenyl)amino)picolinic acid

To a solution of methyl 6-((3-(trifluoromethyl)phenyl)amino)picolinate (140 mg, 0.47 mmol) in THF (3 mL) and H₂O (1 mL) was added LiOH.H₂O (99 mg, 2.35 mmol). The resultant mixture was stirred at room temperature for 16 h and then partitioned between EtOAc (20 mL) and 1N aq. HCl (20 mL). The organic layer was separated, dried over $Na_2SO_4$, filtered and the solvent evaporated under reduced pressure to yield the title compound (112 mg, 84%) as a brown solid: LC-MS$_T$: $R_t$=5.03 min; MS (ESI) m/z 283.06 (M+H)$^+$.

Step 4. N-(5-Chloropyridin-2-yl)-6-((3-(trifluoromethyl)phenyl)amino)picolinamide To a solution of 6-((3-(trifluoromethyl)phenyl)amino)picolinic acid (50 mg, 0.18 mmol) in DMF (3 mL) were added 5-chloropyridin-2-amine (26 mg, 0.20 mmol), HATU (84 mg, 0.22 mmol) and DIPEA (94 µL, 0.54 mmol). The resultant mixture was stirred at room temperature for 48 h and then partitioned between EtOAc (20 mL) and $H_2O$ (20 mL). The organic phase was separated, washed with brine (20 mL), dried over $Na_2SO_4$, filtered and the solvent evaporated under reduced pressure. The residue was purified by silica gel flash-column chromatography, with hexanes/EtOAc (8:2) as the eluent, to yield the title compound (59 mg, 85%) as a brown solid: LC-MS$_A$: $R_t$=4.166 min; MS (ESI) m/z 393.2 (M+H)$^+$.

Example 25

2-((5-chloropyridin-2-yl)amino)-2-oxoethyl 2-phenylacetate

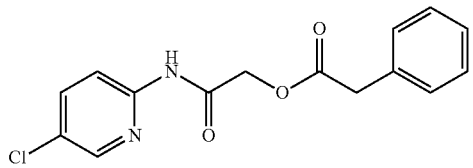 [SMILES: O=C(COC(=O)Cc1ccccc1)Nc1ccc(Cl)cn1]

Step 1. 2-chloro-N-(5-chloropyridin-2-yl)acetamide

To a solution of 5-chloropyridin-2-amine (1.3 g) in 1,2-dichloroethane (3 mL) was added chloroacetylchloride (1.1 eq). The reaction was heated in a microwave reactor at 85° C. for 10 min, and then cooled. The title compound was filtered, washed with dichloromethane, dried in vacuo, and used without further purification.

Step 2. 2-((5-chloropyridin-2-yl)amino)-2-oxoethyl 2-phenylacetate

To a solution of 2-chloro-N-(5-chloropyridin-2-yl)acetamide (50 mg) in DMF (1 mL) was added phenylacetic acid (34 mg), triethylamine (2eq), and potassium iodide (41 mg). The reaction mixture was warmed to 70° C. for 1 h. The reaction was cooled to 25° C. and diluted with EtOAc and washed with water, 1M HCl, brine, dried (MgSO$_4$), and concentrated to yield the crude product. Purification by chromatography on silica gel (EtOAc/hexanes) provided the title compound. ESI-MS (m/z): 305 [M+1]$^+$.

Example 26

2-((5-chloropyridin-2-yl)amino)-2-oxoethyl 2-(2-fluorophenyl)acetate

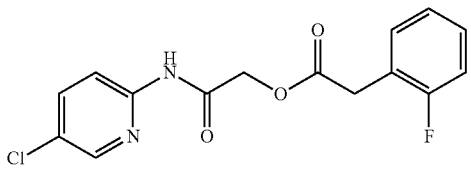 [SMILES: O=C(COC(=O)Cc1ccccc1F)Nc1ccc(Cl)cn1]

The title compound was synthesized following the same general protocol as described in Example 25, starting with 2-chloro-N-(5-chloropyridin-2-yl)acetamide and 2-(2-fluorophenyl)acetic acid. ESI-MS (m/z): 323 [M+1]$^+$ Example 27

2-((5-chloropyridin-2-yl)amino)-2-oxoethyl 2-(3-fluorophenyl)acetate

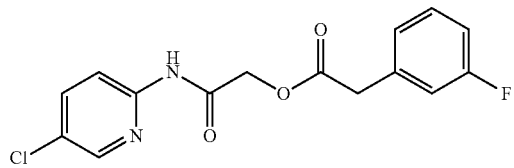 [SMILES: O=C(COC(=O)Cc1cccc(F)c1)Nc1ccc(Cl)cn1]

The title compound was synthesized following the same general protocol as described in Example 25, starting with 2-chloro-N-(5-chloropyridin-2-yl)acetamide and 2-(3-fluorophenyl)acetic acid. ESI-MS (m/z): 323 [M+1]$^+$ Example 28

2-((5-chloropyridin-2-yl)amino)-2-oxoethyl 2-(4-fluorophenyl)acetate

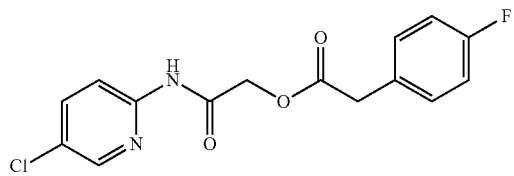 [SMILES: O=C(COC(=O)Cc1ccc(F)cc1)Nc1ccc(Cl)cn1]

The title compound was synthesized following the same general protocol as described in Example 25, starting with 2-chloro-N-(5-chloropyridin-2-yl)acetamide and 2-(4-fluorophenyl)acetic acid. ESI-MS (m/z): 323 [M+1]$^+$ Example 29

2-((5-chloropyridin-2-yl)amino)-2-oxoethyl 2-(3,5-difluorophenyl)acetate

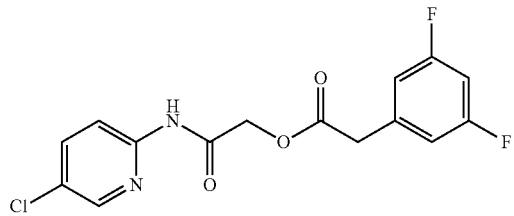 [SMILES: O=C(COC(=O)Cc1cc(F)cc(F)c1)Nc1ccc(Cl)cn1]

The title compound was synthesized following the same general protocol as described in Example 25, starting with 2-chloro-N-(5-chloropyridin-2-yl)acetamide and 2-(3,5-difluorophenyl)acetic acid. ESI-MS (m/z): 341 [M+1]+

Example 30

2-((5-chloropyridin-2-ylamino)-2-oxoethyl 2-(4-(methylsulfonyl)phenyl)acetate

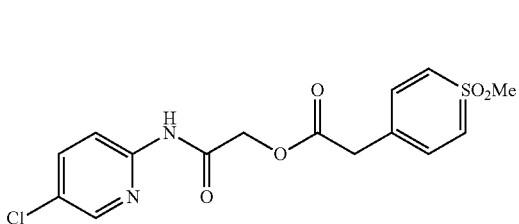

The title compound was synthesized following the same general protocol as described in Example 25, starting with 2-chloro-N-(5-chloropyridin-2-yl)acetamide and 2-(4-(methylsulfonyl)phenyl)acetic acid. ESI-MS (m/z): 383 [M+1]+

Example 31

N-(5-chloropyridin-2-yl)-2-(2-(4-(methylsulfonyl)phenyl)acetamido)acetamide

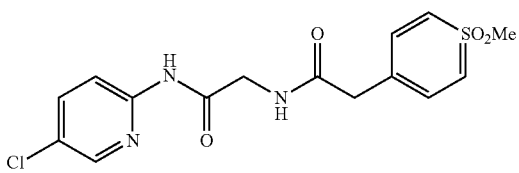

To a solution of 2-amino-N-(5-chloropyridin-2-yl)acetamide in DMF (1 mL) was added Hunig's base (2eq) followed by 1-(1H-benzo[d][1,2,3]triazol-1-yl)-2-(4-(methylsulfonyl)phenyl)ethanone (1.1 eq). The reaction was heated in a microwave reactor at 100° C. for 1 h, and then cooled. Purification by chromatography on silica gel (EtOAc/hexanes) provided the title compound. ESI-MS (m/z): 382 [M+1]+.

Example 32

2-((3-bromophenethyl)amino)-N-(5-chloropyridin-2-yl)acetamide

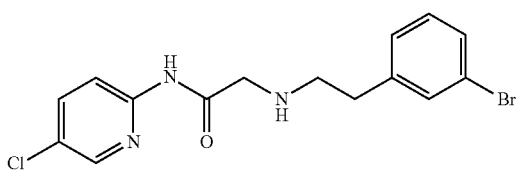 [SMILES: O=C(CNCCc1cccc(Br)c1)Nc1ccc(Cl)cn1]

The title compound was synthesized following the same general protocol as described in Example 22, starting with 2-chloro-N-(5-chloropyridin-2-yl)acetamide and 2-(3-bromophenyl)ethanamine. ESI-MS (m/z): 368, 370 [M+1]+

Example 33

2-((3-bromophenethyl)(cyclopropylmethyl)amino)-N-(5-chloropyridin-2-yl)acetamide

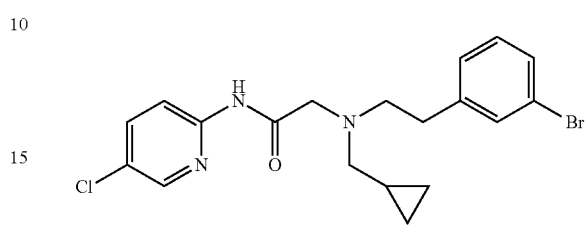

To a solution of the product from Example 32 (0.05 mmol) in DMF (1 mL) was added $K_2CO_3$ (2eq) followed by cyclopropylmethylbromide (14 mg). The reaction was warmed to 70° C. for 12 h, and then cooled. The crude residue was taken up in EtOAc and washed with sat aq. $NaHCO_3$, 1M HCl, brine, dried ($MgSO_4$), and concentrated to yield the title product which was purified by chromatography on silica gel (EtOAc/hexanes) to afford the title compound. ESI-MS (m/z): 422 [M+1]+.

Example 34 tert-butyl (2-((5-chloropyridin-2-yl)amino)-2-oxoethyl)carbamate

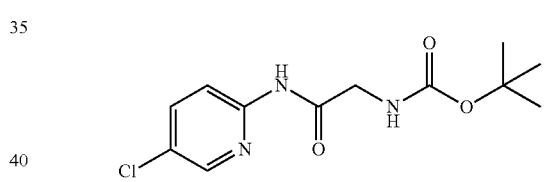

To a solution of 5-chloropyridin-2-amine (257 mg, 2 mmol) and N-BOC-glycine (420 mg, 2.4 mmol) in DMF (10 mL) was added diisoporpylethylamine (4 mmol) followed by HATU (3 mmol). The reaction was stirred at room temperature for 8 h, and then warmed to 50° C. for 16 h. The reaction was cooled to 25° C. and then concentrated in vacuo. The crude residue was taken up in EtOAc and washed with sat aq. $NaHCO_3$, 1M HCl, brine, dried ($MgSO_4$), and concentrated to yield the title product which was used without further purification. ESI-MS (m/z): 286 [M+1]+.

Example 35

2-amino-N-(5-chloropyridin-2-yl)acetamide

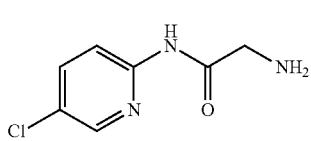 [SMILES: NCC(=O)Nc1ccc(Cl)cn1]

To a solution of tert-butyl (2-((5-chloropyridin-2-yl)amino)-2-oxoethyl)carbamate from the previous step in $CH_2Cl_2$ (5 mL) was added TFA (5 mL). The reaction was aged at room temperature for 3 h, and then concentrated in vacuo to give the title compound as a TFA salt which was used without further purification. ESI-MS (m/z): 186 [M+1]+.

Example 36

2-((5-chloropyridin-2-yl)amino)-2-oxoethyl acetate

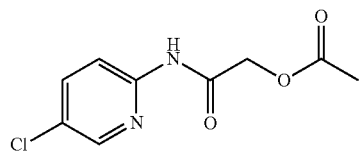

To a solution of 5-chloropyridin-2-amine (1.28 g) in dichloromethane (10 mL) was added 2-chloro-2-oxoethyl acetate (1.08 mL) and triethylamine (2.8 mL). The reaction was stirred at room temperature for 1 h, and then concentrated in vacuo. The crude residue was taken up in EtOAc and washed with sat aq. NaHCO$_3$, 1M HCl, brine, dried (MgSO$_4$), and concentrated to yield the title product which was used without further purification. $^1$H NMR (CHCl$_3$, 400 MHz) δ 8.4 (br s, H), 8.2 (m, 2H), 7.6 (m, 1H), 4.7 (s, 2H), 2.2 (s, 3H).

Example 37

N-(5-chloropyridin-2-yl)-2-hydroxyacetamide

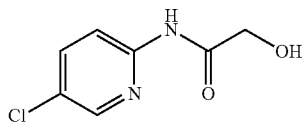 [SMILES: O=C(CO)Nc1ccc(Cl)cn1]

To a solution of the crude product from the previous step in MeOH was added catalytic K2CO3 (5 mg). The reaction was stirred at room temperature for 3 h, and concentrated in vacuo. The crude residue was taken up in EtOAc and washed with sat aq. NaHCO$_3$, 1M HCl, brine, dried (MgSO$_4$), and concentrated to yield the title product. $^1$H NMR (D$_6$-acetone, 400 MHz) δ 9.2 (br s, H), 8.29 (d, 1H), 8.27 (d, 1H), 7.8 (dd, 1H), 5.0 (t, H), 4.1 (d, 2H).

Example 38

2-(N-(3-bromophenethyl)methylsulfonamido)-N-(5-chloropyridin-2-yl)acetamide

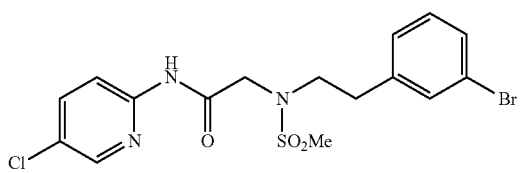 [SMILES: CS(=O)(=O)N(CCc1cccc(Br)c1)CC(=O)Nc1ccc(Cl)cn1]

To a solution of the product from Example 32 (18 mg) and triethylamine (2eq) in dichloromethane at 0° C. was added methanesulfonylchloride (8 μL). The reaction was allowed to come to room temperature over 30 minutes and then aged for 1 h. The reaction was diluted with EtOAc, and washed with 1M HCl, brine, dried (MgSO$_4$), and concentrated in vacuo. Purification by chromatography on silica gel (EtOAc/hexanes) provided the title compound. $^1$H NMR (CHCl$_3$, 400 MHz) δ 8.4 (br s, H), 8.2 (br s, H), 8.1 (br s, H), 7.6 (d, H), 7.4 (d, 2H), 7.2 (d, 2H), 4.0 (s, 2H), 3.6 (t, 2H), 2.9 (m, 5H).

Example 39

N-(5-chloropyridin-2-yl)-2-(phenethylamino)acetamide

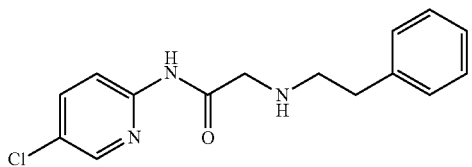 [SMILES: O=C(CNCCc1ccccc1)Nc1ccc(Cl)cn1]

The title compound was synthesized following the same general protocol as described in Example 22, starting with 2-chloro-N-(5-chloropyridin-2-yl)acetamide and 2-phenylethanamine. ESI-MS (m/z): 290 [M+1]+.

Example 40

N-(5-chloropyridin-2-yl)-3-(3-(trifluoromethyl)phenoxy)benzamide

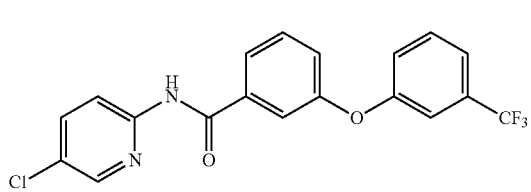 [SMILES: O=C(Nc1ccc(Cl)cn1)c1cccc(Oc2cccc(C(F)(F)F)c2)c1]

Step 1. methyl 3-(3-(trifluoromethyl)phenoxy)benzoate

A mixture of 3-trifluoromethylphenol (486 mg), methyl 3-bromobenzoate (430 mg), Cs$_2$CO$_3$ (1.3 g), dimethylglycine (61 mg), and CuI (76 mg) in dioxane (10 mL) was heated in a microwave reactor at 100° C. for 12 h. The reaction mixture was cooled, and diluted with EtOAc and water. The layers were separated and the organic phase was washed with 1M HCl, brine, dried (MgSO$_4$) and concentrated. Purification of the crude residue on silica gel (EtOAc/hexanes) provided the title compound in 57% yield.

Step 2. 3-(3-(trifluoromethyl)phenoxy)benzoic acid

To a solution of the product from Step 1 (150 mg) in THF/H$_2$O (8 mL, 1:1 v/v) was added 1M LiOH (5 mL). The reaction was stirred at room temperature for 3 h, and then diluted with EtOAc and 1M HCl until the pH of the aqueous phase was ~5. The layers were separated, and the organic phase was dried (MgSO$_4$) and concentrated to give the title compound which was used without further purification.

Step 3. N-(5-chloropyridin-2-yl)-3-(3-(trifluoromethyl)phenoxy)benzamide

The title compound was prepared following the same general procedure as described in Example 1, Step 3, using 5-chloropyridin-2-amine and the product from Step 2. ESI-MS (m/z): 393 [M+H]⁺.

Example 41

2-(3-bromophenethoxy)-N-(5-chloropyridin-2-yl)acetamide

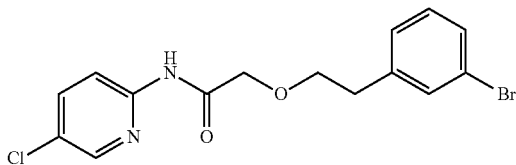 [SMILES: O=C(COCCc1cccc(Br)c1)Nc1ccc(Cl)cn1]

The title compound was synthesized following the same general protocol as described in Example 16, starting with 2-bromo-N-(5-chloropyridin-2-yl)acetamide and 2-(3-bromophenyl)ethanol. ESI-MS (m/z): 369, 371 [M+1]⁺.

Example 42

2-(4-bromophenethoxy)-N-(5-chloropyridin-2-yl)acetamide

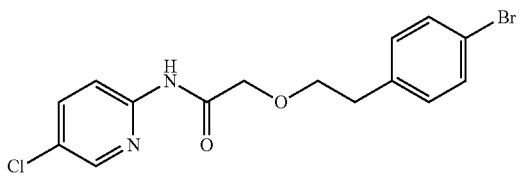 [SMILES: O=C(COCCc1ccc(Br)cc1)Nc1ccc(Cl)cn1]

The title compound was synthesized following the same general protocol as described in Example 16, starting with 2-bromo-N-(5-chloropyridin-2-yl)acetamide and 2-(4-bromophenyl)ethanol. $^1$H NMR (CHCl$_3$, 400 MHz) δ 8.5 (br s, H), 8.4 (br s, H), 7.7 (m, H), 7.4 (d, 2H), 7.2 (d, 2H), 4.1 (s, 2H), 3.8 (t, 2H), 2.9 (t, 2H).

Example 43

2-(2-bromophenethoxy)-N-(5-chloropyridin-2-yl)acetamide

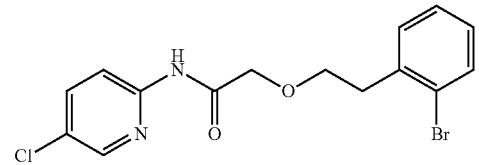 [SMILES: O=C(COCCc1ccccc1Br)Nc1ccc(Cl)cn1]

The title compound was synthesized following the same general protocol as described in Example 16, starting with 2-bromo-N-(5-chloropyridin-2-yl)acetamide and 2-(2-bromophenyl)ethanol. ESI-MS (m/z): 369, 371 [M+1]⁺

Example 44

N-(5-chloropyridin-2-yl)-2-(3-(trifluoromethyl)phenethoxy)acetamide

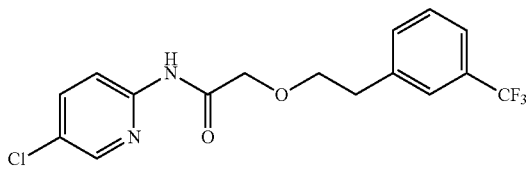 [SMILES: O=C(COCCc1cccc(C(F)(F)F)c1)Nc1ccc(Cl)cn1]

The title compound was synthesized following the same general protocol as described in Example 16, starting with 2-bromo-N-(5-chloropyridin-2-yl)acetamide and 2-(3-trifluoromethylphenyl)ethanol. ESI-MS (m/z): 359 [M+1]⁺

Example 45

N-(5-chloropyridin-2-yl)-2-(3-fluorophenethoxy)acetamide

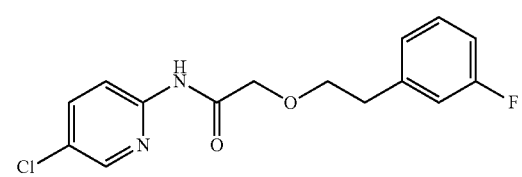 [SMILES: O=C(COCCc1cccc(F)c1)Nc1ccc(Cl)cn1]

The title compound was synthesized following the same general protocol as described in Example 16, starting with 2-bromo-N-(5-chloropyridin-2-yl)acetamide and 2-(3-fluorophenyl)ethanol. ESI-MS (m/z): 309 [M+1]⁺

Example 46

N-(5-chloropyridin-2-yl)-2-(3-methylphenethoxy)acetamide

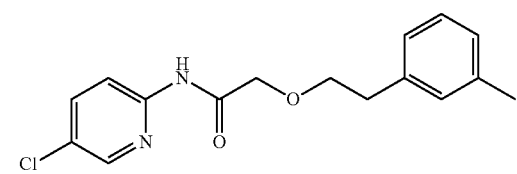 [SMILES: Cc1cccc(CCOCC(=O)Nc2ccc(Cl)cn2)c1]

The title compound was synthesized following the same general protocol as described in Example 16, starting with 2-bromo-N-(5-chloropyridin-2-yl)acetamide and 2-(3-methylphenyl)ethanol. ESI-MS (m/z): 305 [M+1]⁺

Example 47

N-(4-chlorophenyl)-2-(3-(trifluoromethyl)phenoxy)acetamide

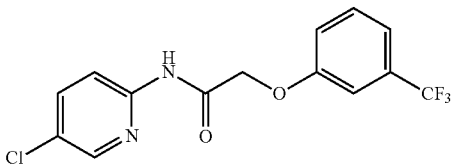 [SMILES: O=C(COc1cccc(C(F)(F)F)c1)Nc1ccc(Cl)cn1]

The title compound was synthesized following the same general protocol as described in Example 16, starting with 2-bromo-N-(5-chloropyridin-2-yl)acetamide and 3-trifluoromethylphenol. ESI-MS (m/z): 331 [M+1]+

Example 48

N-(5-chloropyridin-2-yl)-2-((3-(trifluoromethyl)benzyl)oxy)acetamide

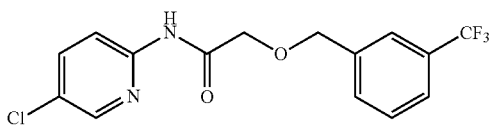 [SMILES: O=C(COCc1cccc(C(F)(F)F)c1)Nc1ccc(Cl)cn1]

The title compound was synthesized following the same general protocol as described in Example 16, starting with 2-bromo-N-(5-chloropyridin-2-yl)acetamide and 3-trifluoromethylbenzyl alcohol. ESI-MS (m/z): 345 [M+1]+

Example 49

N-(5-chloropyridin-2-yl)-4-(3-(trifluoromethyl)phenoxy)butanamide

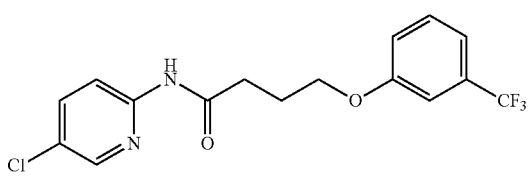 [SMILES: O=C(CCCOc1cccc(C(F)(F)F)c1)Nc1ccc(Cl)cn1]

Step 1. methyl 4-(3-(trifluoromethyl)phenoxy)butanoate

To a solution of 3-trifluoromethylphenol (162 mg) and ethyl 4-bromobutanoate (391 mg) in DMF (5 mL) was added K$_2$CO$_3$ (2eq). The reaction was warmed to 90° C. in a microwave reactor for 2 h, and then cooled. The crude residue was taken up in EtOAc and washed with sat aq. NaHCO$_3$, 1M HCl, brine, dried (MgSO$_4$), and concentrated to yield a crude residue which was purified by chromatography on silica gel (EtOAc/hexanes) to afford the title compound. ESI-MS (m/z): 277 [M+1]+.

Step 2. 4-(3-(trifluoromethyl)phenoxy)butanoic acid

To a solution of the product from Step 1 (75 mg) in EtOH/H$_2$O (5 mL, 1:1 v/v) was added KOH (3 eq). The reaction was stirred at room temperature for 6 h, and then diluted with EtOAc and 1M HCl until the pH of the aqueous phase was ~5. The layers were separated, and the organic phase was dried (MgSO$_4$) and concentrated to give the title compound which was used without further purification.

Step 3. N-(5-chloropyridin-2-yl)-4-(3-(trifluoromethyl)phenoxy)butanamide

The title compound was prepared following the same general procedure as described in Example 1, Step 3, using 5-chloropyridin-2-amine and the product from Step 2. ESI-MS (m/z): 359 [M+H]+.

Example 50

N-(3-bromophenethyl)-2-((5-chloropyridin-2-yl)amino)acetamide

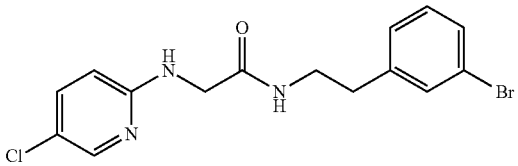 [SMILES: O=C(CNc1ccc(Cl)cn1)NCCc1cccc(Br)c1]

Step 1. tert-butyl 2-((5-chloropyridin-2-yl)amino)acetate

To a solution of 5-chloro-2-fluoropyridine (780 mg) and tert-butylglycine hydrochloride (1 g) in DMSO (10 mL) was added triethylamine (2 mL). The reaction was warmed to 100° C. for 12 h, and then cooled. The crude residue was taken up in EtOAc and washed with sat aq. NaHCO$_3$, 1M HCl, brine, dried (MgSO$_4$), and concentrated to yield a crude residue which was purified by chromatography on silica gel (EtOAc/hexanes) to afford the title compound. $^1$H NMR (d$_6$-DMSO, 400 MHz) δ 8.0 (d, H), 7.5 (dd, H), 7.2 (t, H), 6.6 (d, H), 3.9 (d, 2H), 1.4 (s, 9H).

Step 2. 2-((5-chloropyridin-2-yl)amino)acetic acid

To a solution of the product from Step 1 (196 mg) in CH$_2$Cl$_2$ (5 mL) was added TFA (5 mL). The reaction was aged at room temperature for 2 h, and then concentrated in vacuo. The crude acid was used without further purification.

Step 3. N-(3-bromophenethyl)-2-((5-chloropyridin-2-yl)amino)acetamide

The title compound was prepared following the same general procedure as described in Example 19, Step 1, using 2-(3-bromophenyl)ethanamine and the product from Step 2. ESI-MS (m/z): 368, 370 [M+H]⁺.

Example 51 N-(5-chloropyridin-2-yl)-2-(2-(2-fluorophenyl)acetamido)acetamide

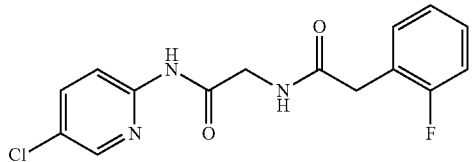 [SMILES: O=C(Cc1ccccc1F)NCC(=O)Nc1ccc(Cl)cn1]

To a solution of 2-amino-N-(5-chloropyridin-2-yl)acetamide in DMF (1 mL) was added Hunig's base (2eq) followed 1-(1H-benzo[d][1,2,3]triazol-1-yl)-2-(2-fluorophenyl)ethanone (1.1 eq). The reaction was heated in a microwave reactor at 100° C. for 1 h, and then cooled. Purification by chromatography on silica gel (EtOAc/hexanes) provided the title compound. ESI-MS (m/z): 322 [M+1]⁺.

Example 52

N-(5-chloropyridin-2-yl)-2-(2-(4-fluorophenyl)acetamido)acetamide

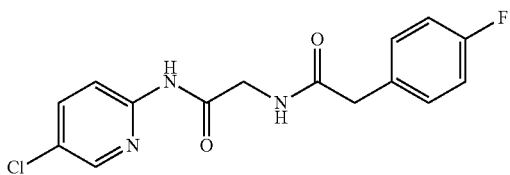 [SMILES: O=C(Cc1ccc(F)cc1)NCC(=O)Nc1ccc(Cl)cn1]

To a solution of 2-amino-N-(5-chloropyridin-2-yl)acetamide in DMF (1 mL) was added Hunig's base (2eq) followed 1-(1H-benzo[d][1,2,3]triazol-1-yl)-2-(4-fluorophenyl)ethanone (1.1 eq). The reaction was heated in a microwave reactor at 100° C. for 1 h, and then cooled. Purification by chromatography on silica gel (EtOAc/hexanes) provided the title compound. ESI-MS (m/z): 322 [M+1]⁺.

Example 53

N-(3-bromophenethyl)-N-(2-((5-chloropyridin-2-yl)amino)-2-oxoethyl)acetamide

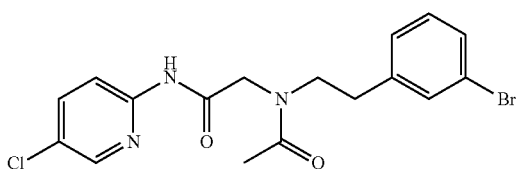 [SMILES: CC(=O)N(CCc1cccc(Br)c1)CC(=O)Nc1ccc(Cl)cn1]

To a solution of the product from Example 32 (1 eq) and triethylamine (2eq) in dichloromethane at 0° C. was added acetyl chloride (1.5eq). The reaction was allowed to come to room temperature over 30 minutes and then aged for 1 h. The reaction was diluted with EtOAc, and washed with 1M HCl, brine, dried (MgSO₄), and concentrated in vacuo. Purification by chromatography on silica gel (EtOAc/hexanes) provided the title compound. ESI-MS (m/z): 410 [M+1]⁺.

Example 54

N-(5-chloropyridin-2-yl)-6-((3-(trifluoromethyl)phenyl)amino)picolinamide

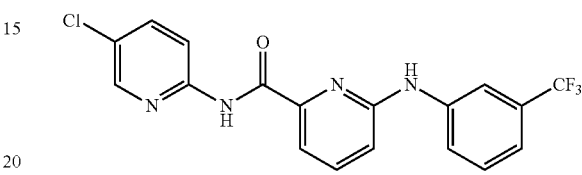

Step 1: methyl 6-((3-(trifluoromethyl)phenyl)amino)picolinate

To a solution of methyl 6-bromopicolinate (1eq) and 3-(trifluoromethyl)aniline (1.1 eq) in dioxane was added Pd₂(dba)₃ (0.2 eq), Cs₂CO₃ (3 eq), and (9,9-dimethyl-9H-xanthene-4,5-diyl)bis(diphenylphosphine) (0.3 eq). The mixture was heated to 90° C. for 16 h, and then filtered through a pad of celite. The filtrate was diluted with EtOAc and water, and the layers were separated. The organic layer was washed with water, brine, dried (MgSO₄) and concentrated.

The crude residue was purified by chromatography on silica gel to afford the title compound in 36% yield as a brown solid. ESI-MS (m/z): 297.1 [M+1]⁺.

Step 2: 6-((3-(trifluoromethyl)phenyl)amino)picolinic acid

To a solution of methyl 6-((3-(trifluoromethyl)phenyl)amino)picolinate in THF/H₂O was added 1M LiOH. The reaction was stirred at rt for 18 h, and then diluted with EtOAc and acidified with 1M HCl until pH~6. The layers were separated, and the aqueous layer was extracted with EtOAc (2×). The combined organics were washed with brine, dried (MgSO₄) and concentrated to give the title compound as a brown solid which was used without further purification. ESI-MS (m/z): 283.1 [M+1]⁺.

Step 3: N-(5-chloropyridin-2-yl)-6-((3-(trifluoromethyl)phenyl)amino)picolinamide To a solution of N-(5-chloropyridin-2-yl)-6-((3-(trifluoromethyl)phenyl)amino)picolinamide and 5-chloropyridin-2-amine in DMF was added HATU and DIEA. The reaction was stirred at rt for 72 h. The reaction was concentrated in vacuo, and diluted with EtOAc and water. The layers were separated, and the aqueous layer was extracted with EtOAc (2×). The combined organics were washed with brine, dried (MgSO₄) and concentrated to give the title compound which was purified on silica gel (EtOAc/hex) to afford the title compound as a brown solid. ESI-MS (m/z): 393.2 [M+1]⁺.

Example 55

2-(3-bromophenethoxy)-N-(5-chloropyridin-2-yl) propanamide

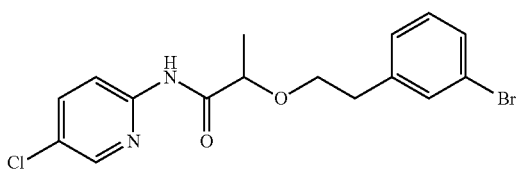 [SMILES: CC(OCCc1cccc(Br)c1)C(=O)Nc1ccc(Cl)cn1]

Example 55 was prepared following the same standard protocol as described for Example 7, using tert-butyl 2-bromopropanoate, 2-(3-bromophenyl)ethanol, and 6-chloropyridin-3-amine. ESI-MS (m/z): 383.0 [M+1]$^+$.

Methods

Cells and Mice.

HEK293 cells were grown in Dulbecco's Modification of Eagles Medium (with 4.5 g/L glucose and L-glutamine), supplemented with 10% fetal bovine serum, penicillin and streptomycin. Raw264.7 cells were cultured in RPMI-1640 media containing 10% heat-inactivated fetal bovine serum, penicillin and streptomycin. C57BL/10ScSn-Dmd$^{mdx}$/J and female C57BL/6 mice were purchased from the Jackson Laboratory. Mice were housed in the animal facilities of Scripps Fla. under constant temperature and humidity. Animal protocols used in this study were approved by Scripps Fla. Institutional Animal Care and Use Committees. Three week-old sex-matched mdx mice were dosed with SR12343 (30 mg/kg), SR1246 (30 mg/kg), 8K-NBD peptide (10 mg/kg) or vehicle by intraperitoneal (i.p.) injection 3 times per week for 4 weeks. Mice were sacrificed at 7 weeks of age by carbon dioxide inhalation and tibialis anterior was collected for histological analysis.

8K-NBD Peptide and Small Molecules.

8K-NBD (KKKKKKKKGGTALDWSWLQTE) peptide was synthesized at the peptide core facility of University of Pittsburgh. For i.p. injections, peptide was dissolved in 10% DMSO in PBS. They were formulated in 10:10:80 of DMSO:Tween 80:Water for in vivo administration. ZINC small molecules were purchased from Enamine. All stock solutions for in vitro experiments were prepared in DMSO at 40 μM.

LPS-Induced Acute Lung Inflammation.

LPS (strain O111:B4) was prepared in PBS at a sub-lethal dose of 10 mg/kg. 8-10 weeks old female WT mice (20-30 g) were dosed i.p. with vehicle, NBD peptide (10 mg/kg) or small molecules (10 mg/kg) for 30 min and followed by i.p. injection of saline (1 ml/kg) or LPS (10 mg/kg). Mice were euthanized 2-4 hr post-treatment and lung was collected for further analysis.

Functional Grip Strength Analysis.

Seven week-old treated or untreated mdx mice were measured for forelimb grip strength using a digital grip strength meter paired with a metal grid (Bioseb). Mice were allowed to grip the metal grid tightly and readings were obtained by gently pulling the tail backward until release. Five sequential measurements were performed and the average force was calculated.

Firefly Luciferase Assay.

HEK293 cells stably transfected with luciferase reporter plasmid driven by NF-κB were seeded in 96-well plate in triplicate and pretreated with DMSO or varying small molecules at indicated concentration for 30 min, followed by the stimulation of 10 ng/ml of TNFα for 3 hr. Cell were washed with PBS once and harvested in passive lysis buffer. Luciferase assay (Promega) was performed using a luminometer according to the manufacturer's instructions.

Dual-Luciferase Reporter Assay.

HEK293 cells grown in 10 cm plates were co-transfected with co-reporter of Renilla plasmid driven by SV40 and luciferase plasmid driven by NF-κB at the ratio of 1:3 with Lipofectamine 2000 (Invitrogen). Transiently transfected HEK293 were grown and treated as described above and subjected to a dual-luciferase reporter assay according to the manufacturer's instruction. Firefly luciferase activity was normalized to Renilla luciferase to get the relative luciferase activity.

MTT Assay.

HEK293 cells were grown in a 96-well plate at 3×10$^4$ cells/well in triplicate and treated with DMSO or varying small molecules at indicated concentration for 24 hr. Cell survival was determined by adding 20 ul of 5 mg/ml MTT (thiazolyl blue tetrazolium bromide) to each well followed by incubation for 3 hr in an 37° C. incubator. Media was removed and purple formazan was dissolved in 100 ul of DMSO. Absorbance was measured at 590 nm on a microplate reader (Perkin Elmer). Cell viability was calculated by normalizing values to untreated control.

Western Blotting.

HEK293 cells grown in a 6-well plate at 1×10$^6$ cells/well were left untreated or treated with 100 μM of ZINC12909780 or ZINC3369392 for 30 min, followed by 10 ng/ml of TNFα for 0, 5 and 10 min. Cells were then harvested for western blot. Cell lysate was prepared in RIPA buffer (20 mM Tris-HCl (pH 7.5), 150 mM NaCl, 1 mM Na$^2$EDTA, 1 mM EGTA, 1% NP-40, 1% sodium deoxycholate, 2.5 mM sodium pyrophosphate, 1 mM beta-glycerophosphate, 1 mM Na$_3$VO$_4$, 1 μg/ml leupeptin, 1× protease inhibitor cocktails (sigma) and 1× Halt phosphatase inhibitor cocktail (Thermo)). 30 ug of protein was resolved by MINI-PROTEAN TGX 4-15% SDS-PAGE. Blots were blocked in 5% non-fat milk. Primary antibodies were incubated at 4° C. overnight and secondary antibodies were incubated at room temperature for 1 hour. Anti-p-IκBα (1:1000 CST) and anti-IκBα (1:2000 CST) were used to assess NF-κB activation. Anti-GAPDH (1:5000 CST) was used as a loading control.

Immunoprecipitation of Endogenous IKKβ and NEMO.

HEK293 or Raw264.7 cells were seeded at 1×10$^6$ cells/well in 6-well plates and treated with vehicle, small molecule or NBD peptide for indicated time. Cells were lysed in NP-40 lysis buffer supplemented with 1× protease inhibitor cocktails (sigma). Protein was immunoprecipitated by incubating 150 μg of lysate with 1 μg of anti-NEMO antibody (Santa Cruz) on a rotating shaker at 4° C. for 4 hrs, followed by incubation with 20 ul of Protein A agarose beads (ThermoFisher) for 1 hr. Beads were washed in NP40 buffer 3 times and PBS once. Protein was then denatured in SDS-sample buffer and resolved by MINI-PROTEAN TGX 4-15% SDS-PAGE. Anti-IKKβ (1:1000 CST) was used to assess binding of IKKβ to NEMO and anti-NEMO (1:1000 CST) or IgG were used to as a loading control.

Electrophoretic Mobility Shift Assay (EMSA).

Cytoplasmic and nuclear fractions were extracted using the NE-PER nuclear and cytoplasmic extraction reagents (ThermoFisher) according to the manufacturer's instructions. The gel shift assay was performed by following the previously described method (41). In brief, 5 μg of nuclear extract was incubated with gel shift binding buffer and an α-$^{32}$P-deoxycytodine triphosphate-radiolabeled NF-κB probe for 20 min at room temperature (MP Biomedicals). The oligonucleotide sequences are as follows: NF-κB template, 5'-CAGGGCTGGGGATTCCCCATCTCCACA-GTTTCACTTC-3'; NF-κB annealing, 5'-GAAGT-GAAACTGTGG-3'. The reaction product was separated on a 6% non-denaturing polyacrylamide gel.

Quantitative Reverse Transcription-Polymerase Chain Reaction (qRT-PCR).

Snap frozen tissues were preserved in RNAlater RNA stabilization solution (ThermoFisher) before processed. Total RNA was extracted from cells or tissues using TRIZOL reagent (Life Technologies) and 1500 ng of messenger RNA (mRNA) was subjected to synthesize complementary DNA (cDNA) using SuperScript VILO cDNA synthesis kit. qRT-PCR was performed in a StepOnePlus Real-Time PCR system using Platinum SYBR Green qPCR SuperMix-UDG (ThermoFisher). Target gene expression was calculated using the comparative $C_T$ method ($\Delta\Delta C_T$) and normalized to an internal control gene Actb (β-actin). Primers used are as follows: Ptgs2 (COX-2) forward: ACTCATAGGAGAGACTATCAAG; Ptgs2 (COX-2) reverse: GAGTGTGTTGAATTCAGAGG; Nfkbia (IκBα) forward: CAGAATTCACAGAGGATGAG; Nfkbia (IκBα) reverse: CATTCTTTTTGCCACTTTCC; Il1b (IL-1β) forward: GGATGATGATGATAACCTGC; Il1b (IL-1β) reverse: CATGGAGAATATCACTTGTTGG; Nos2 (iNOS) forward: TGAAATCCCTCCTGATCTTG; Nos2 (iNOS) reverse: CCATGTACCAACCATTGAAG; Tnf (TNF) forward: CTATGTCTCAGCCTCTTCTC; Tnf (TNF) reverse: CATTTGGGAACTTCTCATCC; Il6 (IL-6) forward: AAGAAATGATGGATGCTACC; Il6 (IL-6) reverse: GAGTTTCTGTATCTCTCTGAAG. Actb (β-actin) forward: GATGTATGAAGGCTTTGGTC; Actb (β-actin) reverse: TGTGCACTTTTATTGGTCTC;

Enzyme-Linked Immunosorbent Assay (ELISA). Raw264.7 cells were grown in a 96-well plate and pretreated with vehicle, IKKi VII (2 uM) and small molecules (at indicated concentration) for 1 hr, followed by the stimulation with 1 ug/ml of LPS. Supernatant was collected 24 hr later for ELISA analysis. IL-6 concentration was measured using a mouse IL-6 ELISA kit (BD) according to the manufacturer's instructions.

Hematoxylin and Eosin (H&E) Staining.

Tissues fixed in 10% neutral buffered formalin (NBF) overnight were imbedded in paraffin. Tissue was sectioned at 5 m using a microtome. H&E staining was conducted following a standard protocol (REF).

Pharmacokinetics Study.

The pharmacokinetic profiles of the NBD mimetics were determined in male C57BL/6J mice (n=3). The drugs were formulated in 10:10:80 of DMSO:Tween 80:water and were dosed by intraperitoneal injection at a final dose of 10 mg/kg. Blood, brain, muscle, spleen, and liver were collected 2 hr post-treatment and were analyzed by mass spectrometry by following the protocol described in ref. 215 (42).

Pharmacophore Model Generation.

X-ray structure of the complex NEMO/IKKβ retrieved from the Protein Data Bank [PDB ID: 3BRV], was used to generate a structure-based pharmacophore model (18). The three-dimensional (3D) pharmacophore model was created with LigandScout (21, 22) and was based on interactions that define the protein-protein interaction, such as hydrophobic interactions, hydrogen bonding, and electrostatic interactions. Features identified by the LigandScout software are those that take into consideration chemical functionality but not strict structural topology or definite functional groups. As a result, completely new potential pharmacons can be identified through database screening. Moreover, to increase the selectivity, the LigandScout model includes spatial information regarding areas inaccessible to any potential ligand, thus reflecting possible steric restrictions. In particular, excluded volume spheres placed in positions that are sterically not allowed are automatically added to the generated pharmacophore model. In this way, the structure-derived pharmacophore model contains the pharmacophore elements of the candidate ligands in response to the protein's active site environment.

Similarity Search.

The morphological similarity is a similarity technique dependent only on surface shape and charge characteristics of ligands. Morphological similarity is defined as a Gaussian function of the differences in the molecular surface distances of two molecules at weighted observation points on a uniform grid. The computed surface distances include both distances to the nearest atomic surface and distances to donor and acceptor surfaces. This function is dependent on the relative alignment of the molecules, and consequently their alignment and conformation must be optimized. The conformational optimization problem is solved by fragmentation, conformational search, alignment, and scoring, followed by incremental reconstruction from high-scoring aligned fragments. The alignment problem is addressed by exploiting the fact that two unaligned molecules or molecular fragments that have some degree of similarity will have some corresponding set of observers that are seeing the same things. Optimization of the similarity of two unaligned molecules or molecular fragments is enabled by finding similar sets of observers of each molecule that form triangles of the same size.

In Silico ADME and Toxicity Screening.

Computational modeling tools were used to estimate the bioavailability, aqueous solubility, blood brain barrier potential, human intestinal absorption, the cytochrome P450 (i.e. CYP2D6) enzyme inhibition potential, mutagenicity, and hERG inhibition of the hits obtained from the database screening. The bioavailability, aqueous solubility, and human intestinal absorption were estimated using the Advanced Chemistry Development, Inc. (ACD/Labs)/ADME Boxes software while mutagenicity, hERG and CYP2D6 inhibition were estimated with ACD/Tox screening (ACD Labs, Toronto, Canada).

Statistical Analysis.

All values were presented as mean+/−S.E.M. Microsoft Excel and Graphpad Prism 6 were used for statistical analysis. Two-tailed Student's t-test was performed to determine differences between two groups. When comparing difference in more than two groups, one-way ANOVA (Dunnett test) was conducted. A value of $p<0.05$ was considered as statistically significant, shown as *$p<0.05$, $p<0.01$, and *$p<0.001$.

SR12343 Naked Mouse Skin Study

Figure 51:
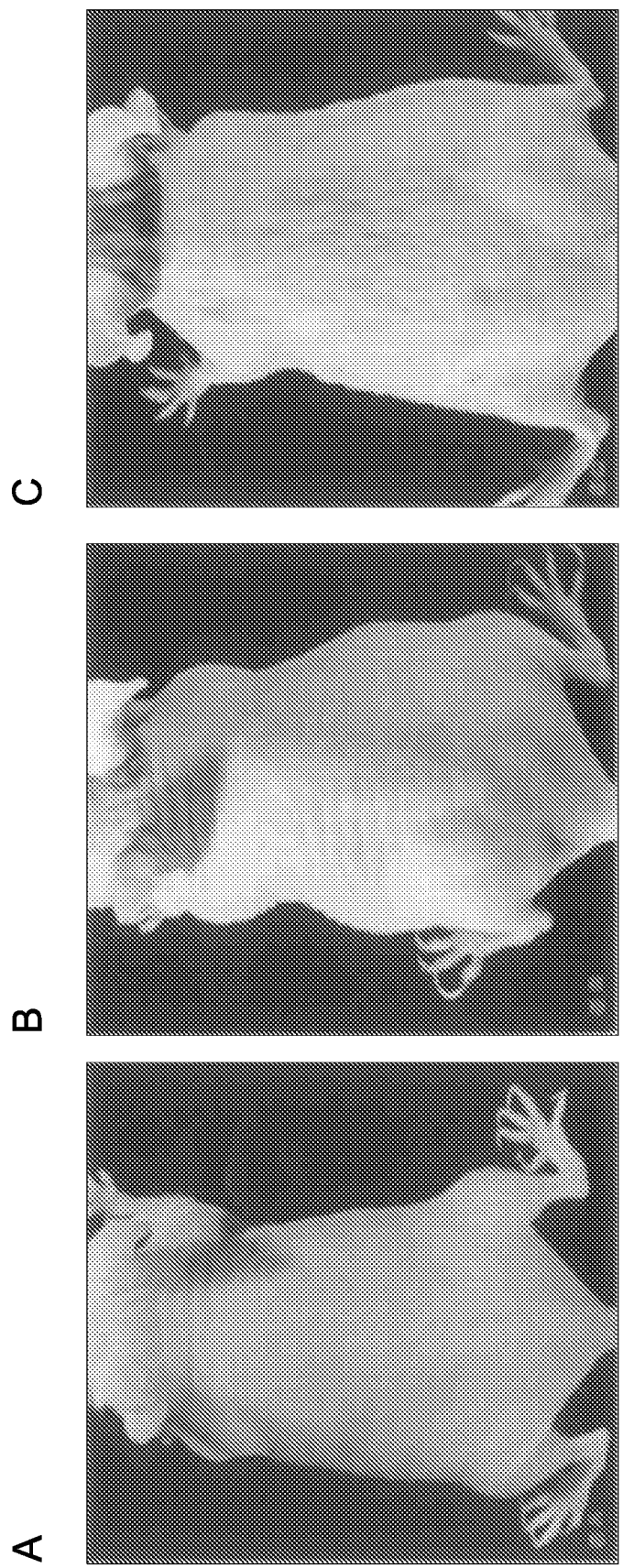
FIG. 51 shows the K14-Cre$^{+/-}$; Ercc1$^{-/fl}$; Skh1$^{-/-}$ naked mouse model used in the skin study with SR12343, following 5-7 months UV irradiation: (A) normal naked mouse showing skin "crinkles"; (B) UVB-induced skin wrinkles, and (C) UVA-induced skin sagging.

Naked mice of strain K14-Cre$^{+/-}$; Ercc1$^{-/fl}$; Skh1$^{-/-}$ were treated with SR12343 versus vehicle control, then exposed to UV light for 5-6 months. The NBD mimetic SR12343 and SR2460 were tested for their ability to reduce the effects of photoaging in a mouse model. To make analysis of skin aging easier, usually hairless mice are utilized. Previously studies have shown that exposure of the hairless Skh1$^{-/-}$ mouse to UV results in skin aging over 5 months as measured by skin thickness, elastosis, collagen damage, synthesis and degradation, increased ratio of collagen III to I, increased GAGs, and wrinkles and sagging. To accelerate this photoaging process, we generated a mouse model where Ercc1-dependent DNA repair activity is eliminated in K14 expressing skin cells in the Skh1$^{-/-}$ mice (K14-Cre$^{+/-}$; Ercc1$^{-/fl}$; Skh1$^{-/-}$ mice). In these mice, chronic UV exposure gives rise to evidence of photoaging 6 times faster than in the Skh1$^{-/-}$ mice, allowing for analysis of skin aging in 2-4 weeks (FIGS. 51 (A, B, and C).

For testing of drugs for effects on photoargng in the K14-Cre$^{+/-}$; Ercc1$^{-/fl}$; Skh1$^{-/-}$ mice, the mice are first tattooed to outlined quadrants for drug treatment. The mice were then exposed to UV 3× (total of 1 kJ/m$^2$/wk) for 4 weeks in a tanning booth. This dose regiment is the equivalent of one year of sun exposure.

A 50 mg/ml solution of SR12343 was then prepared in a DMSO gel for topical application. The SR12343 gel was administered topically 5 times per week and mice exposed to UV 3× per week as indicated. It is important to note that the compound was administered following UV dosing to eliminate any anti-UV effects of the drug. At the midway point and at the end of the experiment, the mice were analyzed using a TEWL Meter for skin thickness, elasticity and hydration. At the time of sacrifice, skin sections are taken for analysis of the extent of cellular senescence by RT-PCR.

Figure 52:
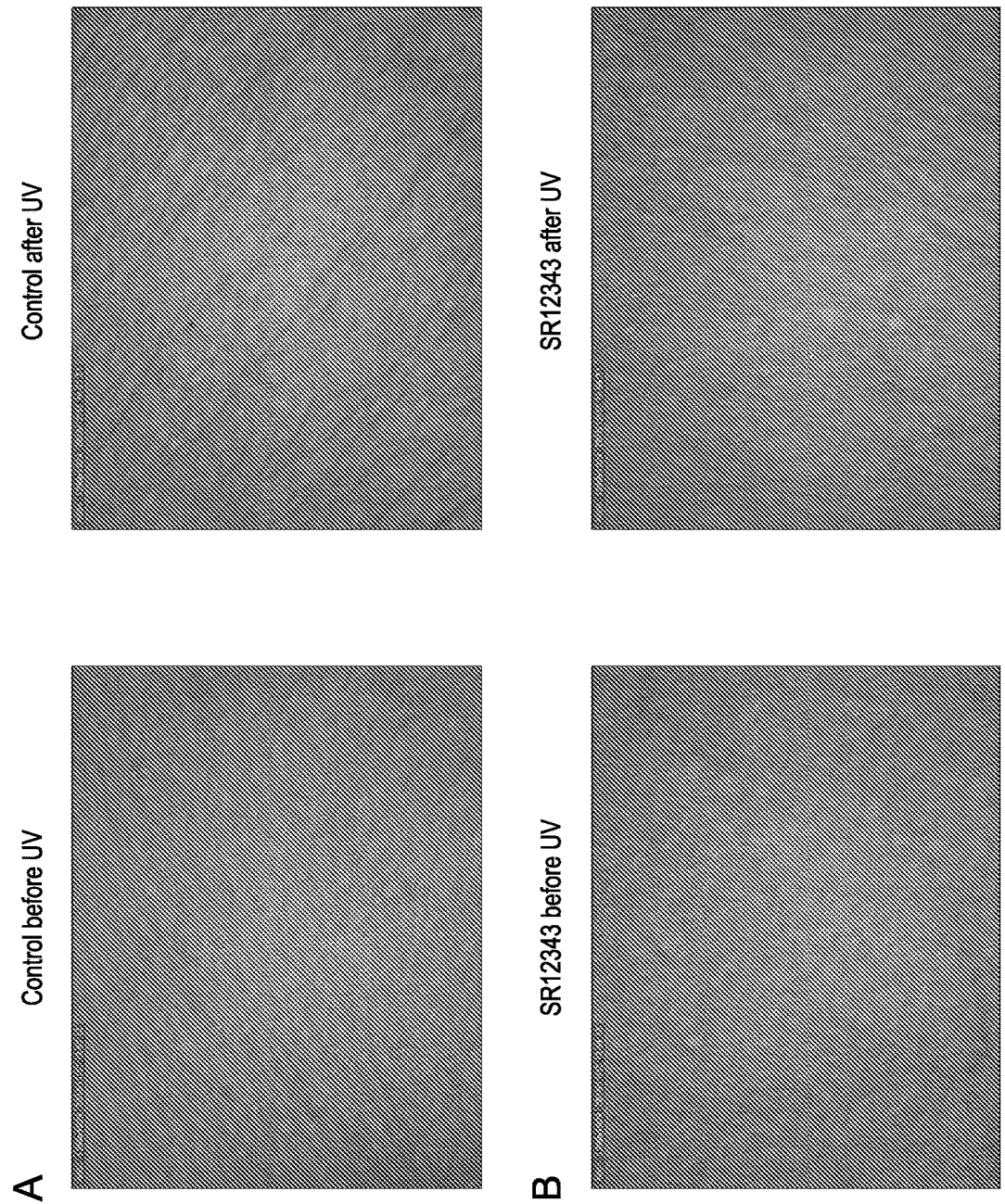
FIG. 52 shows shows close-ups of skin of naked mice treated with (A) before and after treatment with vehicle control, and (B) before and after treatment with SR12343.
Figure 53:
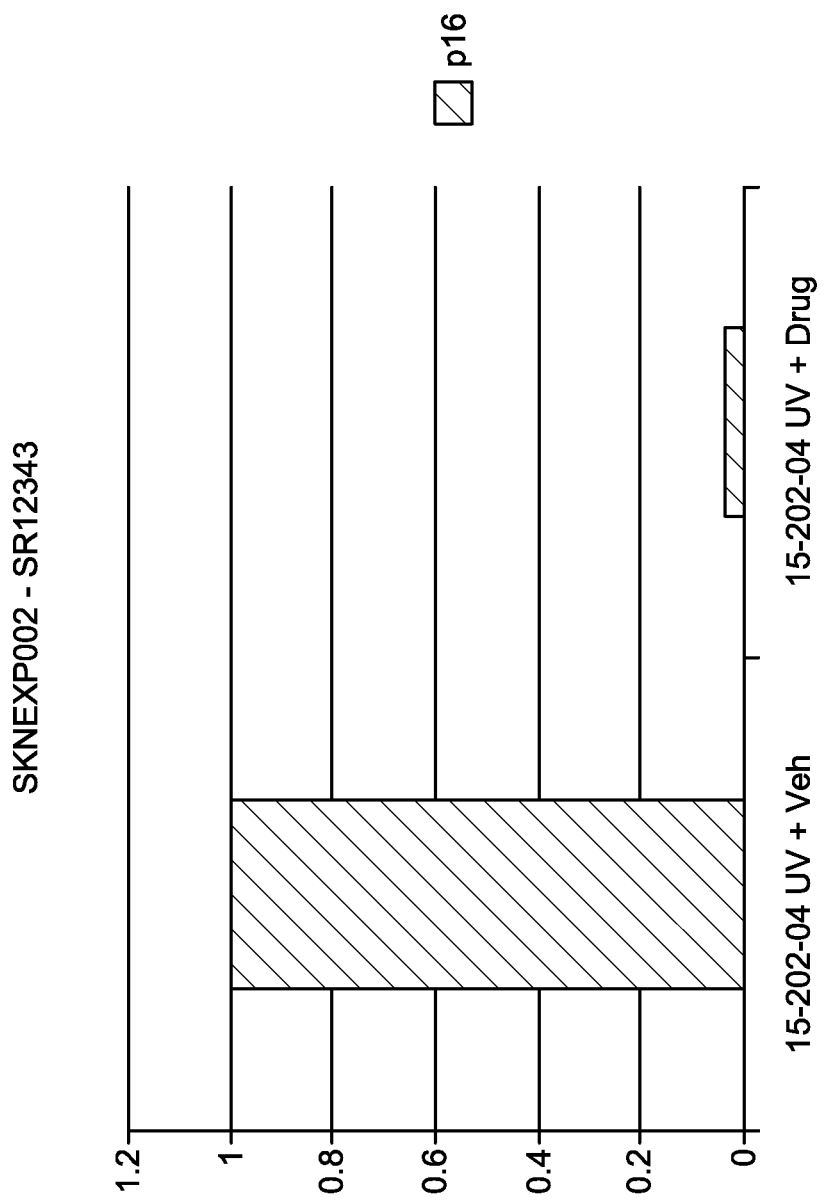
FIG. 53 depicts a bar graph showing the level of senescence marker p16 in naked mouse skin following treatment with SR12343 versus vehicle control.

As shown in FIGS. 52 (A and B), treatment with SR12343 approved the overall appearance of the skin, reducing the number and depth of the wrinkles. It also restores skin elasticity, improved skin hydration and lowered the expression of senescent markers such as p16. FIG. 53 shows graphically the marked diminishment of the expression of senescent marker p16 after treatment with SR12343.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of inhibiting, within a living cell, the interaction of NF-κB essential modulator (NEMO) with IκB kinase-β (IKK-β) at the NEMO binding domain (NBD), comprising exposing the cell to an effective amount or concentration of a compound of formula (IA)

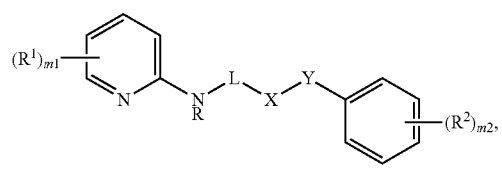

(IA)

wherein
the ring bonded to Y comprises 0 or 1 nitrogen atom;
R is H, (C$_1$-C$_6$)alkyl, (C$_3$-C$_6$)cycloalkyl(C$_1$-C$_6$)alkyl, or (C$_2$-C$_6$)acyl;
each R$^1$ is independently selected from halo, alkyl, and haloalkyl; m1=0, 1, 2, or 3;
each R$^2$ is independently selected from halo, alkyl, and haloalkyl; m2=0, 1, 2, or 3;
L is a bond, or is C(=O);
X is (CH$_2$)$_n$, O, O(CH$_2$)$_n$, (CH$_2$)$_n$O, NR, (CH$_2$)$_n$NR, or NR(CH$_2$)$_n$;
Y is C(=O), C(=O)(CH$_2$)$_n$, NR, NR(CH$_2$)$_n$, C(=O)NR, or C(=O)NR(CH$_2$)$_n$;
n=1, 2, or 3;
or a pharmaceutically acceptable salt or a hydrate thereof.

2. The method of claim 1, wherein the compound of formula (1A) is not any of

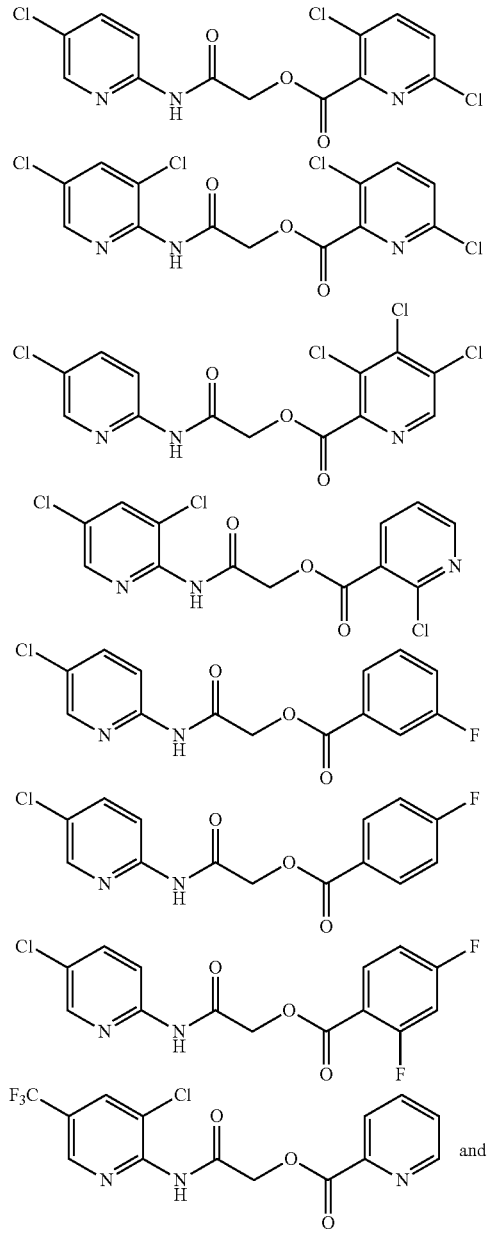

-continued
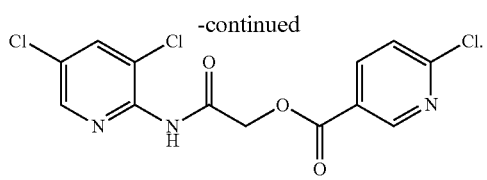
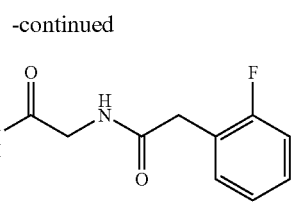
3. The method of claim 1, wherein L is C=O.
4. A method of inhibiting, within a living cell, the interaction of NF-κB essential modulator (NEMO) with IκB kinase-β (IKK-β) at the NEMO binding domain (NBD), comprising exposing the cell to an effective amount or concentration of a compound selected from the following table:
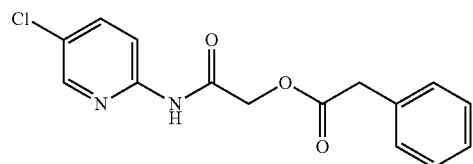
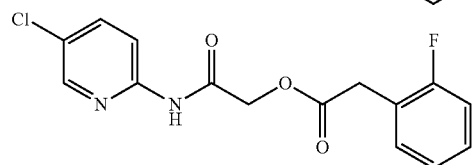
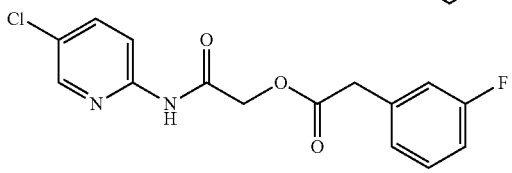
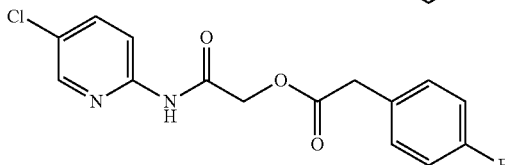
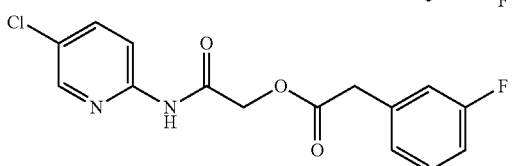
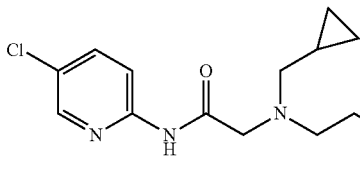
and
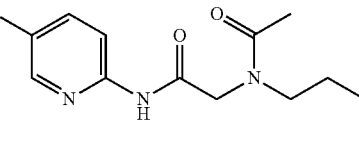
* * * * *